United States Patent [19]

Lipinski

[11] Patent Number: 4,853,410

[45] Date of Patent: Aug. 1, 1989

[54] HYDROXYACETIC ACID DERIVATIVES FOR THE TREATMENT OF DIABETIC COMPLICATIONS

[75] Inventor: Christopher A. Lipinski, Waterford, Conn.

[73] Assignee: Pfizer Inc., New York, N.Y.

[21] Appl. No.: 130,360

[22] PCT Filed: Jan. 17, 1986

[86] PCT No.: PCT/US86/00091

§ 371 Date: Oct. 9, 1987

§ 102(e) Date: Oct. 9, 1987

[87] PCT Pub. No.: WO87/04344

PCT Pub. Date: Jul. 30, 1987

[51] Int. Cl.$^4$ .................... A61K 31/38; A61K 31/35; C07D 311/96; C07D 311/04; C07D 335/06
[52] U.S. Cl. ..................... 514/432; 514/437; 514/453; 514/455; 514/456; 514/866; 549/23; 549/25; 549/27; 549/28; 549/345; 549/383; 549/384; 549/389; 549/395
[58] Field of Search .................. 549/25, 27, 28, 345, 549/383, 384, 389, 395; 514/432, 437, 453, 455, 456, 866

[56] References Cited

U.S. PATENT DOCUMENTS

| | | | |
|---|---|---|---|
| 3,359,161 | 12/1967 | Petersen et al. | 167/55 |
| 3,821,383 | 6/1974 | Sestanj et al. | 424/258 |
| 4,117,230 | 9/1978 | Sarges | 548/309 |
| 4,130,714 | 12/1978 | Sarges | 548/309 |
| 4,200,642 | 4/1980 | Schnur | 424/272 |
| 4,210,663 | 7/1980 | Belletire | 424/275 |
| 4,286,098 | 8/1981 | Sarges | 548/309 |
| 4,305,955 | 12/1981 | Belletire | 424/275 |
| 4,486,428 | 12/1984 | Eggler | 514/235.5 |
| 4,503,066 | 3/1985 | Brittain et al. | 514/409 |
| 4,540,704 | 9/1985 | Ueda et al. | 514/389 |

OTHER PUBLICATIONS

Ricci et al; *C. R. Acad. Sci. Paris Serie C;* 1975, pp. 1023–1025.

*Primary Examiner*—Mary C. Lee
*Assistant Examiner*—Mary Sue Howard
*Attorney, Agent, or Firm*—Peter C. Richardson; J. Trevor Lumb; Robert K. Blackwood

[57] ABSTRACT

Racemic and chiral (2R,4R)-4-c-hydroxy-2-4-(substituted)chroman(and thiochroman)-4-acetic acids and their pharmaceutically acceptable salts, their use in the treatment of diabetic complications and intermediates therefor.

38 Claims, No Drawings

HYDROXYACETIC ACID DERIVATIVES FOR THE TREATMENT OF DIABETIC COMPLICATIONS

BACKGROUND OF THE INVENTION

The present invention is concerned with certain racemic and optically active (2R,4R) hydroxyacetic acid derivatives which are 4-c-hydroxy-2-r-(substituted)-chroman (and thiochroman)-4-acetic acids and pharmaceutically-acceptable salts thereof which, by their inhibition of the aldose reductace enzyme, are useful in the treatment of diabetic complications. It is also concerned with intermediates useful in the synthesis of these compounds.

Compounds, such as sorbinil (S-6-fluorospiro[chroman-4,4'-imidazoline]-2',5'-dione), which have aldose reductase inhibitory activity, are of value in controlling certain chronic complications arising from diabetes mellitus (e.g., diabetic cataracts and neuropathy). The racemic precursor of sorbinil (and analogs thereof) were originally reported by Sarges in U.S. Pat. No. 4,117,230. Sorbinil itself, which is chiral, was first reported by Sarges in U.S. Pat. No. 4,130,714. Its chloro analog (in which 6-chloro replaces 6-fluoro) has also been reported (Sarges, U.S. Pat. No. 4,286,098), as has the 2R-methyl analog of sorbinil (Ueda et al., U.S. Pat. No. 4,540,704).

Non-hydantoin compounds previously reported to inhibit aldose reductase include halogen substituted chroman-4-carboxylic and chroman-4-acetic acids (Belletire, U.S. Pat. No. 4,210,663), and spiro[chroman-4,5'-oxazolidin]-2',3'-diones (Schnur, U.S. Pat. No. 4,200,642).

The chemical nomenclature employed herein is that of the "IUPAC Nomenclature of Organic Chemistry, 1979 Edition," Pergammon Press. Thus, chromans are named as such as permitted under Rule B-2.12 at page 62; thiochromans (in which sulfur replaces the oxygen atom of chroman) are named according to Rule B-4 "replacement nomenclature" at page 68 as 3,4-dihydro-2H-1-thianaphthalenes; racemic cis-trans isomers are named according to Rule E-2.3.4 at page 478 in which c is used as an abbreviation for cis and r is used as an abbreviation for the reference group; and R and S are used to designate chiral carbon atoms according to Rule E-4.9 at 481 and the Sequence Rule at page 486 et seq.

SUMMARY OF THE INVENTION

The present invention is directed to a racemic compound having the relative stereochemical formula or a chiral compound having the absolute stereochemical formula

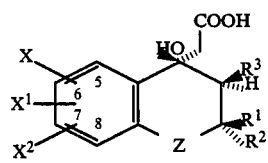

wherein

Z is —O—, —S—,

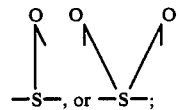

$R^1$ and $R^2$ are taken separately;

$R^1$ is $(C_1-C_4)$alkyl, trifluoromethyl or $(CH_2)_n$Ar where n is 0, 1 or 2 and Ar is phenyl or phenyl mono- or disubstituted by methoxy, fluoro, chloro or bromo, where disubstituents are the same or different; and $R^2$ is hydrogen, methyl or ethyl; or $R^1$ and $R^2$ are taken together and are $(CH_2)_4$ or $(CH_2)_5$;

$R^3$ is hydrogen or methyl; with the provisos that when either Z is other than —O—, or $R^1$ is other than methyl, ethyl or trifluoromethyl, both $R^2$ and $R^3$ are hydrogen;

X is hydrogen, a first substituent at the 6-position which is fluoro, chloro, bromo, methyl, nitro, cyano, methanesulfonyl or benzoyl, with the proviso that when Z is other than —O—, X is other than hydrogen and is a first substituent at the 6-position which is fluoro, chloro, cyano or nitro; and $X^1$ and $X^2$ are taken separately;

$X^1$ is hydrogen, a first substituent at the 7-position which is fluoro, chloro, bromo, carboxy or methyl, or a second substituent at either the 5- or 7-position which is fluoro, chloro, bromo, $(C_1-C_3)$alkyl, $(C_1-C_3)$alkoxy or benzyloxy; and $X^2$ is hydrogen, or a first or second substituent at the 8-position which is fluoro, chloro, bromo or $(C_1-C_3)$alkyl; or $X^1$ and $X^2$ are taken together and are 7,8-benzo; or a pharmaceutically-acceptable cationic salt thereof.

For their generally greater activity, the chiral variants of the compound of the formula (I) are preferred, the preferred value of $R^1$ is methyl with $R^2$ and $R^3$ as hydrogen, the preferred value of Z is oxygen (—O—), and the preferred value of X is 6-fluoro, 6-chloro, 6-cyano or 6-nitro with $X^1$ as hydrogen, 7-fluoro, 7-chloro, 7-bromo, 7-methyl, 7-ethyl or 7-methoxy and $X^2$ as hydrogen. Most preferred racemic compounds of the formula (I) are:

(1) those in which Z is —O—, $R^1$ is methyl, $R^2$, $R^3$ and $X^2$ are each hydrogen and $X/X^1$ are 6-fluoro-7-chloro, 6-fluoro-7-bromo, 6-chloro-7-bromo, 6-chloro-7-methyl or 6,7-dichloro;

(2) those in which Z is —O—, $R^1$ is ethyl or 2-phenylethyl, $R^2$, $R^3$, $X^1$ and $X^2$ are each hydrogen and X is 6-fluoro; or Z is —O—, $R^1$ is trifluoromethyl, $R^2$, $R^3$ and $X^2$ are each hydrogen, and $X/X^1$ are 6,7-dichloro;

(3) those in which Z is —S—, $R^1$ is methyl, $R^2$, $R^3$, $X^1$ and $X^2$ are each hydrogen and X is 6-fluoro or 6-nitro; or Z is —S—, $R^1$ is methyl, $R^2$, $R^3$ and $X^2$ are each hydrogen and $X/X^1$ are 6,7-dichloro.

Most highly preferred compounds are the chiral compounds of the formula (I) wherein Z is —O—, $R^1$ is methyl, $R^2$, $R^3$ and $X^2$ are each hydrogen, and $X/X^1$ are 6-fluoro-7-chloro or 6,7-dichloro.

The expression "pharmaceutically-acceptable salts" here refers to carboxylate salts where the cation is such as (but not limited to) sodium, potassium, calcium, magnesium, ammonium, or protonated benzathine (N,N'-dibenzylethylenediamine), choline, ethanolamine, diethanolamine, ethylenediamine, meglamine (N-methylglucamine), benethamine (N-benzylphenethylamine), piperazine or tromethamine (2-amino-2-hydroxymethyl-1,3-propanediol).

The invention is also directed to pharmaceutical compositions for the control of chronic diabetic complications in mammals which comprise a compound of the above formula (I) in a pharmaceutically-acceptable carrier and to a method of controlling chronic diabetic complications which comprises administering to a mammal suffering from chronic diabetes a chronic diabetic complication controlling amount of a compound of the above formula (I).

The present invention also encompasses intermediates useful as precursors of the compounds of the above formula (I), viz., racemic compounds having the relative stereochemical formula or a chiral compound having the absolute stereochemical formula

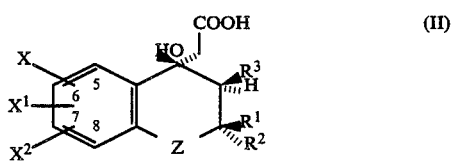

wherein R is ($C_1$–$C_4$)alkyl, allyl or phenyl, and Z, $R^1$, $R^2$, $R^3$, X, $X^1$ and $X^2$ are as defined above.

DETAILED DESCRIPTION OF THE INVENTION

The aldose reductase inhibiting compounds (I) of the present invention are readily prepared by a two-stage chemical sequence from 4-chromanones or 4-thiochromanones (2H,3H-1-thianaphthalen-4-ones) of the absolute or relative stereochemical formula

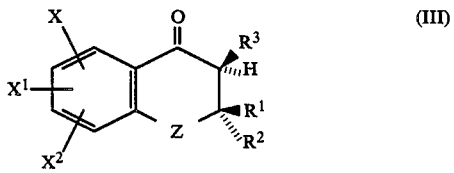

wherein $R^1$, $R^2$, $R^3$, X, $X^1$, $X^2$ and Z are as defined above. Of course, when $R^3$ is hydrogen, and relative stereochemistry is intended, that will be the simple racemate, since there are no possible cis-trans isomers. When the chiral product is desired, this is generally accomplished either by use of the appropriate chiral chromanone (III) or resolution of the racemic compound (I), e.g., as the brucine salt when Z=—O—, $R^2$=$R^3$=$X^2$=H, $R^1$=$CH_3$, and X/$X^1$=6,7-diCl.

Two basic methods are available for the first stage, the conversion of chromanone (III) to hydroxyacetate ester (II), as follows:

(A) The lithium salt of a secondary amine, preferably a sterically hindered secondary amine such as diisopropylamine, is formed in a reaction-inert solvent such as tetrahydrofuran, conveniently by reaction of the amine with substantially 1 molar equivalent of n-butyllithium in hexane. Although temperature is not critical at this stage, formation of the lithium amine salt is conveniently carried out at −70° to 30° C., e.g., in an ice-water bath at 0°–5° C. or even lower in the temperature range (e.g., −50° to −60° C.) as the mixture is being chilled for further reaction. The lithium salt is then reacted with substantially 1 molar equivalent of ($C_1$–$C_4$)alkyl, allyl or phenyl acetate at −50° to −90° C. and then with 0.1 to 0.95 molar equivalent of the chromanone/thiochromanone (III) in the same temperature range. Following completion of the reaction, generally within a few hours even when only a slight excess of the lithium salt is employed, the reaction mixture is quenched with excess water, warmed and, if isolation of the ester is desired, immediately extracted into a water-immiscible organic solvent from which it is isolated and, if desired, purified by standard methods (e.g., by stripping of the solvent and, if desired, chromatography on silica gel). Alternatively, the water-quenched reaction mixture containing the ester (II), optionally made more basic with a strong base (e.g., an alkali metal hydroxide), is allowed to hydrolyze to the desired acid according to the second stage further described below. Because of the ease with which it hydrolyzes, the latter is the preferred method when R is phenyl. When R is allyl, a second alternative is to extract the ester into a suitable solvent such as methylene chloride, dry the extract, and proceed with the special palladium-triphenyl phosphine conversion to acid as described below.

(B) Particularly when R is ($C_1$–$C_4$)alkyl, the chromanone is reacted with at least 1 molar equivalent of a ($C_1$–$C_4$)alkyl 2-haloacetate (where halo is chloro, bromo or iodo, preferably bromo) in the presence of at least 1 molar equivalent of finely divided zinc (e.g., obtained by filing mossy zinc). Conveniently, a 0.1 to 1 molar excess of both the haloacetate and zinc are employed. The reaction is carried out in a reaction-inert solvent such as benzene. Reaction temperature is not critical, but is generally in the range of 0°–60° C., conveniently initiated at ambient temperature (18°–26° C.) and allowing the reaction to exotherm to 35°–60° C. Following completion of the reaction, generally less than 1 hour at 18° to 60° C., the mixture is usually quenched with aqueous acid, and product extracted into a water-immiscible organic solvent, recovered and, if desired, purified according to standard methods as noted above.

As used herein, the expression "reaction-inert solvent" refers to a solvent which does not interact with starting material, reagents, intermediates or desired product in a manner which adversely affects the yield of the desired product.

Regardless of the value of the group R, the second stage hydrolysis can be simply carried out in an aqueous solvent in the presence of one or more equivalents of an alkali metal (lithium, sodium or potassium) hydroxide. Temperature is not critical, but is generally in the range of 0°–50° C., conveniently ambient (18°–26° C.). As noted above, when intermediate esters derived from lithio alkyl acetates are hydrolyzed without isolation, lithium hydroxide formed in the quench of the above acetate ester/chromanone condensation represents an appropriate source of the required base. The product is conveniently isolated in its free acid form by acidification, extraction into a water-immiscible organic solvent and partial or complete stripping with optional addition of a non-solvent. If desired, the product is purified by standard methods (e.g., recrystallization, chromatography).

When R is allyl, the second stage is alternatively carried out in a reaction-inert, anhydrous solvent such as methylene chloride or ethyl acetate by the action of 1–1.1 molar equivalents of an alkali metal salt of a lipophilic acid (e.g., sodium or potassium 2-ethylhexanoate) in the presence of catalytic amounts of tetrakis(triphenylphosphine)palladium and triphenylphosphine. Again temperature is not critical, e.g., 0°–50° C., conveniently ambient temperature is satisfactory. In this case the alkali metal salt is optionally isolated directly from the reaction mixture, with optional partial stripping and/or the addition of a non-solvent. Alternatively, the reaction is diluted with water and product isolated as the free acid according to the preceding paragraph.

When the product (I) is isolated as a salt, and the free acid is desired, or when the product (I) is resolved as the salt of a chiral amine, the free acid is obtained by standard methods of acidification and extraction as described. If desired, free acid product is converted to a pharmaceutically-acceptable salt, again by standard methods, e.g., by combining the free acid and substantially 1 equivalent of an appropriate base (e.g., NaOH, NaHCO$_3$, 0.5 Na$_2$CO$_3$, KOH, 0.5 Ca(OH)$_2$, 0.5 Mg(OH)$_2$, NH$_3$, NH$_4$OH, benzathine, choline, ethanolamine, diethanolamine, 0.5 or 1.0 ethylenediamine, meglumine, 0.5 or 1.0 piperazine or tromethamine) in a suitable solvent and isolating by filtration, if necessary after stripping, the addition of a non-solvent, and/or salting out of an aqueous phase, e.g., the sodium salt with sodium chloride, with optional extraction into a polar, water-immiscible organic solvent.

When the sulfoxide (I, Z=SO) or the sulfone (I, Z=SO$_2$) is desired, and the sulfur is not already in the desired oxidation state, the sulfide or sulfoxide is readily oxidized to the sulfone by reaction with an excess of a peracid, conveniently, m-chloroperbenzoic acid, in a reaction-inert solvent at 0°–50° C., conveniently at ambient temperature. Under the same conditions, but limiting the oxidant to 1 molar equivalent, and preferably at temperatures lower in the range, the sulfide is converted to sulfoxide. The same oxidations can be carried out at an earlier stage in the synthesis, e.g., on the ester precursor (II) or on the chromanone/thiochromanone (III).

A variety of methods are available for the synthesis of the chromanone/thiochromanone precursors of the formula (III). It will be evident to those skilled in the art that the particular method chosen will depend largely upon the availability of the required starting material, the particular aromatic substitution desired and upon the number of steps and the over-all yield possible with a given method. Each of the available methods, now summarized, is specifically exemplified below.

(A) Using essentially standard methods of organic chemistry for each step, a substituted phenol ($\phi$OH) and a 2-hydroxycarboxylate ester (HOCR$^1$R$^2$COOR) are coupled to form the ether ($\phi$OCR$^1$R$^2$COOR) which is reduced to the alcohol ($\phi$OCR$^1$R$^2$CH$_2$OH) and then converted to the bromide ($\phi$OCR$^1$R$^2$CH$_2$Br). The next stages of the synthesis are as follows

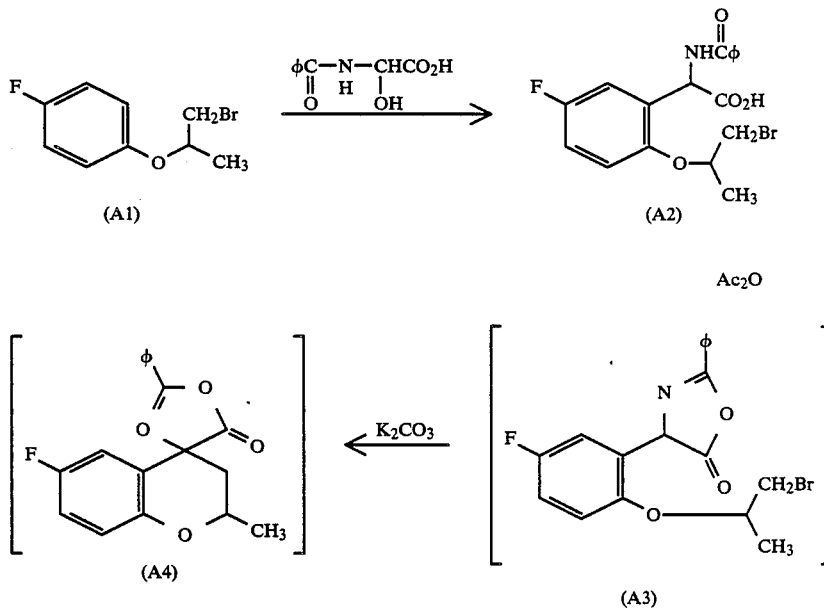

In the present synthesis, the compounds of the type (A3) and (A4) are generally not isolated. Rather, the compound (A4) is treated in situ with aqueous hydrochloric acid to form a substituted 4-(N-benzoylamino)-chroman-4-carboxylic acid, which is in turn oxidatively decarboxylated and hydrolyzed to yield the desired chromanone, e.g.,

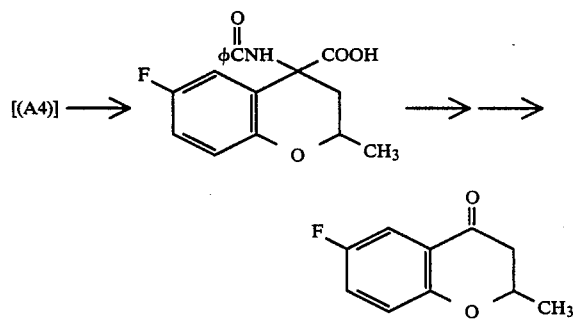

[cf. Lohmar and Steglich, Angew, Chem. Int. Ed. Engl. 17, pp. 450–451 (1978) and Cue et al., U.S. Pat. No. 4,431,828.]

This method is particularly well suited for the synthesis of chiral chromanones, most particularly those where R$^2$=R$^3$=H and R$^1$=CH$_3$ or CH$_2$C$_6$H$_5$ by use of readily available ethyl S-lactate or L-phenylalanine as starting materials (see exemplary preparations below).

(B) Using essentially standard methods of organic chemistry, aromatic substituted 2-acetylphenols or 2-acetylthiophenols (which are frequently readily available by Fries type rearrangement or Friedel-Crafts reaction) are condensed with an ester (e.g., $R_1COOCH_3$) to form a 1-(2-hydroxyphenyl)-1,3-butanedione derivative which is cyclized with dehydration to form a benzo[b]pyran derivative and finally reduced with $LiAlH_4$ to produce the desired chroman-4-one, e.g.,

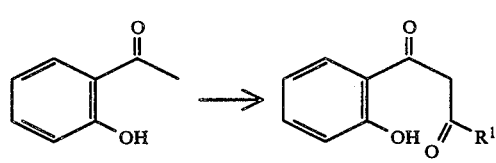

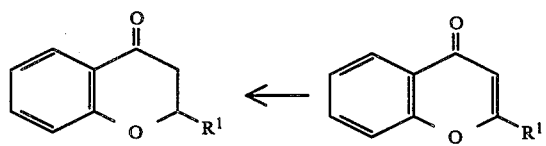

(C) Alternatively, such a 2-acetylphenol or 2-acetylthiophenol is condensed with a ketone and cyclized to yield the desired chromanone in essentially one step, e.g.,

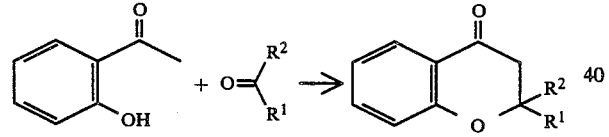

(D) Similarly, such a 2-acetylphenol or 2-acetylthiophenol is condensed with an aldehyde to yield the desired chromanone, e.g.,

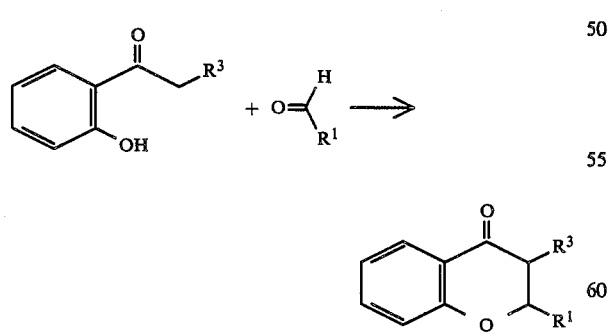

(E) Alternatively, such a 2-acetylphenol or 2-acetylthiophenol is condensed with ethylacetate and cyclized with dehydration to form a benzo[b]pyran which is then condensed with a Grignard reagent, e.g.,

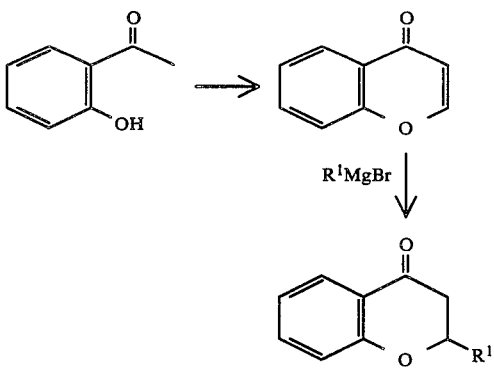

(F) (G) (H) Substituted phenols or thiophenols are condensed with beta-lactones and then cyclized under a variety of conditions, e.g.,

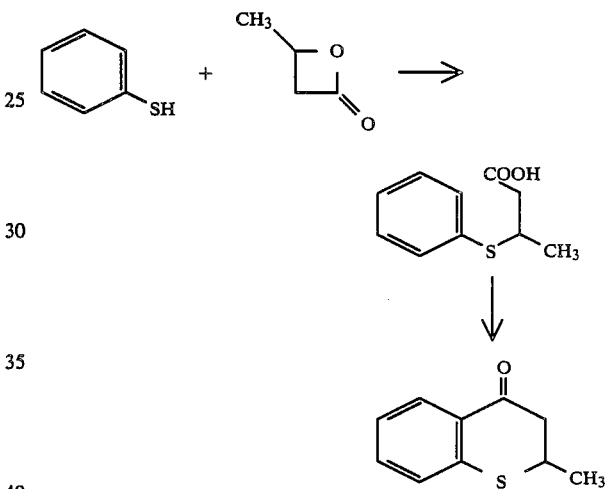

(I) (J) (K) (L) Substituted phenols or thiophenols are condensed with alpha, beta-unsaturated acids and then cyclized under a variety of conditions, e.g.,

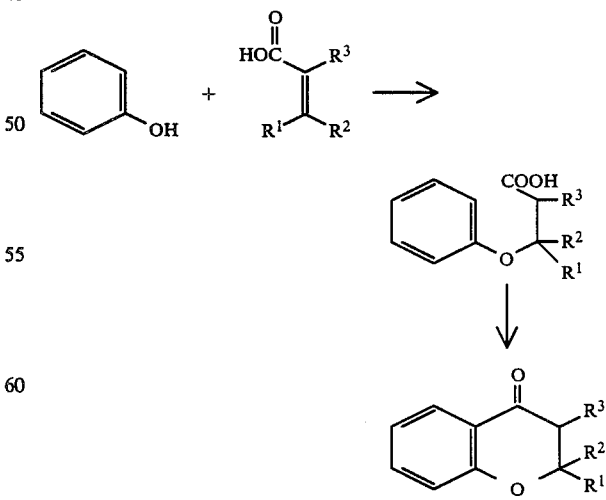

(M) A variety of miscellaneous methods are also applied in the synthesis of chromanones/thiochromanones, e.g., aromatic nitration, reduction of nitro groups to amino groups, Sandmeyer-type conversions of amino groups to halogen or cyano, conversion of carbalkoxy groups to amides and then to cyano, conversion of sulfides to sulfoxides or sulfones, and so forth.

The present compounds of the formula (I) are tested in vitro for their ability to reduce or inhibit aldose reductase enzyme activity, following the procedure described in U.S. Pat. No. 3,821,383 and based on the procedure of Hayman et al., Journal of Biological Chemistry, 240, 877 (1965). The substrate employed is partially purified aldose reductase enzyme obtained from human placenta. The results obtained with each compound at a concentration of $10^{-5}M$ or lower are expressed as percent inhibition of enzyme activity, or, when tested at several concentration levels, expressed as an $IC_{50}$, the inhibition concentration calculated to show 50% inhibition of enzyme activity. With minor exceptions, such as racemic 6,7-dichloro-c-4-hydroxy-r-2-methyl-3,4-dihydro-2H-1-thianaphthalene-4-acetic acid 1,1-dioxide (the compound I wherein $Z=SO_2$, $R^1=CH_3$, $R^2=R^3=X^2=H$, and $X/X^1=6,7$-diCl) which shows 37% inhibition of enzyme at $10^{-5}M$, the present compounds generally show an $IC_{50}$ which is less than $10^{-5}M$. Indeed, the more active racemic compounds of the present invention, such as those wherein Z is oxygen, $R^1$ is $CH_3$ or $CF_3$, $R^2=R^3=X^2H$, X is 6-F, 6-Cl, 6-CN or 6-$NO_2$ and $X^1$ is H, 7-F, 7-Cl, 7-Br, 7-$CH_3$, 7-$C_2H_5$ or 7-$OCH_3$, show $IC_{50}$ values generally in the range of about $8.6\times10^{-7}M$ (the value found for $R^1=CH_3$, $X=6$-Cl, $X^1=H$) to about $5.1\times10^{-8}M$ (the value found for $R^1=CH_3$, $X=6$-$NO_2$, $X^1=7$-Cl). Based on $IC_{50}$ values, the chiral varients of the present compounds are generally twice as active as the corresponding racemic compounds.

The present compounds of the formula (I) are tested in vivo for their ability to reduce or inhibit sorbitol accumulation in the sciatic nerve of streptozotocinized (i.e., diabetic) rats by the procedure essentially described in U.S. Pat. No. 3,821,383. In the present study, the amount of sorbitol accumulation in the sciatic nerves was measured 27 hours after induction of diabetes. The compounds are generally administered orally at doses ranging from 2.5 to 100 mg/kg at 4, 8 and 24 hours following the administration of streptozotocin. The results obtained in this manner are presented in terms of percent inhibition afforded by the test compound as compared to the case where no compound was administered (i.e., the untreated animal where sorbitol levels normally rise from approximately 50–100 mM/g tissue to as high as 400 mM/g tissue during the test period). In this test values below 20% are not always experimentally and statistically significant. Not all of the compounds of the present invention show in vivo activity by this oral test. Such compounds will find parenteral, or more particularly, topical use as described below.

The more active compounds of the formula (I) wherein Z is oxygen, $R^1$ is methyl, $R^2$, $R^3$ and $X^2$ are hydrogen, X is 6-fluoro, 6-chloro, 6-cyano or 6-nitro and $X^1$ is hydrogen, 7-fluoro, 7-chloro, 7-bromo or 7-methyl, have generally demonstrated activity in the range of 54–91% inhibition of sorbitol accumulation in the diabetic rat sciatic nerve at an oral dose of 25 mg/kg.

The compounds of this invention are all readily adapted to therapeutic use as aldose reductase inhibitors for the control of chronic diabetic complications in mammals. They are administered either orally or parenterally, or topically as eye drops, in dosages ranging from about 0.1 to 10 mg/kg of body weight per day in single or divided doses. Of course, in particular situations, doses outside of this range will be used at the discretion of the attending physician.

The compounds of this invention can be administered in a wide variety of different dosage forms, i.e., they may be combined with various pharmaceutically-acceptable inert carriers in the form of tablets, capsules, lozenges, troches, hard candies, powders, sprays, elixirs, syrups, injectable or eye drop solutions and the like. Such carriers include solid diluents of fillers, sterile aqueous media and various non-toxic organic solvents. For purposes of oral administration, tablets containing various excipients such as sodium citrate, calcium carbonate and calcium phosphate are employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also includes lactose or milk sugar as well as high molecular weight polyethylene glycols. When aqueous suspensions and/or elixirs are desired for oral administration, the essential active ingredient therein can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble, alkali metal or alkaline-earth metal salts previously enumerated. Such aqueous solutions should be suitably buffered, if necessary, and the liquid diluent first rendered isotonic with sufficient saline or glucose. These particular aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of topical administration, dilute, sterile, aqueous solutions (usually in about 0.1% to 5% concentration), otherwise similar to the above parenteral solutions, are prepared in containers suitable for dropwise administration to the eye.

The present invention is illustrated by the following examples. However, it should be understood that the invention is not limited to the specific details of these examples.

EXAMPLE 1

Ethyl 2R,4R-7-Chloro-6-fluoro-4-hydroxy-2-methylchroman-4-acetate

A solution of 8.7 ml (6.2 mmol) of diisopropylamine in 150 ml tetrahydrofuran was cooled to 0° C. and 23.8 ml (6.2 mmol) 2.6M n-butyllithium in hexane was added, keeping the temperature below 5° C. The reaction was cooled to −78° C. and 6.0 ml (6.2 mmol) ethyl acetate was added followed by a solution of 12.0 g (5.6 mmol) of 2R-7-chloro-6-fluoro-2-methylchroman-4-one in 50 ml tetrahydrofuran, keeping the reaction temperature below −65° C. The reaction was quenched with 60 ml water, diluted with 100 ml diethyl ether, and warmed to 10° C. An additional 60 ml water was added and the organic layer separated. The aqueous layer was extracted with 150 ml diethyl ether and the combined ether layers were washed with 150 ml brine, dried over magnesium sulfate, filtered and concentrated in vacuo to give the product, 17.7 g, as an oil.

$^1$H-NMR(CDCl$_3$)delta(ppm): 7.10 (d, 1H, J=10), 6.68 (d, 1H, J=6), 4.30 (m, 1H), 4.13 (q, 2H), 2.73 (s, 2H), 2.07 (m, 2H), 1.33 (d, 3H), 1.20 (t, 3H).

EXAMPLE 2

2R,4R-7-Chloro-6-fluoro-4-hydroxy-2-methylchroman-4-acetic Acid

To a solution of 0.875 g (15.6 mmol) potassium hydroxide in 43 ml ethanol was added 4.3 g (14.2 mmol) of title product of the preceding Example. The reaction was stirred at 23° C. for 4 hours and then concentrated in vacuo. The residue was dissolved in 40 ml water and washed with 3×40 ml diethyl ether. The aqueous was acidified with 16 ml 1N hydrochloric acid and then extracted with 3×50 ml diethyl ether. The acidic ether extracts were combined, washed with 50 ml brine, dried over anhydrous magnesium sulfate, filtered and concentrated in vacuo to give 3.5 g of a foam which was purified by flash chromatography on 200 cc silica gel using 1:1 diethyl ether:hexane as eluant to give 2.7 g of a solid foam which liquified at 42°–50° C. and effervesced at 60°–95° C.; [alpha]$_D^{25}$=104.9 (CH$_3$OH, C=1, corrected for ether content).

$^1$H-NMR(CDCl$_3$)delta(ppm): 7.20 (d, 1H), 6.78 (d, 1H), 4.20 (m, 1H), 2.84 (s, 2H), 2.26 (d, 1H), 1.88 (t, 1H), 1.37 (d, 3H). The NMR indicated about 20 mol percent entrapped diethyl ether in the foam.

Exact mass:
Calculated for C$_{12}$H$_{12}$O$_4$Cl$^{35}$F: m/e 274.0408.
Found: m/e 274.0378.
Chiral HPLC analysis showed 1% of the 2S-cis-methyl enantiomer.

EXAMPLE 3

Sodium 2R,4R-7-Chloro-6-fluoro-4-hydroxy-2-methylchroman-4-acetate

The amorphous acid of the preceding Example (9.0 g, 32.8 mmol) was dissolved in 65 ml methylene chloride and covered with 65 ml distilled water. The pH of the aqueous layer was monitored with a pH meter probe. To the well-stirred two-layer system was added 1N sodium hydroxide dropwise over a 1 hour period at 23° C. maintaining the pH below 11. The final pH after addition of 31 ml of 1N sodium hydroxide was 7. The layers were separated and the aqueous layer was washed with 50 ml methylene chloride and then freeze dried to give 9.9 g of an amorphous, hydroscopic white powder. Drying at 110° C. under high vacuum gave 9.24 g amorphous white solid. This material was slurried in 100 ml warm diethyl ether and 50 ml of acetonitrile was added. Heating at reflux on the steam bath resulted in solution of most of the solid. After standing for 2 hours, 100 ml diethyl ether was added and seed crystals of crystalline sodium salt were added. Following 2 hours of stirring, an additional 100 ml diethyl ether was added and stirring was continued at 23° C. for 20 hours. In the absence of seed crystals slow conversion of amorphous to crystalline sodium salt occurs by slurrying in diethyl ether-acetonitrile and can be monitored under a microscope as growth of crystalline salt starting at the periphery of clumps of amorphous salt. The crystalline salt was isolated by filtration, the solid was washed with diethyl ether and dried at 110° C. at high vacuum to give 8.7 g white crystalline material; m.p. 250°–253° C.; [alpha]$_D^{25}$=130.5° (CH$_3$OH, C=1).

$^1$H-NMR(DMSO-d$_6$)delta(ppm): 8.92 (broad s, 1H), 7.24 (d, 1H), 6.75 (d, 1H), 4.21 (m, 1H), 2.27 (m, 2H), 1.99 (d, 1H), 1.62 (t, 1H), 1.26 (d, 3H).

Analysis calculated for C$_{12}$H$_{11}$ClFO$_4$Na: C, 48.58; H, 3.74%.
Found: C, 48.49; H, 3.77%.

EXAMPLE 4

Ethyl 6,7-Dichloro-c-4-hydroxy-r-2-methylchroman-4-acetate

A solution of 0.242 mol of lithium diisopropylamide formed at 0° C. from 93 ml 2.6M n-butyl lithium in hexane and 0.34 ml (0.242 mol) diisopropylamine in 825 ml tetrahydrofuran was cooled to −78° C. To this was added 23.7 ml (0.242 mol) ethyl acetate over 25 minutes, followed by dropwise addition of 50.9 g (0.220 mol) of 6,7-dichloro-2-methyl-chroman-4-one dissolved in 100 ml tetrahydrofuran. Upon completion of the addition, 50 ml water was added dropwise and the reaction was allowed to warm slowly to 23° C. After dilution of the reaction mixture with 1 liter water, the product was extracted with 2×500 ml diethyl ether, backwashed with 2×500 ml water and 500 ml brine, and dried over magnesium sulfate. Concentration in vacuo gave 66.1 g (94%) of the product as a light brown solid. An analytical sample was obtained by trituration with hexane to give product; m.p. 80°–84° C.

$^1$H-NMR(Me$_2$SO)delta(ppm): 7.57 (s, 1H), 6.92 (s, 1H), 4.48 (broad s, 1H), 4.24 (m, 1H), 4.24 (q, 2H), 2.80 (s, 2H), 2.21 (m, 1H), 1.94 (m, 1H), 1.41 (d, 3H), 1.30 (t, 3H).

Analysis calculated for C$_{14}$H$_{16}$O$_4$Cl$_2$: C, 52.68; H, 5.05%.
Found: C, 52.69; H, 4.99%.

EXAMPLE 5

6,7-Dichloro-c-4-hydroxy-r-2-methylchroman-4-acetic Acid

To a solution of 31.3 g (0.473 mol) KOH in 1.5 liters absolute ethanol at 23° C. was added 151.1 g (0.473 mol) of title product of the preceding Example. The clear solution was stirred at 23° C. for 4 hours and then concentrated in vacuo. The resultant yellowbrown, wet solid was diluted with 600 ml diethyl ether and the white potassium salt was collected by filtration and washed well with ether and air dried to give 119 g salt, m.p. 247°–252° C. with decomposition. 117.5 g of salt was added to 1 liter water, stirred with 1 liter diethyl ether at 0° C. and 30 ml 12N HCl was added dropwise. The ether layer was separated and the aqueous layer was extracted with 500 ml ethyl acetate. The combined organic layers were washed with 500 ml brine, dried over anhydrous magnesium sulfate and concentrated to an off-white solid. Trituration with a 1:1 mixture of methylene chloride-hexane gave the present title product as a white powder, 101.1 g (73%); m.p. 164°–167° C.

$^1$H-NMR(Me$_2$SO)delta(ppm): 7.67 (s, 1H), 7.03 (s, 1H), 5.65 (very broad s, 1H), 4.44 (m, 1H), 2.69 (q, 2H), 2.56 (m, 1H), 1.75 (t, 1H), 1.34 (d, 3H).

EXAMPLE 6

Brucine Salt
2R,4R-6,7-Dichloro-4-hydroxy2-methylchroman-4-acetic Acid

To 2.3 liters acetonitrile was added 99.6 g (0.342 mol) of title product of the preceding Example and 147.0 g (0.342 mol) brucine dihydrate. The mixture was brought to reflux to effect almost complete solution of the reagents and slightly hazy particulate matter was removed by filtration of the hot solution. The filtrate was allowed to cool to 23° C. and after 20 hours, 96.5 g of white solid; m.p. 184°-187° C., [alpha]$_D^{25}$ = +11° (CH$_3$OH, C=1) was collected by filtration. The mother liquors were set aside for recovery of the 2S,4S enantiomer and racemate and the entire batch of white solid was taken up in 1.5 liters acetonitrile at reflux to give a clear solution. The volume was reduced to 1.2 liters by boiling off acetonitrile, the solution was allowed to cool to 23° C. and after 20 hours partially purified title product recovered by filtration, 65 g of white crystals; m.p. 191°-195° C.; [alpha]$_D^{25}$ = +30° (CH$_3$OH, C=1). This latter material was dissolved in 1.4 liters acetonitrile at reflux, the solution was allowed to cool to 23° C. and after 20 hours there was isolated by filtration 52.7 g of purified title product, white crystals; m.p. 193°-197° C.; [alpha]$_D^{25}$ = +36° (CH$_3$OH, C=1). The absolute 2R,4Rstereochemistry of this compound was shown by X-ray crystallographic analysis.

EXAMPLE 7

2R,4R-6,7-Dichloro-4-hydroxy2-methylchroman-4-acetic Acid

Purifed title product of the preceding Example (52.0 g) was partitioned between 500 ml 0.5N HCl and a mixture of 500 ml diethyl ether and 100 ml ethyl acetate. The organic layer was washed with 4×300 ml 0.5N HCl followed by 300 ml brine and then dried over magnesium sulfate. Concentration in vacuo gave 22.5 g of a glassy foam still containing some solvent; [alpha]$_D^{25}$ = +102° (CH$_3$OH, C=1). This material was treated with 200 ml of 1:1 methylene chloride-hexane at reflux and about 100 mg of a white gummy substance removed from the hot solution by filtration. On cooling to 30° C. more white gummy material formed and was removed by filtration (100 mg; m.p. softens 105°, m.p. 157°-162° C.). On standing at 23° C. for 20 hours, large crystals formed and were collected by filtration to give 6.46 g of solids; m.p. 107°-111° C. with gassing, [alpha]$_D^{25}$ = +112.6° (CH$_3$OH, C=1). The mother liquors were concentrated in vacuo to a white solid, 12.0 g, [alpha]$_D^{25}$ = +121° (CH$_3$OH, C=1). To the latter solid was added 50 ml hexane, the slurry was warmed and ether was added until solution occurred. Solvent was removed at reflux until the solution became slightly cloudy. On cooling to 23° C. two phases formed. After about 1 hour crystals began growing in both phases. After standing 20 hours, the resultant crystals were removed by filtration from the single solvent phase and on drying at 23° C. gave 10.4 g of the title compound; m.p. 103°-107° C. [alpha]$_D^{25}$ = +124° (CH$_3$OH, C=1). Analysis calculated for C$_{12}$H$_{12}$O$_4$Cl$_2$: C, 49.50; H, 4.15; Cl, 24.36%.
Found: C, 48.85; H, 4.14; Cl, 24.15%.

EXAMPLE 8

Ethyl
6-Nitro-c-4-hydroxy-r-2-methylchroman-4-acetate

To a solution of 1.0 ml (7.17 mmol) diisopropylamine in 10 ml dry tetrahydrofuran at 0° C. was added 2.66 ml (7.17 mmol) 2.7M n-butyllithium in hexane. The solution was cooled to −78° C. and 0.7 ml ethyl acetate was added keeping the reaction temperature below −65° C. A solution of 1.35 g (6.52 mmol) 6-nitro-2-methylchroman4-one in 15 ml tetrahydrofuran was added keeping the temperature below −65° C. The reaction was quenched by addition of 5 ml water, warmed to 23° C. and diluted with 30 ml water and 30 ml diethyl ether. The organic layer was separated and the aqueous was extracted with 2×30 ml diethyl ether. The combined organic layers were washed with 30 ml brine, dried over magnesium sulfate and concentrated in vacuo to give the product as an oil, 1.57 g (82%).
$^1$H-NMR(CDCl$_3$)delta(ppm): 8.30 (m, 1H), 7.90 (m, 1H), 6.70 (m, 1H), 4.26 (m, 1H), 4.13 (q, 2H), 2.80 (s, 2H), 2.47-1.70 (m, 2H), 1.43 (d, 3H), 1.27 (t, 3H).

EXAMPLE 9

6-Nitro-c-4-hydroxy-r-2-methylchroman-4-acetic Acid

A solution of 1.55 g (5.25 mmol) of title product of the preceding Example in 5 ml ethanol was added to a solution of 0.294 g (5.25 mmol) potassium hydroxide in 10 ml ethanol and the reaction stirred at 23° C. for 4 hours. The reaction was diluted with 75 ml diethyl ether and the crystalline potassium salt of the product was isolated by filtration and then dissolved in 30 ml water. The aqueous solution was washed with 2×30 ml diethyl ether and the aqueous was acidified with 5.25 ml 1N hydrochloric acid and extracted with 2×30 ml diethyl ether. The ether was washed with 30 ml brine, dried over magnesium sulfate and concentrated in vacuo to an off-white solid. Trituration with hexane gave the product as a solid, 0.92 g (66%); m.p. softens 100°-105°, melts 135°-138° C. with gas evolution.
$^1$H-NMR(20:1 CDCl$_3$:DMSO)delta(ppm): 8.40 (m, 1H), 7.90 (m, 1H), 6.73 (m, 1H), 5.93 (broad s, 2H), 4.30 (m, 1H), 2.77 (s, 2H), 2.53-1.67 (m, 2H), 1.43 (d, 3H). An analytical sample was obtained by recrystallization from ether-hexane.
Analysis calculated for C$_{12}$H$_{13}$NO$_6$: C, 53.93; H, 4.90; N, 5.24%.
Found: C, 54.00; H, 4.94; N, 5.17%.

EXAMPLE 10

Ethyl
7-Chloro-6-fluoro-c-4-hydroxyr-methylchroman-4-acetate

To a solution of 1.54 ml (11 mmol) diisopropylamine in 30 ml tetrahydrofuran at −20° C. was added 4.07 ml of 2.7M n-butyllithium in hexane. The reaction was cooled to −78° C. and 1.07 ml (11 mmol) ethyl acetate was added. A solution of 2.146 g (10 mmol) 7-chloro-6-fluoro-2-methylchroman-4-one in 10 ml tetrahydrofuran was added dropwise keeping the reaction temperature below −65° C. The reaction was quenched by addition of 10 ml water and was allowed to warm to 23° C. An additional 10 ml water was added and the organic layer was separated and the aqueous was washed with 30 ml diethyl ether. The combined organic layers were washed with brine, dried over magnesium sulfate and concentrated in vacuo to yield title compound as an oil, 2.5 g (83%).

$^1$H-NMR(CDCl$_3$)delta(ppm): 7.17 (d, J=10 Hz, 1H), 6.73 (d, J=6 Hz, 1H), 4.57–3.61 (m, 2×1H), 4.17 (q, 2H), 2.77 (s, 3H), 2.43–1.76 (m, 2H), 1.33 (d, 3H), 1.23 (t, 3H).

EXAMPLE 11

7-Chloro-6-fluoro-c-4-hydroxy-r-2-methylchroman-4-acetic Acid

A solution of 2.5 g (8.26 mmol) of title product of the preceding Example in 15 ml ethanol was added to a solution of 0.463 g (8.26 mmol) potassium hydroxide in 10 ml ethanol. The reaction was stirred at 23° C. for 4 hours. The reaction was concentrated in vacuo, the residue was taken up in 20 ml water and washed with 3×20 ml diethyl ether. To the aqueous was added 9 ml 1N hydrochloric acid followed by extraction with 30 ml diethyl ether. This was washed with brine, dried over magnesium sulfate and concentrated in vacuo to give 1.68 g of a foam. Trituration with hot hexane and filtration gave the product as an off-white solid, 1.4 g (62%); m.p. 134°–136° C.

$^1$H-NMR(19.1 CDCl$_3$:Me$_2$SO)delta(ppm): 7.64 (very broad s, 2H), 7.18 (d, J=10 Hz, 1H), 6.70 (d, J=6 Hz, 1H), 4.17 (m, 1H), 2.73 (s, 2H), 2.45–1.63 (m, 2H), 1.37 (d, 3H).

Analysis calculated for C$_{12}$H$_{12}$FClO$_4$: C, 52.47; H, 4.40%.

Found: C, 52.36; H, 4.31%.

EXAMPLE 12

Ethyl 6-Chloro-7-fluoro-c-4-hydroxy-r-2-methylchroman-4-acetate

To a solution of 0.34 ml (2.56 mmol) diisopropylamine in 8 ml dry tetrahydrofuran cooled to 0° C. was added 0.98 ml (2.56 mmol) 2.6M n-butyllithium in hexane keeping the reaction temperature below 5° C. The solution was cooled to −78° C. and 0.23 ml (2.56 mmol) ethyl acetate was added. A solution of 500 mg (2.33 mmol) 6-chloro-7-fluoro-2-methylchroman-4-one in 2 ml tetrahydrofuran was added to the reaction at −70° C. The reaction was quenched with 5 ml water, warmed to 23° C., diluted with 10 ml water and extracted with 30 ml diethyl ether. The ether layer was washed with brine, dried over magnesium sulfate and concentrated in vacuo to give the product as a yellow oil, 0.611 g (87%).

$^1$H-NMR(CDCl$_3$)delta(ppm): 7.33 (d, 1H, J=8 Hz), 6.34 (d, 1H), J=11 Hz), 4.22 (m, 1H), 4.13 (q, 2H), 2.75 (s, 2H), 2.37–1.57 (m, 2H), 1.37 (d, 3H), 1.25 (t, 3H).

EXAMPLE 13

6-Chloro-7-fluoro-c-4-hydroxy-r-2-methylchroman-4-acetic Acid

To a solution of 0.113 g (2.02 mmol) potassium hydroxide in 6 ml ethanol was added 0.611 g (2.02 mmol) of title product of the preceding Example. The solution was stirred at 23° C. for 4 hours, then concentrated in vacuo and the residue taken up in 15 ml water, washed with 3×15 ml diethyl ether, acidified with 2.5 ml 1N hydrochloric acid and extracted with 2×15 ml diethyl ether. The latter, combined ether extracts were washed with brine, dried over magnesium sulfate, and concentrated in vacuo. Trituration of the residue with hexane gave the product as a white solid, 0.336 g (61%); m.p. 133°–134° C.

$^1$H-NMR(Me$_2$SO)delta(ppm): 7.59 (d, 1H, J=9 Hz), 6.83 (d, 1H, J=12 Hz), 4.42 (m, 1H), 3.36 (broad s, 1H), 2.70 (q, 2H), 2.54 (m, 1H), 1.72 (t, 1H), 1.33 (d, 3H).

Analysis calculated for C$_{12}$H$_{12}$ClFO$_4$: C, 52.47; H, 4.41%.

Found: C, 52.85; H, 4.51%.

EXAMPLE 14

Ethyl 6-Chloro-c-4-hydroxy-r-2-methylchroman-4-acetate

To a solution of 13.2 ml (94 mmol) diisopropylamine in 190 ml dry tetrahydrofuran at −20° C. was added 44.8 ml (94 mmol) 2.4M n-butyllithium in hexane. After 15 minutes stirring, the reaction was cooled to −78° C. and 9.17 ml (94 mmol) of ethyl acetate was added dropwise keeping the temperature below −70° C. After 1.5 hours at −78° C. a solution of 2.3 g (12 mmol) of 6-chloro-2-methylchroman-4-one in 10 ml tetrahydrofuran was added dropwise keeping the temperature below −70° C. After 1.5 hours at −78° C., the reaction was quenched with 10 ml water and was allowed to warm to 23° C. To the reaction was added 100 ml water and 100 ml diethyl ether. The organic layer was separated and the aqueous was extracted with 2×75 ml diethyl ether. The combined organic layers were washed with brine, dried over magnesium sulfate and concentrated in vacuo to give 5.7 g of crude product. This was subjected to flash chromatography (silica gel, 1:6 diethyl ether:hexane eluant) to give the product as a pale yellow oil, 3.5 g (100%).

$^1$H-NMR(CDCl$_3$)delta(ppm): 7.35 (m, 1H), 7.00 (m, 1H), 6.40 (m, 1H), 4.13 (m, 1H), 4.13 (q, 2H), 2.77 (s, 2H), 2.53–1.63 (m, 2H), 1.37 (d, 3H), 1.27 (t, 3H).

EXAMPLE 15

6-Chloro-c-4-hydroxy-r-2-methylchroman-4-acetic Acid

To a solution of 0.672 g (12 mmol) potassium hydroxide dissolved in 20 ml ethanol was added 3.41 g (12 mmol) of the product of the preceding Example dissolved in 14 ml ethanol. After stirring at 23° C. for 4 hours, the reaction was concentrated in vacuo and the residue was taken up in 40 ml water. The aqueous was washed with 3×20 ml diethyl ether and then acidified by addition of 12 ml 1N hydrochloric acid. Extraction with 3×20 ml diethyl ether, washing the ether with brine, drying over magnesium sulfate and concentration in vacuo gave 2.25 g of a foam. Trituration with hot hexane and filtration gave the product as a white solid, 1.9 g (61%); m.p. 119°–121° C.

$^1$H-NMR(CDCl$_3$)delta(ppm): 7.35 (m, 1H), 7.17 (broad s, 2H), 7.01 (m, 1H), 6.62 (m, 1H), 4.17 (m, 1H), 2.87 (s, 3H), 2.50–1.63 (m, 2H), 1.37 (d, 3H).

Analysis calculated for C$_{10}$H$_9$ClO$_2$: C, 56.15; H, 5.11%.

Found: C, 56.25; H, 5.07%.

EXAMPLE 16

Ethyl 6-Chloro-7-methoxy-c-4-hydroxy-r-2-methylchroman-4-acetate

To a solution of 4.9 ml (35 mmol) diisopropylamine in 40 ml dry tetrahydrofuran cooled to 0° C. was added 21.8 ml (35 mmol) 1.6M n-butyllithium in hexane. The reaction was cooled to −78° C. and 3.3 ml (35 mmol) ethyl acetate was added dropwise keeping the temperature below −70° C. To the solution was added 1.0 g (4.4 mmol) 6-chloro-7-methoxy-2-methylchroman-4-one in 40 ml tetrahydrofuran. The reaction was quenched by addition of 5 ml water, warmed to 23° C. and diluted with water. The layers were separated and the aqueous layer was washed with 2×100 ml diethyl ether. The combined organic layers were washed with 100 ml water and then brine, dried over magnesium sulfate and concentrated in vacuo to 1.4 g of crude product as an oil. Flash chromatography on 125 cc silica gel using chloroform as eluant gave 1.2 g (87%) product as an oil.
$^1$H-NMR(CDCl$_3$)delta(ppm): 7.43 (s, 1H), 6.35 (s, 1H), 4.20 (q, 2H), 4.16 (m, 1H), 3.83 (s, 3H), 2.70 (s, 2H), 2.43–1.63 (m, 2H), 1.38 (d, 3H), 1.27 (t, 3H).

EXAMPLE 17

6-Chloro-7-methoxy-c-4-hydroxy-r-2-methylchroman-4-acetic Acid

To a solution of 212 mg (3.8 mmol) potassium hydroxide and 30 ml ethanol was added 1.2 g (3.8 mmol) of the product of the preceding Example and the resulting solution stirred at 23° C. for 2 hours. The reaction was then poured into 200 ml water and washed with 2×100 ml diethyl ether. The aqueous layer was acidified with 6N hydrochloric acid and the aqueous layer extracted with 2×100 ml diethyl ether. These acidic ether washes were combined, washed with brine and concentrated in vacuo to give crude product as a foam, 910 mg (91%).
$^1$H-NMR(CDCl$_3$)delta(ppm): 7.32 (s, 1H), 7.17 (broad s, 1H), 6.27 (s, 1H), 4.17 (m, 1H), 3.78 (s, 3H), 2.82 (s, 2H), 2.48–1.60 (m, 2H), 1.38 (d, 3H). An analytical sample of the dicyclohexylamine salt was prepared by adding two equivalents of dicyclohexylamine to a diethyl ether solution of the free acid. On standing overnight crystals formed which were collected by filtration and dried to give the salt; m.p. 178°–180° C. with decomposition.
Analysis calculated for $C_{13}H_{15}ClO_5 \cdot C_{12}H_{23}N \cdot \frac{1}{4}H_2O$: C, 63.54; H, 8.21; N, 2.96%.
Found: C, 63.66; H, 7.98; N, 2.95%.

EXAMPLE 18

Ethyl 6-Fluoro-c-4-hydroxy-r-2-methylchroman-4-acetate

To a solution of 24.9 ml (0.178 mol) diisopropylamine in 350 ml dry tetrahydrofuran at 0° C. was added 84.8 ml (0.178 mol) 2.1M n-butyllithium in hexane. After stirring 1 hour at 0° C. the reaction was cooled to −78° C. and 17.4 ml (0.178 mol) ethyl acetate was added dropwise keeping the reaction temperature below −70° C. After stirring at −78° C. for 2.5 hours, 4 g (0.022 mol) 6-fluoro-2-methylchroman-4-one dissolved in 25 ml tetrahydrofuran was added keeping the temperature below −70° C. After stirring 1.5 hours at −78° C., the reaction was quenched with 15 ml water. The reaction was warmed to 23° C. and diluted with 200 ml water and 200 ml ether. The aqueous layer was separated and extracted with 2×150 ml diethyl ether. The combined organic layers were washed with 150 ml brine, dried over magnesium sulfate, and concentrated in vacuo to 8.1 g of an orange oil. This was purified by flash chromatography on 600 cc silica gel using hexane:diethyl ether (6:1) as eluant to give the product as a yellow oil, 5 g (85%).
$^1$H-NMR(CDCl$_3$)delta(ppm): 7.20–6.43 (m, 3H), 4.13 (q, 2H), 4.08 (m, 1H), 2.77 (s, 2H), 2.40–1.58 (m, 2H), 1.33 (d, 3H), 1.25 (t, 3H).

EXAMPLE 19

6-Fluoro-c-4-hydroxy-r-2-methylchroman-4-acetic Acid

A solution of 4.558 g (17 mmol) of title product of the preceding Example in 15 ml ethanol was added to a solution of 0.952 g (17 mmol) potassium hydroxide in 30 ml ethanol. The solution was stirred 4 hours at 23° C. and then the solvent removed in vacuo. The residue was taken up in water and washed with 2×100 ml methylene chloride. The aqueous was acidified with 17 ml 1N hydrochloric acid and extracted with 2×100 ml methylene chloride. The acidic methylene chloride extracts were combined, washed with 100 ml brine, dried over magnesium sulfate, and concentrated in vacuo to obtain 3.1 g (76%) of the title compound as a white solid; m.p. 122°–125° C.
$^1$H-NMR(CDCl$_3$)delta(ppm): 8.03 (broad s, 2H), 7.17 (m, 1H), 6.73 (m, 2H), 4.20 (m, 1H), 2.80 (s, 2H), 2.45–1.65 (m, 2H), 1.38 (d, 3H).
Analysis calculated for $C_{12}H_{13}FO_4$: C, 60.00; H, 5.45%.
Found: C, 59.76; H, 5.37%.

EXAMPLES 20–59

Variously Substituted Ethyl c-4-Hydroxy-r-2-(substituted)chroman-4-acetates

By the method of Examples 1, 4, 8, 10, 12, 14, 16 and 18, the appropriately substituted chroman-4-ones were converted to the following substituted ethyl c-4-hydroxy-r-2-(substituted)chroman-4-acetates [showing Example number, name of product, yield (eluant if chromatographed on silica gel) and physical properties-/analyses]:

20. Ethyl 6-fluoro-4-hydroxy-2,2-dimethylchroman-4-acetate; 96% white solid; tlc Rf 0.4 (1:1 diethyl ether:hexane).
21. Ethyl 6-fluoro-c-4-hydroxy-r-2-ethylchroman4-acetate; 77% (1:6 diethyl ether:hexane); oil; m/e 282(P+), 265(P-OH), 235, 195(P-CH$_2$CO$_2$C$_2$H$_5$), 177, 139.
22. Ethyl 6-fluoro-c-4-hydroxy-r-2-propylchroman-4-acetate; 38% (1:6 diethyl ether:hexane); oil; m/e 296(P+), 235, 209(P-CH$_2$COOC$_2$H$_5$), 191, 139.
23. Ethyl 6-fluoro-c-4-hydroxy-r-2-isopropylchroman-4-acetate; 96%; solid, m/e 296(P+), 235, 209, 191, 139.
24. Ethyl 6-fluoro-c-4-hydroxy-r-2-(t-butyl)chroman-4-acetate; 97%; solid; m/e 310(P+), 277, 263, 235, 223, 165, 139.
25. Ethyl 6-fluoro-c-4-hydroxy-r-2-phenylchroman-4-acetate; 33% (1:6 diethyl ether:hexane); oil; m/e 330(P+), 312(P-H$_2$O), 225, 180, 138.
26. Ethyl 6-fluoro-c-4-hydroxy-r-2,c-3-dimethylchroman-4-acetate; 71% (1:6 diethyl ether:hexane); m.p. 55°–58° C.; m/e 282(P+), 249, 195, 177, 139.
27. Ethyl 6-fluoro-c-4-hydroxy-r-2-(2-phenylethyl)-chroman-4-acetate; 71% (1:2 diethyl ether:hexane); oil.
28. Ethyl 6-fluoro-c-4-hydroxy-r-2-(3,4-dichlorobenzyl)chroman-4-acetate; 95% (toluene); oil; m/e 416, 414, 412(P+, 8%), 394(P-H$_2$O), 325, 307, 235(P+-H$_2$O-CH$_2$C$_6$H$_3$Cl$_2$, 100%), 207, 165 (47%), 139, 109.

29. Ethyl 6-fluoro-c-4-hydroxy-r-2-benzylchroman-4-acetate; 81% (toluene); m/e 344(P+, 24%), 257, 235 (100%), 165, 139, 91.
 1H-NMR(CDCl3)delta(ppm): 1.1 (t, 3H), 1.8–2.3 (m, 2H), 2.7 (t, 2H), 3.0 (t, 1H), 4.0 (q, 2H), 4.3 (s, 1H), 3.8–4.5 (broad m, 1H), 6.6–7.4 (m+aryl s, 8H).
30. Mixtures of 6-fluoro-c-4-hydroxy-r-2-ethyl-2-methylchroman-4-acetate and 6-fluoro-c-4-hydroxy-2-ethylr-2-methylchroman-4-acetate; (A) 35% of 1:2 mix of more polar to less polar diastereoisomer and (B) 26% of 2:1 mixture of more polar to less polar diastereoisomer, this parital separation by chromatography using 1:5 diethyl ether:hexane as eluant; both as oils.
31. Ethyl c-4-hydroxy-r-2-methylchroman-4-acetate; 56% (1:6-diethyl ether:hexane); oil; m/e 250(P+), 233(P-OH), 163(P-CH2CO2C2H5), 145, 121.
32. Ethyl c-4-hydroxy-r-2,6-dimethylchroman-4-acetate; 77% (1:6 diethyl ether:hexane); oil; m/e 264(P+), 247(P-OH), 177(P-CH2CO2C2H5), 159, 135.
33. Ethyl 6-bromo-c-4-hydroxy-r-2-methylchroman-4-acetate; 98% (1:5 diethyl ether:hexane); oil; m/e 330/328(P+), 243/241, 225, 199.
34. Ethyl 6-methanesulfonyl-c-4-hydroxy-r-2-methylchroman-4-acetate; 89%; oil.
35. Ethyl 6-benzoyl-c-4-hydroxy-r-2-methylchroman-4-acetate; 50% (1:6 diethyl ether:hexane); oil; m/e 354(P+), 337(P-OH), 267(P-CH2CO2C2H5), 105, 77; ir(CHCl3) 1720, 1650, 1610 cm−1.
36. Ethyl 6,8-dichloro-c-4-hydroxy-r-2-methylchroman-4-acetate; 79% (1:6 diethyl ether:hexane); oil; m/e 320/318(P+), 301(P-OH), 285, 271, 231, 213, 189.
37. Ethyl 6-chloro-c-4-hydroxy-r-2,8-dimethyl-chroman-4-acetate; 88%; m/e 298(P+), 281(P-OH), 211, 169.
38. Ethyl 6-bromo-8-chloro-c-4-hydroxy-r-2-methylchroman-4-acetate; 91%; oil.
39A. Ethyl 6,7-dichloro-c-4-hydroxy-r-2-methylchroman-4-acetate; 37%; identical with product of Example 4; and ethyl 5,6-dichloro-c-4-hydroxy-r-2-methylchroman-4-acetate; 51%; oil.
 1H-NMR(CDCl3)delta(ppm): 7.10 (d, 1H), 6.57 (d, 1H), 4.13 (q, 2H), 4.13 (m, 1H), 3.05 (q, 2H), 2.57–1.70 (m, 2H), 1.38 (d, 3H), 1.27 (t, 3H); from approximately 1:1 6,7- and 5,6-dichloro-2-methylchroman-4-one; present products separated and purified by chromatography on silica gel with 1:4:1 diethyl ether:hexane:chloroform as eluant.
39B. Ethyl 5,6-dichloro-c-4-hydroxy-r-2-methylchroman-4-acetate; 25% (1:4:1 diethyl ether:hexane:chloroform); oil; 1H-NMR identical to that of Example 39A.
40. Ethyl 6-nitro-c-4-hydroxy-r-2,5-dimethylchroman-4-acetate; 31% (2:1 hexane:diethyl ether as eluant); oil; tlc Rf 0.3 (1:1 diethyl ether:hexane).
41. Ethyl 6-chloro-c-4-hydroxy-r-2,7-dimethyl-chroman-4-acetate; 92%; oil; m/e 300/298(P+), 311, 281, 216, 193, 169.
 1H-NMR(CDCl3)delta(ppm): 7.37 (s, 1H), 6.60 (s, 1H), 4.20 (q, 2H), 4.20 (m, 1H), 2.80 (s, 2H), 2.30 (s, 3H), 2.43–1.60 (m, 2H), 1.40 (d, 3H), 1.30 (t, 3H).
42. Ethyl 7-chloro-6-nitro-c-4-hydroxy-r-2-methylchroman-4-acetate; 71% (contaminated with about 33% 7-chloro-8-nitro isomer by 1H-NMR; oil.
 1H-NMR(CDCl3)delta(ppm): 8.17 (s, 0.66H), 7.48 (d, 0.33H), 6.97 (d, 0.33H), 6.90 (s, 0.66H), 4.20 (q, 2H), 2.80 (s, 0.66×2H), 1.45 (d, 0.66×3H), 1.41 (d, 0.33×3H), 1.27 (t, 3H).
43. Ethyl 6-nitro-c-4-hydroxy-r-2,7-dimethylchroman-4-one; 17% (by 1H-NMR, contaminated with 25% of the 5-methyl-6-nitro isomer after chromatography; 2:1 hexane:diethyl ether); oil.
44. Ethyl 7-chloro-c-4-hydroxy-r-2-methylchroman-4-one; 35% (1:8:1 diethyl ether:hexane:chloroform).
45. Ethyl 6-chloro-c-4-hydroxy-r-2-methyl-3,4-dihydro2H-benzo[h]chromen-4-acetate; 62% (2:1 hexane:ethyl acetate); oil.
46. Ethyl 5,8-dichloro-c-4-hydroxy-r-2-methylchroman-4-acetate; 92%; oil.
47. Ethyl 8-chloro-c-4-hydroxy-r-2-methylchroman-4-acetate; 88%; m/e 284/286(P+, 3:1), 267, 251, 237, 221, 197, 179, 155, 144.
48. Ethyl 7,8-dichloro-c-4-hydroxy-r-2-methylchroman-4-acetate; 84%; oil.
49. Ethyl 6-nitro-7-fluoro-c-4-hydroxy-r-2-methylchroman-4-acetate; 100% (assumed, entire product used directly in next step).
50. Ethyl 6-nitro-4-hydroxy-2,2-dimethylchroman-4-acetate; 100%; oil; m/e 309(P+), 292, 276, 253, 222, 207, 166, 120; tlc Rf 0.2 (1:1 diethyl ether:hexane).
51. Ethyl 6,7-dichloro-4-hydroxy-2,2-dimethylchroman-4-acetate; 56% (4:1 hexane:diethyl ether); oil.
52. Ethyl 5,6-dichloro-4-hydroxy-2,2-dimethylchroman-4-acetate; 100% (assumed, entire product used directly in next step).
53. Ethyl 7-fluoro-c-4-hydroxy-r-2-methylchroman-4-acetate; 88%.
54. Ethyl 6,7-difluoro-c-4-hydroxy-r-2-methylchroman-4-acetate; 86%.
55. Ethyl 6-cyano-7-fluoro-c-4-hydroxy-r-2-methylchroman-4-acetate; 100% (assumed, entire product used directly in next step).
56. Ethyl 6-chloro-7-bromo-c-4-hydroxy-r-2-methylchroman-4-acetate; 89%.
57. Ethyl 6-fluoro-7-bromo-c-4-hydroxy-r-2-methylchroman-4-acetate; 51%.
58. Ethyl 5-bromo-6-fluoro-c-4-hydroxy-r-2-methylchroman-4-acetate; 24%.
59. Ethyl 6-chloro-7-ethyl-c-4-hydroxy-r-2-methylchroman-4-acetate; 92%.

EXAMPLES 60–99

Variously Substituted
c-4-Hydroxy-r-2-(substituted)chroman-4-acetic Acids

By the method of Examples 2, 5, 9, 11, 13, 15 and 19, the esters of preceding Examples 20–48 were converted to the following substituted c-4-hydroxy-r-2-(substituted)chroman-4-acetic acids (showing Example number, name of product, yield, and physical properties/analyses):

60. 6-Fluoro-4-hydroxy-2,2-dimethylchroman-4-acetic acid; 64%; m.p. 108°–111° C.; m/e 254(P+), 221, 195, 180.
Analysis calculated for $C_{13}H_{15}FO_4$: C, 61.41; H, 5.95%. Found: C, 61.33; H, 5.67%.
61. 6-Fluoro-c-4-hydroxy-r-2-ethylchroman-4-acetic acid; 73%; m.p. 89°–91° C.; m/e 254(P+), 207, 195(P-CH2COOH), 139.
Analysis calculated for $C_{13}H_{15}FO_4$: C, 61.41; H, 5.95%. Found: C, 61.20; H, 5.81%.
62. 6-Fluoro-c-4-hydroxy-r-2-propylchroman-4-acetic acid; 70%; m/e 268(P+), 209(P-CH2COOH), 139.
Analysis calculated for $C_{14}H_{17}FO_4$: C, 62.67; H, 6.39%.

Found: C, 62.83; H, 6.35%.

63. 6-Fluoro-c-4-hydroxy-r-2-isopropylchroman-4-acetic acid; 73%; m.p. 119°–122° C.; m/e 268(P+), 209(P-CH₂COOH), 191, 181, 165, 139.

Analysis calculated for $C_{14}H_{17}FO_4$: C, 62.67; H, 6.39%.
Found: C, 62.71; H, 6.41%.

64. 6-Fluoro-c-4-hydroxy-r-2-(t-butyl)chroman-4-acetic acid; 82%; m.p. 123°–125° C.; m/e 282(P+), 249, 223(P-CH₂COOH), 207, 165, 139.

Analysis calculated for $C_{15}H_{19}FO_4$: C, 63.82; H, 6.78%.
Found: C, 64.15; H, 6.83%.

65. 6-Fluoro-c-4-hydroxy-r-2-phenylchroman-4-acetic acid; 57%; m.p. 140°–143° C.; m/e 302(P+), 284(P-H₂O), 243, 225(P-C₆H₅), 180, 138.

Analysis calculated for $C_{17}H_{15}FO_4$: C, 67.54; H, 5.00%.
Found: C, 67.12; H, 4.72%.

66. 6-Fluoro-c-4-hydroxy-r-2,c-3-dimethylchroman4-acetic acid; 67%; m.p. 149°–151° C.; m/e 254(P+), 221, 195, 180, 139.

Analysis calculated for $C_{13}H_{15}FO_4$: C, 61.41; H, 5.95%.
Found: C, 61.38; H, 5.95%.

67. 6-Fluoro-c-4-hydroxy-r-2-(2-phenylethyl)chroman-4-acetic acid; 84%; oil.

Exact mass calculated: 330.1267.
Found: 330.1245.

68. Dicyclohexylammonium 6-fluoro-c-4-hydroxy-r-2-(3,4-dichlorobenzyl)chroman-4-acetic acid; 51%; m.p. 168°–179° C. (with decomposition); m/e 386, 384(P+, 42%), 366 (P+-H₂O), 325(P+-CH₂COOH), 207 (100%), 181, 165, 159, 138.

Analysis calculated for $C_{18}H_{15}O_4Cl_2F \cdot C_{12}H_{23}N$: C, 63.60; H, 6.76; N, 2.47%.
Found: C, 63.52; H, 6.77; N, 2.36%.

69. Dicyclohexylammonium 6-fluoro-c-4-hydroxy-r-2-benzylchroman-4-acetic acid; 63%; m.p. 166°–167° C. (decomposition); m/e 316(P+, 4%), 207 (13%), 181 (41%), 152 (13%), 138 (100%), 100, 56, 55, 44.

Analysis calculated for $C_{18}H_{17}O_4F \cdot C_{12}H_{23}N$: C, 72.40; H, 8.10; N, 2.82%.
Found: C, 72.49; H, 7.98; N, 2.80%.

70A. 1:2 Mixture consisting of 6-fluoro-c-4-hydroxy-r-2-ethyl-2-methylchroman-4-acetic acid and 6-fluoro-c-4-hydroxy-2-ethyl-r-2-methylchroman-4-acetic acid from mixture (A) of Example 30; 42%; m.p. 125°–128° C.; m/e 268(P+), 235, 221, 209, 199, 180, 139.

Analysis calculated for $C_{14}H_{17}FO_4$: C, 62.67; H, 6.39%.
Found: C, 62.54; H, 6.25%.

70B. 2:1 Mixture consisting of 6-fluoro-c-4-hydroxy-r-2-ethyl-2-methylchroman-4-acetic acid and 6-fluoro-c-4-hydroxy-2-ethyl-r-2-methylchroman-4-acetic acid from mixture (B) of Example 30; 45%; m.p. 120°–122° C.; m/e 268(P+), 235, 221, 199, 180, 139.

Analysis calculated for $C_{14}H_{17}FO_4$: C, 62.67; H, 6.39%.
Found: C, 62.48; H, 6.28%.

71. c-4-Hydroxy-r-2-methylchroman-4-acetic acid; 71%; m.p. 99°–101° C. (softens at 95° C.); m/e 222(P+), 163(P-CH₂COOH), 145, 121.

Analysis calculated for $C_{12}H_{14}O_4$: C, 64.85; H, 6.35%.
Found: C, 64.79; H, 6.43%.

72. c-4-Hydroxy-r-2,6-dimethylchroman-4-acetic acid; 71%; m/e 236(P+), 177(P-CH₂COOH), 159, 135.

Analysis calculated for $C_{13}H_{16}O_4$: C, 66.08; H, 6.83%.
Found: C, 66.31; H, 6.70%.

73. 6-Bromo-c-4-hydroxy-r-2-methylchroman-4-acetic acid; 69%; m.p. 135°–137° C.; m/e 302/300(P+, 1:1), 243/241, 201/199.

Analysis calculated for $C_{12}H_{13}BrO_4$: C, 47.86; H, 4.35%.
Found: C, 47.85; H, 4.25%.

74. 6-Methanesulfonyl-c-4-hydroxy-r-2-methylchroman-4-acetic acid; 43%; m.p. 164°–167° C.

Analysis calculated for $C_{13}H_{16}O_6S$: C, 51.99; H, 5.37%.
Found: C, 51.73; H, 5.32%.

75. 6-Benzoyl-c-4-hydroxy-r-2-methylchroman-4-acetic acid; 49%; m.p. 159°–163° C.; m/e 326(P+), 309(P-OH), 267(P-CH₂COOH), 249, 189, 145, 105, 77.

Analysis calculated for $C_{19}H_{18}O_5$: C, 69.93; H, 5.56%.
Found: C, 69.99; H, 5.73%.

76. 6,8-Dichloro-c-4-hydroxy-r-2-methylchroman-4-acetic acid; 68%; m.p. 143°–145° C.; m/e 290/292(P+), 273(P-OH), 257, 231(P-CH₂COOH), 213, 189.

Analysis calculated for $C_{12}H_{12}Cl_2O_4$: C, 49.50; H, 4.15%.
Found: C, 49.50; H, 4.13%.

77. 6-Chloro-c-4-hydroxy-r-2,8-dimethylchroman-4-acetic acid; 64%; m.p. 118°–120° C.; m/e 270(P+), 237, 211(P-CH₂COOH), 169.

Analysis calculated for $C_{13}H_{15}ClO_4$: C, 57.61; H, 5.59%.
Found: C, 57.67; H, 5.47%.

78. 6-Bromo-8-chloro-c-4-hydroxy-r-2-methylchroman-4-acetic acid; 74%; m.p. 168°–171° C. (with decomposition).

Analysis calculated for $C_{12}H_{12}O_4BrCl$: C, 42.94; H, 3.60%.
Found: C, 43.13; H, 3.41%.

79. 5,6-Dichloro-c-4-hydroxy-r-2-methylchroman-4-acetic acid; 65%; m.p. 144°–147° C.

¹H-NMR(DMSO)delta(ppm): 7.44 (d, 1H), 6.83 (d, 1H), 4.41 (m, 1H), 3.04 (q, 2H), 2.64 (d, 1H), 1.83 (t, 1H), 1.34 (d, 3H).

Analysis calculated for $C_{12}H_{12}Cl_2O_4$: C, 49.50; H, 4.15%.
Found: C, 49.24; H, 4.25%.

80. 6-Nitro-c-4-hydroxy-r-2,5-dimethylchroman-4-acetic acid; 52%; m.p. 155°–158° C.

Analysis calculated for $C_{13}H_{15}O_6N$: C, 55.51; H, 5.38; N, 4.98%.
Found: C, 55.87; H, 5.25; N, 5.07%.

81. 6-Chloro-c-4-hydroxy-r-2,7-dimethylchroman-4-acetic acid; 66%; m.p. 134°–136° C.

Analysis calculated for $C_{13}H_{15}ClO_4$: C, 57.67; H, 5.59%.
Found: C, 57.95; H, 5.64%.

¹H-NMR(CDCl₃)delta(ppm): 7.43 (s, 1H), 7.27 (broad s, 2H), 6.67 (s, 1H), 4.20 (m, 1H), 2.93 (s, 2H), 2.57–1.57 (m, 2H), 2.33 (s, 3H), 1.42 (d, 3H).

82. 7-Chloro-6-nitro-c-4-hydroxy-r-2-methylchroman-4-acetic acid; 34% (separated from 7-chloro-8-nitro isomer by slurry in ethanol); m.p. 133°–137° C.

¹H-NMR(20:1 CDCl₃:DMSO)delta(ppm): 8.23 (s, 1H), 7.97 (broad s, 1H), 6.88 (s, 1H), 4.38 (m, 1H), 2.78 (s, 2H), 2.57–1.67 (m, 2H).

Analysis calculated for $C_{12}H_{12}ClNO_6$: C, 47.77; H, 4.01; N, 4.64%.
Found: C, 47.80; H, 3.99; N, 4.59%.

83. 6-Nitro-c-4-hydroxy-r-2,7-dimethylchroman-4-acetic acid; 30%; m.p. 95°–100° C.

Analysis calculated for $C_{13}H_{15}NO_6$: C, 55.51; H, 5.38; N, 4.98%.
Found: C, 55.47; H, 5.42; N, 4.82%.

84. 7-Chloro-c-4-hydroxy-r-2-methylchroman-4-acetic acid; 60%; m.p. 147°–150° C.

Analysis calculated for $C_{12}H_{13}O_4Cl$: C, 56.15; H, 5.11%.
Found: C, 56.15; H, 5.17%.

85. 6-Chloro-c-4-hydroxy-r-2-methyl-3,4-dihydro-2H-benzo[h]chromen-4-acetic acid; 64%; m.p. 143°–145° C.
Analysis calculated for $C_{16}H_{15}O_4Cl$: C, 62.65; H, 4.93%.
Found: C, 62.71; H, 4.92%.

86. 5,8-Dichloro-c-4-hydroxy-r-2-methylchroman-4-acetic acid; 71%; m.p. 104°–110° C.
Analysis calculated for $C_{12}H_{12}O_4Cl_2$: C, 49.50; H, 4.15%.
Found: C, 49.41; H, 4.06%.

87. 8-Chloro-c-4-hydroxy-r-2-methylchroman-4-acetic acid; 58%; m.p. 84°–86° C.
Analysis calculated for $C_{12}H_{13}O_4Cl$: C, 56.16; H, 5.10%.
Found: C, 56.16; H, 5.11%.

88. 7,8-Dichloro-c-4-hydroxy-r-2-methylchroman4-acetic acid; 69%; m.p. 126°–131° C.
Analysis calculated for $C_{12}H_{12}O_4Cl_2$: C, 49.50; H, 4.15%.
Found: C, 49.58; H, 4.07%.

89. 6-Nitro-7-fluoro-c-4-hydroxy-r-2-methylchroman-4-acetic acid; 42%; m.p. 133°–137° C.
Analysis calculated for $C_{12}H_{12}FNO_6$: C, 50.53; H, 4.24; N, 4.91%.
Found: C, 50.23; H, 4.30; N, 5.08%.

90. 6-Nitro-4-hydroxy-2,2-dimethylchroman-4-acetic acid; 64%; m/e 281(P+), 264, 248, 222, 207, 166, 120, 83.
Analysis calculated for $C_{13}H_{15}NO_6$: C, 55.51; H, 5.38; N, 4.98%.
Found: C, 55.48; H, 5.27; N, 4.93%.

91. 6,7-Dichloro-4-hydroxy-2,2-dimethylchroman-4-acetic acid; 76%; m.p. 147°–149° C. (decomposition).
Analysis calculated for $C_{13}H_{14}O_4Cl_2$: C, 51.16; H, 4.62%.
Found: C, 51.47; H, 4.76%.

92. 5,6-Dichloro-4-hydroxy-2,2-dimethylchroman-4-acetic acid; 22%; m.p. 152°–155° C.
Analysis calculated for $C_{13}H_{14}O_4Cl_2$: C, 51.16; H, 4.62%.
Found: C, 51.09; H, 4.57%.

93. 7-Fluoro-c-4-hydroxy-r-2-methylchroman-4-acetic acid; 53%; m.p. 116°–119° C.
Analysis calculated for $C_{12}H_{13}FO_4$: C, 60.00; H, 5.45%.
Found: C, 59.84; H, 5.33%.

94. 6,7-Difluoro-c-4-hydroxy-r-2-methylchroman-4-acetic acid; 62%; m.p. 128°–131° C.
Analysis calculated for $C_{12}H_{12}F_2O_4$: C, 55.81; H, 4.68%.
Found: C, 55.88; H, 4.70%.

95. 6-Cyano-7-fluoro-c-4-hydroxy-r-2-methylchroman-4-acetic acid; 54%; m.p. 142°–144° C.
$^1$H-NMR(DMSO)delta(ppm): 7.87 (d, 1H, J=7 Hz), 6.98 (d, 1H, J=12 Hz), 4.52 (m, 1H), 2.68 (d, 2H), 2.50 (s, 2H), 1.73 (t, 1H), 1.35 (d, 3H).

96. 6-Chloro-7-bromo-c-4-hydroxy-r-2-methylchroman-4-acetic acid; 67%; m.p. 154°–157° C.
Analysis calculated for $C_{12}H_{12}BrClO_4$: C, 42.95; H, 3.60%.
Found: C, 43.19; H, 3.60%.

97. 6-Fluoro-7-bromo-c-4-hydroxy-r-2-methylchroman-4-acetic acid; 63%; m.p. 151°–154° C.
Analysis calculated for $C_{12}H_{12}BrFO_4$: C, 45.16; H, 3.79%.
Found: C, 45.36; H, 3.79%.

98. 5-Bromo-6-fluoro-c-4-hydroxy-r-2-methylchroman-4-acetic acid; 39%; m.p. 121°–124° C.
Analysis calculated for $C_{12}H_{12}BrFO_4$: C, 45.16; H, 3.79%.
Found: C, 44.96; H, 3.75%.

99. 6-Chloro-7-ethyl-c-4-hydroxy-r-2-methylchroman-4-acetic acid; m.p. 99°–103° C.
Analysis calculated for $C_{14}H_{17}ClO_4$: C, 59.05; H, 6.02%.
Found: C, 59.06; H, 6.16%.

EXAMPLE 100

2R,4R-6,7-Dichloro-4-hydroxy2-methyl-4-acetic Acid

Under nitrogen, a solution of 5.1 ml (3.6 g, 0.036 mol) of isopropylamine in 22 ml tetrahydrofuran was cooled to −62° C. Maintaining a temperature of −56° to −60° C., 22.2 ml of 1.6M n-butyl lithium in hexane (0.036 mol) was added over 50 minutes, and the mixture further cooled to −78° C. Ethyl acetate (3.5 ml, 0.036 mol) was added dropwise over 80 minutes, maintaining the temperature at −70° to −73° C. and the mixture cooled and stirred at −78° C. for 30 minutes. While maintaining a temperature of −68° to −74° C., a solution of 7.5 g of 2R-6,7-Dichloro-2-methylchroman-4-one (0.032 mol) in 14 ml tetrahydrofuran was added dropwise over 2 hours, followed by 5 ml of tetrahydrofuran for rinse. After 4 hours at about −70° C., 1.3 ml of water was added over 3 minutes during which time the temperature rose to −61° C. The temperature was allowed to rise to about 0° C. over 2 hours, 7.3 ml additional water was added, and the mixture was warmed to ambient temperature (26° C.), held for 3 hours, stripped in vacuo to a volume of 20 ml and diluted with 40 ml of water and extracted 2×20 ml methylene chloride. The organic layers were combined and back-washed with 20 ml of water. The original aqueous layer and water backwash were combined, cooled to 10° C., layered with 20 ml methylene chloride and the pH adjusted from 12.4 to 4.5 with concentrated hydrochloric acid. The organic layer was separated, the aqueous layer extracted with a further 20 ml methylene chloride, which was combined with the first organic layer, back-washed with 40 ml water and stripped to an oil (9.9 g). The oil was taken up in 20 ml isopropyl ether and carefully (foaming!) extracted into a total of 30 ml of 10% (w/v) sodium bicarbonate. The bicarbonate layers were combined, washed 2×10 ml isopropyl ether and 3×10 ml methylene chloride, diluted to 75 ml with water, cooled to 10° C., layered with 75 ml methylene chloride, and the pH adjusted to 2.0 with concentrated hydrochloric acid. The aqueous layer was separated and washed with 20 ml methylene chloride. The two organic layers were combined, dried over magnesium sulfate and stripped in vacuo to an oil (9.5 g) which was crystallized from 12 ml stirring methylene chloride by the slow addition of 20 ml hexane at ambient temperature and recovered by filtration after granulating for 1 hour and cooling to 5° C., 6.0 g, identical with the product of Example 7.

EXAMPLE 101

Ethyl 6-Fluoro-c-4-hydroxy-r-2-methylchroman-4-acetate

To a solution of 180.2 mg (1 mmol) 6-fluoro-2-methylchroman-4-one and 0.17 ml (1.5 mmol) ethylbromoacetate in 1 ml benzene at 23° C. was added 98 mg of zinc metal (prepared by filing mossy zinc). A crystal of iodine was added to initiate reaction. Gentle warming resulted in a sudden bubbling and exotherm. The reaction was allowed to cool to 23° C., and poured into 20 ml 1N hydrochloric acid and 20 ml diethyl ether. The organic layers were separated, successively washed with 10 ml 1N hydrochloric acid, 10 ml water and 10 ml brine, dried over magnesium sulfate and concentrated in vacuo to give the product, 251 mg (95%) as a yellow oil having physical properties identical with the properties of Example 18 above.

EXAMPLE 102

Allyl 6,7-Dichloro-c-4-hydroxy-r2-methylchroman-4-acetate

To a solution of 2.7 ml (19 mmol) diisopropylamine in 30 ml tetrahydrofuran was added 7.3 ml (19 mmol) of 2.6M n-butyl lithium in hexane keeping the reaction temperature below 5° C. The reaction was cooled to −78° C. and 2.05 ml (19 mmol) allyl acetate and then 4.0 g (17.3 mmol) of 6,7-dichloro-2-methylchroman-4-one in 10 ml tetrahydrofuran were added, keeping the temperature below −65° C. The reaction was quenched with 5 ml water, diluted with 30 ml diethyl ether, and allowed to warm to 10° C. The layers were separated and the aqueous was washed with 20 ml diethyl ether. The combined organic layers were washed with 20 ml brine, dried over magnesium sulfate, and concentrated in vacuo to give 6.1 g of product as an oil.

$^1$H-NMR(CDCl$_3$)delta(ppm): 7.50 (s, 1H), 6.85 (s, 1H), 5.43–5.08 (m, 3H), 4.62 (m, 2H), 4.16 (m, 1H), 2.82 (s, 2H), 2.13 (m, 2H), 1.37 (d, 3H).

EXAMPLE 103

6,7-Dichloro-c-4-hydroxy-r-2-methylchroman-4-acetic Acid

To a solution of 319 mg (1 mmol) of title product of the preceding Example in 3 ml methylene chloride was added 0.79 ml (1.1 mol) of a 1.39M solution of sodium 2-ethylhexanoate in ethyl acetate, 25 mg of tetrakis(triphenylphosphine)palladium and 25 mg triphenylphosphine. The reaction was stirred at 23° C. for 1 hour, then diluted with 30 ml water and 30 ml diethyl ether. The layers were separated, the aqueous layer washed with 2×20 ml diethyl ether, acidified with 1 ml 1N hydrochloric acid and extracted with 2×20 ml diethyl ether. The latter were combined, dried over magnesium sulfate and concentrated in vacuo to give 222 mg of crude solid. This was triturated with hexane and the resultant white solid, 137 mg (47%), was collected by filtration; m.p. 160°–162° C.

$^1$H-NMR(DMSO-d$_6$)delta(ppm): 7.57 (s, 1H), 6.96 (s, 1H), 4.38 (m, 1H), 2.64 (q, 2H), 2.50 (d, 1H), 1.69 (t, 1H), 1.30 (d, 3H); substantially identical with the product of Example 5, above.

EXAMPLE 104

Ethyl 6,7-Dichloro-c-4-hydroxy-r-2-(trifluoromethyl)chroman-4-acetate

To a solution of 0.11 ml (0.81 mmol) diisopropylamine in 4 ml tetrahydrofuran was added 0.31 ml (0.81 mmol) of 2.6M n-butyllithium in hexane keeping the reaction temperature below 5° C. The reaction was cooled to −78° C. and 0.08 ml (0.81 mmol) of ethyl acetate was added keeping the reaction temperature below −65° C. A solution of 0.211 g (0.74 mmol) of 6,7-dichloro-2-(trifluoromethyl)chroman-4-one in 2 ml tetrahydrofuran was added keeping the reaction temperature below 65° C. The reaction was quenched with water, diluted with diethyl ether and warmed to −10° C. Additional water was added and the layers were separated. The aqueous layer was extracted with 2×25 ml diethyl ether and the combined ether layers were washed with 25 ml brine, dried over magnesium sulfate and concentrated in vacuo to give 251 mg of solids which NMR analysis indicated an 80:20 mixture of product to starting chromanone.

$^1$H-NMR(CDCl$_3$)delta(ppm): 7.50 (s, 1H), 6.97 (s, 1H), 4.50 (m, 1H), 4.20 (q, 2H), 2.76 (s, 2H), 2.43–1.63 (m, 2H), 1.27 (t, 3H).

EXAMPLE 105

6,7-Dichloro-c-4-hydroxy-r-2-(trifluoromethyl)chroman-4-acetic Acid

To a solution of 248 mg of crude title product of the preceding Example in 3 ml ethanol was added 41 mg (0.73 mmol) potassium hydroxide. The reaction was stirred at 23° C. for 4 hours and then concentrated in vacuo at 23° C. The residue was partitioned between diethyl ether and water. The aqueous was washed with diethyl ether (2×25 ml) and then was acidified with 1 ml 1N hydrochloric acid and extracted with 2×25 ml diethyl ether. The latter ether extracts were combined, washed with 25 ml brine, dried over magnesium sulfate and concentrated in vacuo to give 12 mg (5.3%) of the product as a gum.

$^1$H-NMR(DMSO-d$_6$)delta(ppm): 7.65 (s, 1H), 7.21 (s, 1H), 5.15 (m, 1H), 2.85 (m, 1H), 2.70 (q, 2H), 1.92 (t, 1H).

Exact Mass: Calculated for $C_{12}H_9O_4Cl^{35}Cl^{37}F_3$: m/e 345.9800.

Found: m/e 345.9840.

EXAMPLE 106

Allyl 6,7-Dichloro-c-4-hydroxy-r-2-(trifluoromethyl)chroman-4-acetate

To a solution of 0.82 ml (5.85 mmol) diisopropylamine in 13 ml tetrahydrofuran was added 2.25 ml (15.85 mmol) 2.6M n-butyllithium in hexane, keeping the reaction temperature below 5° C. The reaction was cooled to −78° C. and 0.63 ml (5.85 mmol) allyl acetate was added keeping the reaction temperature below −65° C. A solution of 1.516 g (5.32 mol) 6,7-dichloro-2-trifluoromethyl-4-chromanone in 4 ml tetrahydrofuran was added, keeping the reaction temperature below −65° C. The reaction was quenched with 1.5 ml water, then diluted with 15 ml diethyl ether and warmed to 10° C. Water (15 ml) and diethyl ether (15 ml) were added and the aqueous layer separated and extracted with 15 ml fresh diethyl ether. The combined ether solutions were washed with brine, dried over magnesium sulfate and concentrated in vacuo to yield 1.99 g (97%) of title product as a yellow syrup.

$^1$H-NMR(CDCl$_3$)delta(ppm): 7.53 (s, 1H), 7.00 (s, 1H), 6.12–5.07 (m, 3H), 4.63 (d, 2H), 4.33 (m, 1H), 2.83 (s, 2H), 2.63–1.92 (m, 2H).

EXAMPLE 107

6,7-Dichloro-c-4-hydroxy-r-2-(trifluoromethyl)chroman-4-acetic Acid

To a solution of 1.841 g (4.78 mmol) of the product of the preceding Example in 18 ml methylene chloride was added 4.2 ml (5.26 mmol) of 1.25M sodium 2-ethylhexanoate in ethyl acetate, 120 mg (0.0104 mmol) tetrakis(triphenylphosphine)palladium, and 120 mg (0.0457 mmol) triphenylphosphine. The reaction was stirred at 23° C. for 1 hour, diluted with water, washed with diethyl ether, acidified with 7 ml 1N hydrochloric acid, and extracted with diethyl ether. The ether extract was washed with brine, dried over magnesium sulfate and concentrated in vacuo to give 741 mg of a colorless oil. On dilution with hexane, crystallization occurred. Title product, 190 mg (13.7%), was isolated in the form of white crystals; m.p. 130°–135° C.

Analysis calculated for $C_{12}H_9Cl_2F_3O_4$: C, 41.76; H, 2.63%.

Found: C, 42.01; H, 2.63%.

EXAMPLE 108

Ethyl 6,7-Dichloro-c-4-hydroxy-r-2-methyl-3,4-dihydro-2H-1-thianaphthalene-4-acetate By the method of Examples 1, 4, 8, 10, 12, 14, 16 and 18, without chromatography, 2-methyl-2H,3H-1-thianaphthalen-4-one (0.50 g, 2.02 mmol) was converted to title product, 0.47 g, tlc Rf 0.12 (5:1 hexane:ethyl acetate).

EXAMPLE 109

6,7-Dichloro-c-4-hydroxy-r-2-methyl-3,4-dihydro-2H-1-thianaphthalene-4-acetic Acid By the method of Examples 2, 5, 9, 11, 13, 15, 17 and 19, the product of the preceding Example was converted to present title product, flash chromatographed on silica gel with ethyl acetate as eluant, crystallized from $CHCl_3$, 0.12 g; m.p. 156°–157° C.

$^1$H-NMR(CDCl$_3$)delta(ppm): 7.9 (s, 1H), 7.2 (s, 1H), 3.5 (m, 1H), 2.9–2.6 (q, 2H), 2.4–2.5 (d, 1H), 1.8–1.9 (t, 1H), 1.4 (d, 3H).

EXAMPLE 110

Ethyl 6,7-Dichloro-c-4-hydroxy-r-2-methyl-3,4-dihydro-2H-1-thianaphthalene-4-acetate 1-Oxide The product of Example 108 (0.38 g, 1.1 mmol) was dissolved in 60 ml $CH_2Cl_2$, stirred and cooled to 0°–5° C. m-Chloroperbenzoic acid (0.19 g, 1.1 mmol) in 15 ml $CH_2Cl_2$ was added dropwise over 15 minutes. After 1 hour at 0° C., the reaction mixture was washed 1×60 ml saturated $NaHCO_3$, 1×60 ml water and 1×60 ml brine, dried over $MgSO_4$ and stripped in vacuo to yield title product as an oil, 0.37 g.

EXAMPLE 111

6,7-Dichloro-c-4-hydroxy-r-2-methyl-3,4-dihydro-2H-1-trianaphthalene-4-acetic Acid 1-Oxide By the method of Example 109, the product of the preceding Example (0.37 g, 1.05 mmol) was converted to present chromatographed product, 0.18 g; m.p. 80°–82° C. $^1$H-NMR(CDCl$_3$)delta(ppm): 7.9 (s, 1H), 7.7 (s, 1H), 3.1 (m, 1H), 2.8–2.1 (m, 4H), 1.6 (d, 3H), 1.5 (d, 3H).

EXAMPLE 112

Ethyl 6,7-Dichloro-c-4-hydroxy-r-2-methyl-3,4-dihydro-2H-1-thianaphthalene-4-acetate 1,1-Dioxide The product of Example 108 (0.50 g, 1.49 mmol) was dissolved in 10 ml $CH_2Cl_2$ and m-chloroperbenzoic acid (0.8 g, 4.5 mmol) added. After stirring 16 hours at ambient temperature, title product was isolated as in Example 108, 0.6 g of oil.

EXAMPLE 113

6,7-Dichloro-c-4-hydroxy-r-2-methyl-3,4-dihydro-2H-1-thianaphthalene-4-acetic Acid 1,1-Dioxide By the method of Example 109, without chromatography, the product of the preceding Example (0.6 g, 1.6 mmol) was converted to present title product, purified by repulping crude solids in minimal $CH_2Cl_2$, 0.23 g.

Analysis calculated for $C_{12}H_{12}Cl_2SO_5$: C, 42.49; H, 3.57%.

Found: C, 42.11; H, 3.59%.

EXAMPLE 114

Ethyl 6-Fluoro-c-4-hydroxy-r-2-methyl-3,4-dihydro-2H-1-thianaphthalene-4-acetate By the method of Example 108, 6-fluoro-2-methyl-2H,3H-1-thianaphthalene-4-one (5.0 g, 0.025 mol) was converted to title product as an oil, 6.2 g; m/e 154.9, 179 (100%), 197, 284.

EXAMPLE 115

6-Fluoro-c-4-hydroxy-r-2-methyl-3,4-dihydro-2H-1-thianaphthalene-4-acetic Acid

By the method of Example 109, using 1:1 hexane:ethyl acetate as eluant on chromatography, the product of the preceding Example (4 g) was converted to present title product, 1.12 g, recrystallized from ether/hexane, 0.72 g.

$^1$H-NMR(CDCl$_3$)delta(ppm): 7.4 (d, 1H), 7.05 (m, 1H), 6.9 (t, 1H), all aromatics showing fine coupling to fluorine, 3.5 (m, 1H), 2.9–3.0 (q, 2H), 2.5 (dd, 1H), 1.8–1.9 (t, 1H), 1.4 (d, 3H).

EXAMPLE 116

Ethyl 6-Fluoro-c-4-hydroxy-r-2-methyl-3,4-dihydro-2H-1-thianaphthalene-4-acetate 1-Oxide By the method of Example 110, the product of Example 112 (2.96 g, 10.4 mmol) was converted to present title product, 1.5 g.

EXAMPLE 117

6-Fluoro-c-4-hydroxy-r-2-methyl-3,4-dihydro-2H-1-thianaphthalene-4-acetic Acid 1-Oxide By the method of Example 109, without chromatography, the product of the preceding Example (2.0 g, 6.7 mmol) was converted to present title product initially isolated as a foam which was crystallized from $CH_2Cl_2$, 0.23 g, a mixture of isomers, separated by further recrystallization from $CH_2Cl_2$ to yield one isomer as first crop, 38 mg, and the other isomer as second crop, 102 mg.

EXAMPLE 118

Ethyl 6-Fluoro-c-4-hydroxy-r-2-methyl-3,4-dihydro-2H-1-thianaphthalene-4-acetate 1,1-Dioxide By the method of Example 108, 6-fluoro-2-methyl-2H,3H-1-thianaphthalene-4-one 1,1-dioxide (1.0 g, 4.4 mmol) was converted to present title product, purified by flash chromatography on silica gel with ethyl acetate as eluant, 0.80 g.

EXAMPLE 119

6-Fluoro-c-4-hydroxy-r-2-methyl-3,4-dihydro-2H-1-thianaphthalene-4-acetic Acid 1,1-Dioxide By the procedure of Example 109, without chromatography, the product of the preceding Example (0.5 g, 1.5 mmol) was converted to present title product, 24 mg; m.p. 148°–150° C.; m/e 246.0, 229.1, 211.0, 182.1, 165, 123.

$^1$H-NMR(CDCl$_3$)delta(ppm): 7.9–8 (m, 1H), 7.5 (dd, 1H), 7.2–7.3 (t, 1H), 3.5 (m, 1H), 2.9–2.5 (m, 4H), 1.5 (d, 3H).

EXAMPLE 120

Allyl 6-Nitro-c-4-hydroxy-r-2-methyl-3,4-dihydro-2H-1-thianaphthalene-4-acetate

By the method of Example 102, 6-nitro-2-methyl-2H,3H-1-thianaphthalene-4-one (1.0 g, 4.5 mmol) was converted to present title product, purified by flash chromatography with 4:1 hexane:ethyl acetate as eluant, 0.40 g.

EXAMPLE 121

Potassium 6-Nitro-c-4-hydroxy-r-2-methyl3,4-dihydro-2H-1-thianaphthalene-4-acetate The product of the preceding Example (0.40 g) was dissolved in 2 ml ethyl acetate. With stirring, tetrakis(-triphenylphosphine)palladium (20 mg) and triphenylphosphine (20 mg) were added. Once these reagents had dissolved, 2.4 ml of 0.5M potassium ethyl hexanoate in ethyl acetate was added. Product began to precipitate after 15 minutes. After 2 hours, the mixture was diluted with two volumes of ether and title product recovered by filtration, 0.21 g.

EXAMPLE 122

7-Carboxy-c-4-hydroxy-r-2-methylchroman-4-acetic Acid

A solution of 40.5 g (0.25 mol) m-trifluoromethylphenol in 100 ml 2.5N sodium hydroxide was heated at reflux and 20.4 ml (0.25 mol) beta-butyrolactone was added dropwise over 50 minutes. The reaction was cooled to 0° C. and 3 ml concentrated hydrochloric acid was added to bring the pH to 7. The reaction was extracted with 3×100 ml diethyl ether. The pH of the aqueous was brought to 2 with 20 ml concentrated hydrochloric acid and then the aqueous was extracted with 2×100 ml diethyl ether. The latter combined ether extracts were washed with 100 ml water and 100 ml brine, dried over anhydrous magnesium sulfate and concentrated in vacuo to give 9.4 g (15%) of 3-[3-(trifluoromethyl)phenoxy]-butyric acid.

$^1$H-NMR(CDCl$_3$)delta(ppm): 7.12 (m, 4H), 4.83 (q, 1H), 2.85–2.33 (m, 2H), 1.37 (d, 3H).

This product was dissolved in 60 ml 1,2-dichloroethane and 7.89 g (38 mmol) phosphorus pentachloride was added in portions at 23° C. over 20 minutes. This solution was added dropwise to 15.15 g (114 mmol) aluminum chloride in 60 ml 1,2-dichloroethane. A dark color formed. The reaction was cooled to 0° C. and 100 ml 1N hydrochloric acid was added dropwise. The reaction was extracted with 2×100 ml diethyl ether, the combined organics were washed with 100 ml 1N hydrochloric acid, 100 ml brine, dried over anhydrous magnesium sulfate and concentrated in vacuo to give 7.05 g of a brown oil which, based on mass spectral analysis, is 2-methyl-7-trifluoromethylchroman-4-one. To a solution of 4.6 ml (33 mmol) diisopropylamine in 90 ml dry tetrahydrofuran at −5° C. was added 12.7 ml (33 mmol) n-butyllithium in hexane. The reaction was cooled to −78° C. and 3.2 ml (33 mmol) ethyl acetate was added dropwise. To this was added 6.88 g of the above chromanone in 30 ml tetrahydrofuran. The reaction was quenched by dropwise addition of 20 ml water followed by warming to 23° C. The reaction was diluted with 100 ml water and extracted with 2×100 ml diethyl ether. The combined organics were washed with 2×100 ml water and 100 ml brine, dried over anhydrous magnesium sulfate and concentrated in vacuo to give ethyl 7-(trifluoromethyl)c-4-hydroxy-r-2-methylchroman-4-acetate, 6.54 g, as a yellow oil. This material was stirred at 23° C. for 4 hours in a solution of 1.36 g (21 mmol) potassium hydroxide in 70 ml ethanol. The reaction was concentrated in vacuo and the residue was diluted with 100 ml water and extracted with 3×100 ml diethyl ether. The aqueous was acidified to pH 2 with 1N hydrochloric acid and was extracted with 2×100 ml diethyl ether. The combined ether solutions were washed with 2×100 ml water and 100 ml brine, dried over anhydrous magnesium sulfate and concentrated in vacuo to give 1.24 g of a yellow foam. Trituration with hexane gave 736 mg of purified title product as a yellow solid, m.p. 221°–223° C. with decomposition.

$^1$H-NMR(Me$_2$SO)delta(ppm): 7.65 (d, 1H), 7.51 (d, 1H), 7.28 (s, 1H), 5.56 (broad s, 1H), 4.46 (m, 1H), 2.71 (q, 2H), 2.62 (m, 1H), 1.80 (t, 1H), 1.37 (d, 3H).

Analysis calculated for C$_{13}$H$_{14}$O$_6$: C, 58.75; H, 5.37%. Found: C, 58.44; H, 5.26%.

EXAMPLES 123–126

Variously Substituted Ethyl 4-Hydroxy2-(substituted)chroman-4-acetates

By the method of Examples 1, 4, 8, 10, 12, 14, 16 and 18, the appropriately substituted chroman-4-ones were converted to the following substituted ethyl c-4-hydroxy-r-2-(substituted)chroman-4-acetates [showing Example number, name of product, yield (eluant if chromatographed on silica gel) and physical properties/analyses]:

123. Ethyl 6-fluoro-4-hydroxy-2,2-spirocyclopentylchroman-4-acetate; 96%; m/e 308(P+), 261, 227, 221, 203, 181, 139.

124. Ethyl 6-fluoro-c-4-hydroxy-r-2-(4-methoxybenzyl)chroman-4-acetate; 39% (CHCl$_3$); oil; m/e 374(P+, 3%), 356 (P+-H$_2$O, 17%), 235 (89%), 165 (49%), 139 (22%), 121 (100%).

$^1$H-NMR(CDCl$_3$)delta(ppm): 1.2 (t, 3H), 2.2 (d of d, 2H), 3.8 (s, 3H), 4.1 (q, 2H), 4.3 (s and m, 2H), 6.7–7.3 (m, 7H).

125. Ethyl 6-fluoro-c-4-hydroxy-r-2-(4-chlorobenzyl)-chroman-4-acetate; 95% (toluene); m.p. 116°–119° C.;

m/e 380, 378(P+, 12%), 291(P+-CH$_2$CO$_2$C$_2$H$_5$, 11%), 273, 235 (100%), 207, 165 (40%).

$^1$H-NMR(CDCl$_3$)delta(ppm): 1.20 (t, 3H), 1.94 (t, 1H), 2.18 (d, 1H), 2.78 (s, 2H), 2.9 (m, 1H), 3.06 (m, 1H), 4.0–4.4 (m, 3H), 4.45 (s, 1H), 6.7–7.0 (m, 2H), 7.1–7.5 (m, 5H).

Analysis calculated for C$_{20}$H$_{20}$O$_4$ClF·¼C$_6$H$_5$CH$_3$: C, 65.00; H, 5.52%.

Found: C, 64.65; H, 5.47%.

126. Ethyl 7-benzyloxy-6-chloro-c-4-hydroxy-r-2-methylchroman-4-acetate; 100%; oil ($^1$H-NMR consistent with product).

EXAMPLES 127–130

Variously Substituted 4-Hydroxy-2-(substituted)chroman-4-acetic Acids

By the method of Examples 2, 5, 9, 11, 13, 15 and 19, the esters of preceding Examples 20–48 were converted to the following substituted c-4-hydroxy-r-2-(substituted)chroman-4-acetic acids (showing Example number, name of product, yield, and physical properties/analyses):

127. 6-Fluoro-4-hydroxy-2,2-spirocyclopentylchroman-4-acetic acid; 96%; m.p. 110°–112° C.; m/e 280(P+), 233, 221, 203, 181, 139.

Analysis calculated for C$_{15}$H$_{17}$FO$_4$: C, 64.27; H, 6.11%.

Found: C, 64.22; H, 6.02%.

128. Dicyclohexylammonium 6-fluoro-c-4-hydroxy-r-2-(4-methoxybenzyl)chroman-4-acetate; 46% (salt crystallized from ether); m.p. 136°–139° C.; m/e 346(P+, 2.2%), 328(P+-H$_2$O), 207 (15%), 181, 165, 139 (100%), 121, 56, 41.

Analysis calculated for C$_{19}$H$_{19}$O$_5$F·C$_{12}$H$_{23}$N: C, 70.56; H, 8.02; N, 2.66%.

Found: C, 70.93; H, 8.06; N, 2.47%.

129. Dicyclohexylammonium 6-fluoro-c-4-hydroxy-r-(4-chlorobenzyl)chroman-4-acetate; 33% (salt crystallized from ether); m.p. 171°–174° C.; m/e 352, 350(P+, 3.6%), 332(P+-H$_2$O), 207 (40%), 181 (13%), 165 (35%), 138 (100%), 56, 41.

Analysis calculated for C$_{18}$H$_{16}$O$_4$ClF·C$_{12}$H$_{23}$N: C, 67.72; H, 7.39; N, 2.63%.

Found: C, 68.03; H, 7.54; N, 2.48%.

130. Dicyclohexylammonium 7-benzyloxy-6-chloro-c-4-hydroxy-r-2-methylchroman-4-acetate; 50% (salt crystallized from ether); m.p. 192°–194° C. (decomposition); m/e 362(P+), 303(P-CH$_2$CO$_2$H), 300, 181.

Analysis calculated for C$_{19}$H$_{19}$O$_5$Cl·C$_{12}$H$_{23}$N: C, 68.43; H, 7.78; N, 2.57%.

Found: C, 68.38; H, 7.64; N, 2.52%.

SCHEME A

PREPARATION A1

Ethyl R-2-(3-chloro-4-fluorophenoxy)propionate

To a solution of 50 g (0.341 mol) 3-chloro-4-fluorophenol, 38.6 ml (0.341 mol) ethyl S-lactate with rotation [alpha]$_D^{20}$ = −12° (neat) and 89.44 g (0.341 mol) triphenylphosphine in 665 ml tetrahydrofuran was added a solution of 53.7 ml (0.341 mol) diethylazodicarboxylate over 30 minutes while maintaining the reaction temperature below 10° C. The reaction was allowed to warm to 23° C., stirred for 18 hours and then concentrated in vacuo to a slurry. To the mechanically-stirred residue was added 200 ml diethyl ether followed by 100 ml hexane and stirring was continued for 2 hours to break up the clump-like solid. The reaction was filtered and the filter cake washed with 2×75 ml of a 2:1 diethyl ether:hexane solution. The combined filtrate-organic wash was washed with 2×300 ml 0.5N sodium hydroxide, 200 ml water and 200 ml brine. After drying over anhydrous magnesium sulfate and filtration followed by concentration in vacuo, there was obtained 94 g of an oil containing some solid. To this was added 94 ml hexane and the resultant white solid was removed by filtration. The filtrate was flash chromatographed on 94 g silica gel using hexane as eluant to obtain 67.2 g of a pale yellow oil.

$^1$H-NMR(CDCl$_3$)delta(ppm): 7.23–6.47 (m, 3H), 4.63 (q, 1H), 4.20 (q, 2H), 1.60 (d, 3H), 1.27 (t, 3H).

PREPARATION A2

R-2-(3-Chloro-4-fluorophenoxy)propanol

To a solution of 307 g (1.24 mol) ethyl R-2-(3-chloro-4-fluorophenoxy)propionate in 3 liters tetrahydrofuran and 300 ml water was added 131.3 g (3.47 mol) sodium borohydride. The reaction was stirred at 23° C. for 20 hours and then cooled to 10° C. Acetone (455 ml, 6.2 mol) was added dropwise with cooling as required to maintain the temperature below 25° C. Keeping the reaction temperature below 20° C., 1 liter of water was added followed by 500 ml diethyl ether and 200 ml brine. The organic layer was separated and washed with 3×1 liter of a mixture of 800 ml water and 200 ml brine. The organic layer was then dried over anhydrous magnesium sulfate, filtered and the filtrate concentrated in vacuo to give 252.2 g of a dark oil; [alpha]$_D^{25}$ = −29° (CH$_3$OH, C=1).

$^1$H-NMR(CDCl$_3$)delta(ppm): 6.87 (m, 3H), 4.35 (m, 1H), 3.67 (d, 2H), 2.13 (broad s, 1H), 1.24 (d, 3H).

PREPARATION A3

R-2-(3-Chloro-4-fluorophenoxy)propyl Bromide

To a mechanically stirred solution of 80.79 g (0.308 mol) triphenylphosphine in 200 ml toluene was added 15.7 ml bromine over a 30 minute period keeping the temperature below 28° C. After stirring at 23° C. for 1 hour, a solution of 52.5 g (0.257 mol) R-2-(3-chloro-4-fluorophenoxy)propanol in 57 ml toluene was added keeping the temperature below 27° C., and the reaction was stirred at 23° C. for 20 hours. To the reaction was added 20.3 ml (0.5 mol) methanol followed by stirring for 1 hour. The reaction was filtered and the filter cake was washed with 2×50 ml toluene and the combined toluene solutions were concentrated in vacuo at 50° C. The residue was successively triturated with 500 ml followed by 100 ml hexane and the hexane triturates were concentrated in vacuo to give 92 g of an oil. Flash chromatography on 92 g silica gel with hexane eluant gave 60.2 g of a pale yellow oil containing a small amount of triphenylphosphine.

$^1$H-NMR(CDCl$_3$)delta(ppm): 7.47–6.47 (m, 3H), 4.7–4.0 (m, 1H), 3.4 (m, 2H), 1.4 (d, 3H).

PREPARATION A4

2-Benzoylamino-2-[2-(1R-2-bromo-1-methylethoxy)-4-chloro-5-fluorophenyl]acetic Acid To 166 ml methane sulfonic acid cooled in an ice bath was added 58.8 g (0.22 mol) 2-(3-chloro-4-fluorophenoxy)propyl bromide followed by 46.8 g (0.24 mol) alpha-hydroxyhippuric acid. The reaction was stirred at 0° C. for 1 hour and then stirred at 23° C. for 3 hours. The reaction was poured onto 500 ml of vigorously stirred ice-water and the resultant white precipitate was collected by filtration, washed with 3×100 ml water and air dried for 60 hours to give 82 g solid. This was washed with diethyl ether and dried to give 80 g of crude product, m.p. 165°-205° C. This material was dissolved in the minimum volume of dry acetone (about 500 ml), dried over anhydrous magnesium sulfate, filtered and the filtrate concentrated in vacuo to give 71.3 g of an off-white solid, a partially purified mixture of diastereoisomers.

PREPARATION A5
4-Benzoylamino-7-chloro-6-fluoro-2R-methylchroman-4-carboxylic Acid To a solution of 364.8 g (1.09 mol) of crude product of the preceding Preparation in 794 ml dimethylformamide was added 206 ml (2.18 mol) acetic anhydride followed by dropwise addition of 304 ml (2.18 mol) triethylamine over a 15 minute period. An exothermic reaction ensued and after 1 hour the reaction was poured into 2 liters water and extracted with 2×1 liter ethyl acetate. The combined organics were washed with 4×500 ml brine, dried over anhydrous magnesium sulfate, filtered and concentrated in vacuo. To the syrup was added 500 ml dry acetone and the reaction again concentrated in vacuo and held at high vacuum overnight to remove as much solvent as possible to give 332 g (88%) of a syrup. This was dissolved in 2.5 liters acetone, 1.5 liters 3N hydrochloric acid added, and the reaction stirred at 23° C. for 1 hour. The acetone was removed by rotary evaporation. The aqueous residue was extracted with 1 liter methylene chloride, dried over anhydrous magnesium sulfate and concentrated in vacuo to give 351 g of crude title product as a yellow foam, understood to be a mixture of diastereoisomers.

PREPARATION A6
N-(7-Chloro-6-fluoro-2R-methyl-2H-benzo[b]pyran-4-yl)benzamide To a mixture of 347 g (0.95 mol) of crude title product of the preceding Preparation in 1.6 liters methylene chloride was added 466 g (1.05 mol) lead tetraacetate. The mixture was stirred at 23° C. for 15 minutes and then heated at reflux for 3 hours. The reaction was cooled and filtered. The filter cake was washed with 2×300 ml methylene chloride. The combined methylene chloride wash and filtrate was concentrated in vacuo at 40° C. On standing at 23° C. for 60 hours, the resulting 547 g of black oil solidified. To this was added 547 ml diethyl ether and the resultant slurry filtered. The filter cake was washed with 5×273 ml diethyl ether and dried at high vacuum at 23° C. to give 132 g of a brown solid. Material of this purity was used for hydrolysis to the chroman-4-one. A small sample was recrystallized from a 2:1 isopropyl alcohol: diethyl ether to give a light tan solid, m.p. 191°-192° C.
$^1$H-NMR(10:1 CDCl$_3$-DMSO-d$_6$)delta(ppm): 8.43 (broad s, 1H), 7.76 (m, 2H), 7.32 (m, 3H), 6.93 (d, 1H, J=9), 6.72 (d, 1H, J=7), 6.13 (d, 1H, J=4), 5.00 (m, 1H), 1.42 (d, 3H).

PREPARATION A7
2R-7-Chloro-6-fluoro-2-methylchroman-4-one

To a slurry of 127 g (0.4 mol) of crude product of the preceding Preparation in 1.27 liters acetone was added 317 ml 3N hydrochloric acid and the reaction heated at reflux for 1 hour. The reaction was filtered and the filtrate concentrated in vacuo to remove acetone. The residual aqueous was extracted with 500 ml diethyl ether and the ether washed with brine, dried over magnesium sulfate, filtered and concentrated in vacuo to give 67 g of a brown syrup. This was triturated successively with 4×250 ml hexane at reflux. The hexane triturates were combined, cooled to 23° C., filtered and the filtrate concentrated in vacuo to give 27 g of crude product. This was purified by flash chromatography on 625 cc silica gel using 1:10 diethyl ether:hexane as eluant to give 25 g of a white solid. Recrystallization from 125 ml hexane at reflux gave 12.9 g of purified title product, m.p. 106.5°-108° C., [alpha]$_D^{25}$=70.7 (CH$_3$OH, C=1).
$^1$H-NMR(CDCl$_3$)delta(ppm): 7.65 (d, 1H, J=9), 7.12 (d, 1H, J=6), 4.68 (m, 1H), 2.75 (m, 2H), 1.60 (d, 3H).

PREPARATION A8
Ethyl S-O-(Methanesulfonyl)lactate

Ethyl S-lactate (99 g, 0.84 mol) and triethylamine (93.5 g, 0.92 mol) were combined in 500 ml of methylene chloride and cooled to 0°-5° C. Methanesulfonyl chloride (71.5 ml, 0.92 mol) was added portionwise over 1 hour, maintaining the temperature below 10° C., resulting in a thick slurry. After 1 hour at 6°-10° C., 300 ml of water was added, producing a two-phase solution. The aqueous layer was extracted with 40 ml methylene chloride and the organic layers were combined, extracted with 300 ml of water containing 42 g sodium bicarbonate, dried over magnesium sulfate and stripped to yield 16.5 g of title product as an oil; tlc Rf 0.1 (9:1 hexane:ethyl acetate).

PREPARATION A9
Ethyl R-2-(3,4-Dichlorophenoxy)propionate 3,4-Dichlorophenol (85 g, 0.52 mol) was dissolved in 1 liter methylethyl ketone and the solution cooled to 10°-15° C. Caesium carbonate (169 g, 0.52 mol) was added portionwise maintaining the temperature less than 25° C.; the resulting thin suspension recooled to 10°-15° C. and the product of the preceding Preparation (128 g, 0.65 mol) added. The mixture was stirred at ambient temperature for 14 hours, then quenched with 250 ml water. The organic layer was separated, stripped in vacuo to an oil, taken up in 650 ml methylene chloride, washed 2×225 ml 1N sodium hydroxide and 1×100 ml water, dried over magnesium sulfate and stripped to yield title product as an oil, 88 g; tlc Rf 0.4 (4:1 hexane:ethyl acetate).

PREPARATION A10
R-2-(3,4-Dichlorophenoxy)-1-propanol

By the method of Preparation A2, the product of the preceding Preparation (87.8 g, 0.33 mol) was reduced with sodium borohydride. Without prior stripping, the reaction mixture was quenched by the portionwise addition of 110 ml acetone (maintaining the temperature at 20°-25° C. with cooling), then stripped to 280 ml, and extracted 2×200 ml methylene chloride. The organic layers were combined, washed 1×200 ml water, dried over magnesium sulfate and stripped to yield title product as an oil, 63.5 g; tlc Rf 0.2 (4:1 hexane:ethyl acetate).

PREPARATION A11
R-2-(3,4-Dichlorophenoxy)propyl Bromide

Triphenylphosphine (82.5 g, 0.314 mol) was dissolved in 540 ml toluene and cooled to 5°-10° C. as bromine (16.8 ml, 0.33 mol) over 1 hour, and then the product of the preceding Preparation (63 g, 0.286 mol) in 135 ml toluene over 30 minutes were added portionwise while maintaining the temperature at 0°–5° C. The mixture was warmed to ambient temperature, stirred for 12 hours, quenched by the addition of 2 ml methanol, filtered and the filtrate stripped in vacuo to an oil (about 70 ml) which was taken up in 500 ml of hexane. The latter was treated with activated carbon and restripped to yield title product as an oil, 80.3 g, tlc Rf 0.5 (4:1 hexane:ethyl acetate).

PREPARATION A12

2-Benzoylamino-2-[2-(1R-2-bromo-1-methylethoxy)4,5-dichlorophenyl]acetic Acid By the method of Preparation A4, the product of the preceding Preparation (77.5 g, 0.27 mol) was reacted with alpha-hydroxyhippuric acid. Following a reaction period of 8 hours at ambient temperature, the reaction mixture was poured into 1.33 liters of water and 1.33 liters of ethyl acetate. The organic layer was separated, washed 2×400 ml water and 1×400 ml saturated brine, dried over magnesium sulfate, stripped in vacuo to 150 ml, cooled to 0°–5° C., granulated for 1 hour and title product recovered by filtration as a mixture of two diastereoisomers, 61 g; tlc Rf 0.18, 0.23 (13:6:1 hexane:ethyl acetate:acetic acid).

PREPARATION A13

4-Benzoylamino-6,7-dichloro-2R-methylchroman-4-carboxylic Acid

By the method of Preparation A5, the product of the preceding Preparation (61 g, 0.13 mol) was cyclized. Following initial isolation from ethyl acetate, the resulting syrup (about 75 ml) was taken up in 150 ml methylene chloride and 500 ml of 1N sodium hydroxide. The upper aqueous layer was separated and the middle and lower organic layers extracted with a further 500 ml of 1N NaOH. The middle and upper aqueous layers were combined with the original aqueous layer. The lower methylene chloride layer was washed with 500 ml water (also combined with the original aqueous layer). The composite aqueous and oil layer was extracted 2×150 ml methylene chloride, stripped in vacuo to remove any residual methylene chloride, cooled to 5°–10° C. and, with stirring, the pH adjusted to 1.0 with concentrated hydrochloric acid. The resulting solids were granulated at 5°–10° C. for 1 hour, filtered and partially dried to yield water-wet title product, 158.3 g, assumed to contain theoretical 50.3 g of title product; tlc Rf 0.20, 0.23 (13:6:1 hexane:ethyl acetate:acetic acid). The entire wet cake was used without drying in the next step.

PREPARATION A14

2R-6,7-Dichloro-2-methylchroman-4-one

The entire batch of product from the preceding Preparation was combined with 375 ml methylene chloride and the pH adjusted to 6.9 with 4.5 ml 50% NaOH. Sodium hypochlorite (15% w/v, 1.14 liters) was added portionwise over 1.5 hours, maintaining a temperature of 20°–25° C., the mixture stirred for 34 hours, and the aqueous layer separated and washed with 175 ml methylene chloride. The organic layers were combined, washed in sequence with 1×200 ml 2N NaOH, 1×200 ml 10% (w/v) NaHSO$_3$, 1×200 ml water, 1×200 ml 6N HCl and 1×200 ml water, and stripped in vacuo to yield present title product as an oil, 24.9 g, which crystallized on stirring with 40 ml methanol, recovered by filtration after cooling and granulating at 0°–5° C., 10 g; tlc Rf 0.45 (1:1 hexane:CHCl$_2$), 0.25 (4:1 hexane:ethyl acetate), 0.45 (13:6:1 hexane:ethyl acetate:acetic acid).

PREPARATION A15

Ethyl 2R-2-(4-Fluorophenyloxy)propionate

To a stirred solution consisting of p-fluorophenol (7.5 g, 0.067 mol), (S)-ethyl lactate (7.9 g, 0.067 mol) and triphenylphosphine (18.75 g, 0.067 mol) all dissolved in tetrahydrofuran (100 ml), there was added dropwise over a 15-minute period a solution consisting of diethylazodicarboxylate (12.5 g, 0.067 mol) dissolved in tetrahydrofuran (50 ml). The resulting reaction solution was then stirred at room temperature for a period of 18 hours. At this point, the tetrahydrofuran was removed by evaporation in vacuo and a mixture consisting of diethyl ether (150 ml) and hexanes (150 ml) was added to precipitate the solids. The latter were then removed by filtration, washed with hexanes and discarded. The resulting filtrate was thereafter washed with 1N aqueous sodium hydroxide (2×50 ml), water (50 ml) and brine (50 ml), followed by drying over magnesium sulfate. After removal of the drying agent by means of filtration and the solvents by means of evaporation under reduced pressure, there was obtained an oil which was subjected to vacuum distillation to ultimately afford purified title product, 10.2 g (72%); b.p. 90°–92° C./0.7 mm. Hg. [alpha]$_D^{25}$= +37.4° (c=2.148, CHCl$_3$); IR(CHCl$_3$) 1748(C=O) cm$^{-1}$.

$^1$H-NMR(CDCl$_3$)delta(ppm): 7.0 (m, 4H, aromatic CH), 4.8 (q, 1H), 4.3 (q, 2H), 1.6 (d, 3H), 1.3 (t, 3H). Analysis calculated for C$_{11}$H$_{13}$FO$_3$: C, 62.26; H, 6.13%. Found: C, 62.25; H, 6.22%.

PREPARATION A16

2S-2-(4-Fluorophenoxy)propanol

Ethyl 2S-2-(4-fluorophenoxy)propionate (27.3 g, 0.129 mol) prepared as described in the preceding Preparation in dry tetrahydrofuran (100 ml) was added dropwise to a stirred suspension of lithium aluminum hydride (3.8 g, 0.1 mol) in dry tetrahydrofuran (150 ml). The resulting reaction mixture was then stirred for a period of three hours after completion of the addition. To the stirred mixture, there was then carefully added in a dropwise manner 10% aqueous tetrahydrofuran (30 ml), saturated aqueous sodium sulfate solution (8 ml) and finally sodium sulfate (5 g). The spent reaction mixture was then stirred 16 hours at room temperature to ensure completeness of reaction with respect to excess hydride. The resulting solids were then filtered and washed with hot tetrahydrofuran (2×75 ml). The combined filtrate and washings were thereafter evaporated under reduced pressure to remove the tetrahydrofuran and the residual oil thus obtained was subsequently dissolved in methylene chloride (150 ml), followed by drying over magnesium sulfate. After removal of the drying agent by means of filtration and the solvent by means of evaporation under reduced pressure, there was obtained an oil which was subjected to vacuum distillation to ultimately afford purified title product, 20.3 g (94%); b.p. 85°–95° C./0.6 mm. Hg; [alpha]$_D^{25}$= −33.0° (c=2.125, MeOH).

$^1$H-NMR(CDCl$_3$)delta(ppm): 7.1 (m, 4H), 4.4 (m, 1H), 3.8 (d, 2H), 3.0 (broad s, OH), 1.3 (d, 3H).

PREPARATION A17

2R-2-(4-Fluorophenoxy)propyl Bromide

Bromine (19.8 g, 0.124 mol) was added dropwise to a solution of the product of the preceding Preparation (20 g, 0.118 mol) and triphenylphosphine (32.4 g, 0.124 mol) dissolved in dimethylformamide (75 ml), with the temperature being maintained below 25° C. by means of an ice water bath. The reaction mixture was then stirred at room temperature for a period of 18 hours. The resulting solution was next diluted with ethyl acetate (500 ml) and thereafter washed with water (3×200 ml), saturated aqueous sodium bicarbonate (150 ml), water (150 ml) and brine (75 ml). The washed ethyl acetate solution was then dried over magnesium sulfate, filtered and the resulting filtrate subsequently concentrated in vacuo to afford a slurry which was thereafter diluted with hexanes (250 ml) and stirred for one-half hour. The precipitate which formed at this point was removed by means of filtration and the hexane filtrate was subsequently evaporated under reduced pressure to give an oil which was then subjected to vacuum distillation to ultimately afford 22.16 g (80%) of purified title product; b.p. 83°–85° C./0.15 mm. Hg; $[alpha]_D^{25} = -10.2°$ (c=2.258, MeOH); IR(CHCl$_3$) 2956 (w), 2922 (w), 1726 (m), 1495 (m) cm$^{-1}$.

$^1$H-NMR(CDCl$_3$)delta(ppm): 7.1 (m, 4H), 4.5 (m, 1H), 3.5 (m, 2H), 1.4 (d, 3H); mass spectrum, (m/e) 233/231 (M+), 112 (base peak, p-fluorophenol).

Analysis calculated for C$_9$H$_{10}$BrFO: C, 46.35; H, 4.29%.

Found: C, 46.36; H, 4.26%.

PREPARATION A18

2-Benzoylamino-2-[2-(R-2-bromo-1-methylethoxy)-5-fluorophenyl]acetic Acid

The product of the preceding Preparation (193 g, 0.86 mol) was added in a slow stream to cold methanesulfonic acid (620 ml) with the aid of mechanical stirring. The resulting solution was then maintained at less than 15° C., while N-benzoyl-alpha-hydroxyglycine (156 g, 0.8 mol, alpha-hydroxyhippuric acid) was added thereto in several portions over a period of 20 minutes. The resulting reaction mixture was then allowed to warm slowly to room temperature and stirred for 40 hours. The viscous solution thus obtained was then poured over 1.5 liters ice with constant agitation to precipitate the crude product as a yellow solid. The latter material was subsequently collected by means of suction filtration, washed with water and then ethanol, and air-dried to constant weight to afford 293 g (83%) of title product; m.p. 203°–210° C.

$^1$H-NMR(DMSO-d$_6$)delta(ppm): 8.9 (t, 1H), 8.2–7.1 (m, 8H), 6.1 (d, 2H), 4.7 (m, 1H), 3.7 (d, 2H), 1.3 (dd, 3H).

Analysis calculated for C$_{18}$H$_{17}$FBrNO$_4$: C, 52.73; H, 4.18; N, 3.42%.

Found: C, 52.78; H, 4.22; N, 3.40%.

PREPARATION A19

2R-6-Fluoro-2'-phenyl-2-methylspiro[chroman-4,4'-oxazolidin]-5'-one

The product of the preceding Preparation (25 g, 0.061 mol) and potassium carbonate (16.85 g, 0.122 mol) were suspended in acetone (100 ml), treated with acetic anhydride (9.2 g, 0.09 mol) at room temperature and stirred for 24 hours, during which time precipitation of salts (i.e., potassium bromide) occurred. The spent reaction mixture was then filtered and the resulting filtrate subsequently concentrated in vacuo to afford title product as an orange oil, 17 g.

$^1$H-NMR(CDCl$_3$)delta(ppm): 8.2 (m, 2H), 7.7 (m, 3H), 7.1 (m, 2H), 6.7 (m, 1H), 4.7 (m, 1H), 2.4–2.0 (m, 2H), 1.5 (m, 3H).

This product is treated with HCl and then Pb(OAc)$_4$, according to the method of Lohmar and Steglich, Agnew. Chem. Int. Ed. Engl. 17, pp. 450–451 (1978); or with HCl and then sodium hypochlorite, according to Preparation A14 above, to produce 2R-6-fluoro-2-methylchroman-4-one.

PREPARATION A20

2S-2-Hydroxy-3-phenylpropionic Acid

L-Phenylalanine (165 g, 1 mol) was dissolved in 1 liter 2N sulfuric acid and treated dropwise over 70 minutes at −5° C. with sodium nitrite (74 g, 1.07 mol) in 300 ml water, then stirred 16 hours at room temperature and extracted 3×600 ml ethyl acetate. The extracts were combined, washed with brine, dried over magnesium sulfate, stripped and the solids slurried in hexane to yield title product, 42.2 g (25%). $[alpha]_D^{25} = -16.99°$ (c=1.018 in methanol).

PREPARATION A21

Methyl 2S-2-Hydroxy-3-phenylpropionate

The acid product of the preceding Preparation (40 g, 0.24 mol) was dissolved in 500 ml methylene chloride containing 30 ml methanol. Concentrated sulfuric acid (4 ml) was added and then the mixture gently refluxed for 16 hours, cooled to room temperature, washed in sequence with 250 ml each of water, saturated sodium bicarbonate and brine, dried and stripped to yield title product as a solid, 40.6 g (96%); $[alpha]_D^{25} = +3.78°$ (c=1.057 in methanol).

$^1$H-NMR(CDCl$_3$)delta(ppm): 7.25 (s, 5H, aromatics), 4.45 (m, 1H), 3.8 (s, 3H, CH$_3$), 3.1 (m, 3H, $\phi$CH$_2$ and OH).

PREPARATION A22

Methyl 2R-2-(4-Bromophenoxy)-3-phenylpropionate

By the method of Preparation A1, using chloroform as eluant on chromatography, 4-bromophenol (37 g, 0.214 mol) and product of the preceding Preparation (35 g, 0.194 mol) were converted to present title product as an oil, 33 g; $[alpha]_D^{25} = +16.42°$ (c=1.16 in methanol).

$^1$H-NMR(CDCl$_3$)delta(ppm): 7.3 (m, 7H), 6.7 (d, 2H), 4.8 (t, 1H), 3.7 (s, 3H), 3.2 (d, 2H).

PREPARATION A23

2R-2-(4-Bromophenoxy)-3-phenyl-1-propanol

The product of the preceding Preparation (45.9 g, 0.137 mol) and sodium borohydride (7.8 g, 0.205 mol) were combined in 500 ml absolute ethanol and stirred 40 hours at room temperature. Acetone (30 ml) was then added, the mixture stripped to dryness, the residue taken up in 400 ml methanol and 10 ml of 1N hydrochloric acid, and the mixture refluxed for 2 hours over a Sohxlet extractor containing strongly basic ion exchange resin to facilitate removal of borates. The methanol was then stripped and the residue distributed between 500 ml each methylene chloride and saturated sodium bicarbonate. The organic layer was separated, washed in sequence with 250 ml each of water, 1N hydrochloric acid and brine, dried over magnesium sulfate, and stripped to yield crude product still containing borate ester. The latter was heated in 200 ml concentrated hydrochloric acid and 75 ml acetic acid at 50°–55° C. for 2 hours, cooled to room temperature, extracted with 200 ml methylene chloride, and the methylene chloride layer separated and stripped to yield title product as an oil; 32.1 g (76%); $[alpha]_D^{25} = +21.85°$ (c=1.04 in methanol).

$^1$H-NMR(CDCl$_3$)delta(ppm): 7.3 (m, 7H), 6.8 (d, 2H), 4.4 (m, 1H), 3.7 (m, 2H), 3.0 (d, 2H), 2.7 (s, 1H).

PREPARATION A24

2R-2-(4-Bromophenoxy)-3-phenylpropyl Bromide

The product of the preceding Preparation (30 g, 0.1 mol) and triphenylphosphine (28.8 g, 0.11 mol) were stirred in 150 ml dimethylformamide as bromine (17.6 g, 5.6 ml, 0.11 mol) was added dropwise over 10 minutes. A mild exotherm was noted. After warming to 50° C. for 2 hours, the mixture was stirred 16 hours at room temperature, diluted with 200 ml each water and ethyl acetate, and the organic layer separated, washed 3×200 ml water and 1×200 ml brine, dried over magnesium sulfate and stripped to yield title product as an oil; 28.3 g; $[alpha]_D^{25} = +10.5°$ (c=1.09 in methanol).

PREPARATION A25

2-Benzoylamino-2-[2-(1R-2-bromo-1-methylethoxy)-5-bromophenyl]acetic Acid

By the method of Preparation A4, the product of the preceding Preparation (24 g, 0.065 mol) was reacted with alpha-hydroxyhippuric acid (14 g, 0.078 mol) in methanesulfonic acid (75 ml). After stirring for 4 hours at 0° C., ice and then water were added to the reaction to a total volume of 800 ml and the mixture warmed to room temperature and title product recovered by filtration; 36.9 g; IR(KBr) cm$^{-1}$ 3427 (s), 1737 (s), 1640 (s). $^1$H-NMR(CDCl$_3$)delta(ppm): 7.9–7.0 (m, 1H), 6.7 (d, 1H, NH), 6.3 (s, H$_2$0), 5.8 (dd, 1H), 4.6 (m, 1H), 3.5 (d, 2H), 3.1 (m, 2H).

PREPARATION A26

2R-4-Benzoylamino-2-benzyl-6-bromochroman-4-carboxylic Acid

According to the procedure of Preparation A19, the product of the preceding Preparation (3 g, 0.0055 mol) was reacted with acetic anhydride and potassium carbonate. Following filtration of the reaction mixture, the filtrate was stripped to 40 ml, diluted with 10 ml of 3N hydrochloric acid and warmed to achieve complete solution. After 15 minutes at 35°–40° C., the mixture was diluted with an equal volume of water and acetone boiled away. The oily layer which separated was extracted into an equal volume of methylene chloride, dried over magnesium sulfate and stripped to yield title product as a foam, 2.27 g, used without further purification or characterization in the next step.

PREPARATION A27

2R-2-Benzyl-6-bromochroman-4-one

By the method of Preparations A6 and A7, without purification or characterization of the intermediate, the entire batch of product of the preceding Preparation was converted to present title product, 1.4 g, suitable for conversion to 2R,4R-2-benzyl-6-bromo-4-hydroxychroman-4-acetic acid according to the methods of the Examples above.

PREPARATION A28

2-Hydroxy-3-phenylpropionic Acid

By the method of Preparation A20, dl-phenylalanine (80 g) was converted to title product, 49 g; m.p. 95°–98° C.

PREPARATION A29

Methyl 2-Hydroxy-3-phenylpropionate

By the method of Preparation A21, the product of the preceding Preparation (48.85 g) was converted to present title product as an oil, 52.9 g. $^1$H-NMR essentially as that of the corresponding chiral product of Preparation A21.

PREPARATION A30

Methyl 2-(4-Methoxycarbonylphenoxy)3-phenylpropionate

By the method of Preparation A22, the product of the preceding Preparation (15.4 g) was coupled with alpha-hydroxyhippuric acid to produce title product initially isolated as an oil which was crystallized from isopropanol, 20.7 g; m.p. 96°–98° C.

PREPARATION A31

2-[4-(Methoxycarbonyl)phenoxy]-3-phenyl-1-propanol

By the method of Preparation A10, the product of the preceding Preparation (2.04 g) was reduced and product isolated, initially as an oil which crystallized on standing, 18.2 g; tlc Rf 0.1 (CHCl$_3$).

PREPARATION A32

2-[4-(Methoxycarbonyl)phenoxy]-3-phenylpropyl Bromide

The method of Preparation A11 was employed to convert the product of the preceding Preparation (18 g) to present title product, 16.7 g; tlc Rf 0.6 (CHCl$_3$).

PREPARATION A33

Methyl 2-Benzylchroman-4-one-6-carboxylate

Stirring at room temperature, the product of the preceding Preparation, (16.35 g, 0.0585 mol) was dissolved in 85 ml of methanesulfonic acid. alpha-Hydroxyhippuric acid (12.95 g, 0.066 mol) was added; the temperature exothermed to 38° C. The mixture was stirred at room temperature for 20 hours, then added over a 1 hour period to 400 ml of water maintaining a temperature of 10°–20° C. The resulting precipitated solids were granulated at 20°–25° C. for 30 minutes and intermediate product recovered by filtration, using 40 ml of water for wash. The wet cake was taken up in 150 ml methylene chloride and the resulting solution washed with 30 ml water, dried over magnesium sulfate, and the methylene chloride displaced with acetone, boiling to a final pot temperature of 50° C. while maintaining a total volume of 150 ml. To the resulting solution of N-benzoylamino acid bromide intermediate (assaying for 28.2 g by aliquot strip) was added acetic anhydride (10.9 g) and then, with external cooling, 14.71 g of potassium carbonate. The temperature exothermed to 40° C. The mixture was cooled and stirred for 16 hours at room temperature and filtered. The filtrate was stripped to 120 ml, diluted with 20 ml of 1:1 concentrated hydrochloric acid:water, stirred 3 hours at room temperature, filtered and the filtrate stripped to about 150 ml (producing a thick, gummy mass), diluted with 50 ml water, and extracted with 400 ml methylene chloride. The organic layer was separated and washed 3×60 ml water. To the resulting solution of 6-(methoxycarbonyl)-4-(benzoylamino)-2-benzylchroman-4-acetic acid was added 1.16 liters of 20% sodium hypochlorite. The temperature, which initially exothermed to 32° C., was maintained at 24°-27° C., with good stirring of the two-phase reaction system. The aqueous layer was separated and extracted 2×200 ml methylene chloride. The methylene chloride layers were combined, washed 2×800 ml water, charged with 2 g of 5% Pd/C and hydrogenated under 4 atmospheres of hydrogen for 7 hours. The catalyst was recovered by filtration and the filtrate stripped to an oil which was taken up in a mixture of 5 ml concentrated hydrochloric acid, 5 ml water and 80 ml methanol, and heated to 50° C. to entirely dissolve the oil. After stirring 16 hours at room temperature, a first crop of crude title product (4.4 g) was recovered and a second crop (2.8 g) recovered by stripping filtrate to ½ volume. The first crop was recrystallized from acetone/methanol to yield purified title product, 3.1 g; m.p. 103°-104° C.

SCHEME B

PREPARATION B1

3,4-Dichlorophenyl Acetate

At room temperature, 3,4-dichlorophenol (298.5 g, 1.83 mol) was dissolved in 191 ml (207 g, 2.02 mol) of acetic anhydride in a 1 liter flask equipped with mechanical stirrer and condenser. Sulfuric acid (3 ml) was added, resulting in a strong exotherm. After 2 hours the mixture was poured into 2 liters of ice and water and extracted 3×1 liter diethyl ether. The organic layers were combined, washed 1×1 liter water, 2×1 liter saturated sodium bicarbonate and 1×1 liter saturated brine, dried over magnesium sulfate and stripped to yield title product as an orange oil, 375 g, tlc Rf 0.5 (1:1 diethyl ether:hexane).

PREPARATION B2

4,5-Dichloro-2-hydroxyacetophenone

Title product of the preceding Preparation (166.1 g, 0.810 mol) was stirred at room temperature as aluminum chloride (216 g, 1.62 mol) was added portionwise. A strong exotherm was noted. The mixture was heated at 120° C. for 1 hour and then recooled to room temperature. The resulting solids were broken up, slurried with 2 liters of ice and extracted with 2×1 liter ethyl acetate. The organic layers were combined, washed 1×1 liter 1N hydrochloric acid, 1×1 liter water and 1×1 liter brine, dried over magnesium sulfate and stripped in vacuo to a white solid, 129 g. This was crystallized from 600 ml diisopropyl ether, 86.9 g (52%), m.p. 99°-105° C., uncontaminated by isomer by $^1$H-NMR.
Analysis calculated for $C_8H_6O_2Cl_2$: C, 46.86; H, 2.95%.
Found: C, 46.92; H, 2.87%.

PREPARATION B3

1-(2-Hydroxy-4,5-dichlorophenyl)-1,3-butandione

Sodium hydride (1.24 mol) from 59.5 g of a 50% oil dispersion was slurried in 400 ml tetrahydrofuran at 0° C. A solution of 101.8 g (0.496 mol) 4,5-dichloro2-hydroxyacetophenone dissolved in 200 ml tetrahydrofuran was added dropwise to give a yellow suspension. After 20 minutes stirring, 53.4 ml (0.546 mol) ethyl acetate was added dropwise. The reaction was warmed slowly to 23° C. and stirred for 20 hours. The resulting suspension was poured over 2 liters of an ice-1N hydrochloric acid mixture, then extracted with 2×500 ml diethyl ether. The combined organic layers were washed with 2×500 ml water, 500 ml brine and dried over magnesium sulfate. Concentration in vacuo gave a brown foam which was triturated with 800 ml hexane. Filtration gave the product as a tan solid, 106.8 g (87%), m.p. 134°-135° C.
Analysis calculated for $C_{10}H_8O_3Cl_2$: C, 48.61; H, 3.26%.
Found: C, 48.66; H, 3.22%.

PREPARATION B4

6,7-Dichloro-2-methyl-4H-benzo[b]pyran-4-one

To 316 ml (4.1 mol) trifluoroacetic acid in 1.5 liters methylene chloride was added 240 g (0.971 mol) of title product of the preceding Preparation. The reaction was stirred at 23° C. for 60 hours, then cooled to 0° C. and 1 liter 1N sodium hydroxide added with stirring. The organic layer was separated and washed with 2×1 liter 1N sodium hydroxide followed by 1 liter water and 1 liter brine. After drying over magnesium sulfate, the methylene chloride solution was filtered through diatomaceous earth and concentrated in vacuo to a tan solid. This was triturated with 800 ml hexane to give the product as a tan solid, 168.5 g (76%); m.p. 143°-147° C.
$^1$H-NMR(CDCl$_3$)delta(ppm): 8.07 (s, 1H), 7.10 (s, 1H), 6.08 (s, 1H), 2.37 (s, 3H).
Analysis calculated for $C_{10}H_6O_2Cl_2$: C, 52.43; H, 2.64%.
Found: C, 52.58; H, 2.59%.

PREPARATION B5

6,7-Dichloro-2-methylchroman-4-one

Lithium aluminum hydride (12.94 g, 0.341 mol) was suspended in 1.3 liters tetrahydrofuran. To the stirred slurry at −78° C. was added 76.1 g (0.332 mol) of title product of the preceding Preparation in one portion. The reaction was monitored by thin layer chromatography (silica gel with 1:1 diethyl ether: hexane as eluant). As soon as the more polar starting material spot had disappeared (about 1 hour), the reaction was quenched by dropwise addition of 82 ml (1.43 mol) glacial acetic acid to the −78° C. reaction mixture. The reaction was warmed to 23° C., diluted with 1 liter water and extracted with 2×500 ml diethyl ether. The combined ether layers were washed with 2×500 ml 1N NaOH, 500 ml water, 500 ml brine and dried over magnesium sulfate. Concentration in vacuo gave the product as a tan solid, 64.4 g (84%); m.p. 59°-62° C.
$^1$H-NMR(CDCl$_3$)delta(ppm): 7.80 (s, 1H), 7.03 (s, 1H), 4.55 (m, 1H), 2.36 (m, 2H), 1.50 (d, 3H).
Analysis calculated for $C_{10}H_8O_2Cl_2$: C, 51.97; H, 3.49%.
Found: C, 51.90; H, 3.49%.

PREPARATION B6

1-(3,4-Dichloro-1-hydroxyphenyl)-4,4,4-trifluorobutane-1,3-dione

A solution of 5 g (24.4 mmol) 3,4-dichloro-1-hydroxyacetophenone in 20 ml tetrahydrofuran was added to a slurry of 48.8 mmol sodium hydride (derived from 2.34 g of a 50 percent mineral oil dispersion which had been prewashed with petroleum ether to remove the oil) suspended in 10 ml tetrahydrofuran. To the reaction was added 3.19 ml (26.8 mmol) ethyltrifluoroacetate keeping the temperature below 5° C. The reaction was stirred 1 hour at 0° C., allowed to warm to 23° C., stirred for 20 hours, and finally poured into 60 ml 1N hydrochloric acid and 30 ml ice-water. The quench was extracted with 40 ml diethyl ether, and the ether layer separated, washed with 20 ml water and 20 ml brine, dried over magnesium sulfate and concentrated in vacuo to give 5.8 g of a tan solid. NMR analysis (20:1 CDCl$_3$-DMSO-d$_6$) showed a 2:3 molar mixture of product to unreacted acetophenone).

$^1$H-NMR(CDCl$_3$)delta(ppm): 7.83 (s, 1H), 7.10 (s, 1H), 2.97 (s, 2H).

PREPARATION B7

6,7-Dichloro-2-(trifluoromethyl)benzo[b]pyran

A solution of 4.62 g of crude product of the preceding Preparation, 4-(3,4-dichloro-6-hydroxyphenyl)-1,1,1-trifluoro-butan-2,4-dione (about 40% by NMR) and 4.6 ml trifluoroacetic acid in 27.6 ml methylene chloride was heated at reflux for 8 hours, then allowed to stand at 23° C. for 16 hours. The reaction was washed with 3×25 ml 1N sodium hydroxide and 25 ml brine, dried over anhydrous magnesium sulfate and concentrated in vacuo to give 2.0 g (86%) of product; m.p. 98°–101° C.

$^1$H-NMR(CDCl$_3$)delta(ppm): 8.22 (s, 1H), 7.68 (s, 1H), 6.68 (s, 1H).

PREPARATION B8

6,7-Dichloro-2-(trifluoromethyl)chroman-4-one

To 39 mg (1.03 mmol) lithium aluminum hydride in 4 ml tetrahydrofuran at −78° C. was added 283 mg (1 mmol) of the product of the preceding Preparation. The reaction was stirred at −78° C. for 3 hours and then quenched by slow addition of 0.3 ml acetic acid, allowed to warm to 23° C., and finally diluted with diethyl ether. The ether was washed with 25 ml 1N sodium hydroxide, 2×25 ml diethyl ether and 25 ml brine, dried over magnesium sulfate and concentrated in vacuo to give 245 mg (86%) of product as an off-white solid; m.p. 94.5°–97° C.

$^1$H-NMR(CDCl$_3$)delta(ppm): 7.80 (s, 1H), 7.13 (s, 1H), 4.73 (m, 1H), 2.90 (d, 2H).

SCHEME C

PREPARATION C1

6-Fluoro-2-methylchroman-4-one

A solution of 0.91 ml (16.3 mmol) acetaldehyde in 5 ml benzene was added over 30 minutes to a refluxing solution of 2.71 ml (32.5 mmol) pyrrolidine in 20 ml benzene while removing water with a Dean-Stark trap. To the refluxing solution was added 0.5 g (3.25 mmol) 5-fluoro-2-hydroxyacetophenone in 5 ml benzene in one portion. Following 30 minutes reflux the reaction was cooled to 23° C. and washed with 3×20 ml 1N hydrochloric acid, 2×20 ml 1N sodium hydroxide and 20 ml brine, and dried over magnesium sulfate. Concentration in vacuo gave 28 mg (4.7%) of the product as a yellow solid. On standing for 20 hours the combined 1N hydrochloric acid washes deposited yellow platelets. These were collected by filtration and dried to give 287 mg (49%) of product.

$^1$H-NMR(CDCl$_3$)delta(ppm): 7.57–6.73 (m, 3H), 4.57 (m, 1H), 2.67 (m, 2H), 1.50 (d, 3H). The Chemical Abstract Registry Nos. for this compound are 88754-96-5 and 82320-16-9.

By the same method, the following additional chromane-4-ones were prepared from the appropriately substituted 2-hydroxyacetophenone and the appropriate aldehyde or ketone:

| Substituents on Chromane-4-one | Ketone/ Aldehyde | Yield (%) | m.p. (°C.) |
|---|---|---|---|
| 2,2-Dimethyl | Acetone | 45 | 86–87.5 |
| 7-Fluoro-2,2-dimethyl | Acetone | 45 | oil |
| 6,7-Dichloro-2,2-dimethyl | Acetone | 61 | 98–103 |
| 7-Fluoro-2-isopropyl | Isobutyraldehyde | 36 | oil |
| 7-Fluoro-2-(t-butyl) | Pivaldehyde | 49.5 | — |

PREPARATION C1

| Substituents on Chromane-4-one | Ketone/ Aldehyde | Yield (%) | m.p. (°C.) |
|---|---|---|---|
| 6-Fluoro-2,2-spirocyclopentyl | Cyclopentanone | 67 | 57–59 |
| 7-Fluoro-2-ethyl-2-methyl | 2-Butanone | 22.5 | oil |
| 7-Fluoro-2-(2-phenylethyl) | Hydrocinnamaldehyde | 66[a] | oil |
| 5,6-Dichloro-2,2-dimethyl | Acetone | 58 | oil |

[a]Chromatographed on silica gel with 1:6 diethyl ether:hexane.

SCHEME D

PREPARATION D1

6-Fluoro-2-phenylchroman-4-one

In a shaker bottle were combined 2.5 g (16.2 mmol) 5-fluoro-2-hydroxyacetophenone, 1.65 ml (16.2 mmol) benzaldehyde, 20 ml 96% ethanol and 5.83 g (145.8 mmol) sodium hydroxide. The yellow slurry was shaken vigorously for 30 minutes during which time the reaction solidified. After standing 3 hours, the reaction was triturated with ether and after filtration the resulting orange solid was added to 200 ml 1N hydrochloric acid and the resulting yellow solid collected by filtration and dried at 60° C. in vacuo for 20 hours to give 2.4 g of the intermediate 2-hydroxy-5-fluorochalcone. This material was added to a solution of 0.396 g (9.91 mmol) sodium hydroxide in 99 ml of a 3:1 water:ethanol solution. The resultant orange slurry was stirred for 5 hours at 23° C., then filtered and the solid washed well with water and dried to give the title compound, 1.92 g (80%).

$^1$H-NMR(CDCl$_3$)delta(ppm): 7.67–6.77 (m, 8H), 5.40 (m, 1H), 2.93 (m, 2H).

SCHEME E

PREPARATION E1

6-Fluoro-2-(3,4-dichlorobenzyl(chroman-4-one

To a flame dried 125 ml 3-neck flask containing 0.243 g (10 mmol) magnesium under nitrogen was added 5 ml dry diethyl ether followed by 1.38 ml (10 mmol) 3,4-dichlorobenzyl chloride in 20 ml of diethyl ether to form the Grignard reagent. After stirring 30 minutes, 60 mg cuprous iodide was added to the reaction at −20° C. and during stirring for 15 minutes at this temperature a tan-green suspension was observed in the reaction. To the stirred reaction was added 1.64 g (10 mmol) 6-fluoro-4H-chromen-4-one dissolved in 25 ml diethyl ether in portions over 2 minutes. A momentary, localized red color was observed during the addition. The reaction was stirred at −20° C. for 1 hour and then allowed to warm to 23° C. and stirred for 20 hours to give a red-orange solid suspension. This was diluted with 50 ml chloroform and 3N hydrochloric acid was added with stirring until the reaction was acidic and the organic layer was a bright yellow color. The aqueous layer was extracted with 2×50 ml chloroform and the combined organic layers were washed with 50 ml water and 50 brine, dried over magnesium sulfate and concentrated in vacuo to 3.2 g of orange solid residue. This was chromatographed on silica gel with toluene eluant to give title product, 1.1 g (34%) as a yellow oil which crystallized on standing; m.p. 101°-103° C.

1H-NMR(CDCl3)delta(ppm): 7.62-6.96 (m, 6H), 4.68 (m, 1H), 3.1 (m, 2H), 2.7 (d, 2H).

By the same method 4-chlorobenzyl chloride was converted to 6-fluoro-2-(4-chlorobenzyl)chroman-4-one, also purified by chromatography on silica gel with toluene as eluant, 74%; m.p. 98°-100° C.

1H-NMR(CDCl3)delta(ppm): 2.70 (d, 2H), 3.0-3.15 (m, 2H), 4.68 (m, 1H), 6.95-7.70 (m, 7H).

Analysis calculated for $C_{16}H_{12}O_2ClF$: C, 66.10; H, 4.16%.

Found: C, 66.65; H, 4.20%.

By the same method 4-methoxybenzyl bromide was converted to 6-fluoro-2-(4-methoxybenzyl)chroman-4-one, also purified by chromatography on silica gel with toluene as eluant, 68%; waxy solid; tlc Rf 0.40 (toluene).

1H-NMR(CDCl3)delta(ppm): 2.6 (d, 2H), 3.0 (m, 2H), 3.8 (s, 3H), 4.6 (m, 1H), 6.7-7.6 (m, 7H).

By the same method benzyl chloride was converted to 6-fluoro-2-benzylchroman-4-one, also purified by chromatography on silica gel with toluene as eluant, 19%; m.p. 79°-82° C.

1H-NMR(CDCl3)delta(ppm): 2.6 (d, 2H), 3.1 (dd, 2H), 4.6 (m, 1H), 6.8-7.6 (m, 8H).

Analysis calculated for $C_{16}H_{13}O_2F$: C, 74.99; H, 5.11%.
Found: C, 74.64; H, 4.99%.

SCHEME F

PREPARATION F1

3-(4-Nitrophenoxy)butyric Acid

4-Nitrophenol (34.78 g, 0.25 mol) was added to a solution of 10 g (0.25 mol) sodium hydroxide in 100 ml water and the solution heated at reflux for 15 minutes. To the solution at reflux, 20.4 ml (0.25 mol) betabutyrolactone was added dropwise over a 1.5 hour period. The reaction was cooled to 23° C. and extracted with 2×150 ml diethyl ether. The combined ether layers were extracted with 4×140 ml saturated sodium bicarbonate solution and the bicarbonate then acidified with 60 ml concentrated hydrochloric acid and back-extracted with 200 ml diethyl ether. The ether back extract was washed with 50 ml water and 50 ml brine, and dried over magnesium sulfate. Concentration in vacuo gave the product as a yellow oil, 31.2 g (55%).

1H-NMR(CDCl3)delta(ppm): 10.23 (broad s, 1H), 8.10 (m, 2H), 6.92 (m, 2H), 4.93 (m, 1H), 2.70 (m, 2H), 1.43 (d, 3H).

PREPARATION F2

2-Methyl-6-nitrochroman-4-one

A mixture of 31.2 g (139 mmol) 3-(4-nitrophenoxy)butyric acid, 139 ml methanesulfonic acid and 7 g phosphorus pentoxide was heated on the steam bath for 1.75 hours. The reaction was cooled to 23° C., poured onto 500 ml ice-water mixture and extracted with 2×200 ml diethyl ether. The combined organic extracts were washed with 2×150 ml 1N sodium hydroxide, clarified by filtration, washed with 2×50 ml water and 100 ml brine, dried over magnesium sulfate and concentrated in vacuo to give the crude product as a yellow solid, 2.9 g (10%). Recrystallization from methylene chloride and isopropyl ether gave 1.35 g (4.7%) golden platelets, m.p. 144°-145° C.

1H-NMR(CDCl3)delta(ppm): 8.60 (m, 1H), 8.18 (m, 1H), 6.98 (d, 2H), 4.65 (m, 1H), 2.95-2.37 (m, 2H), 1.57 (d, 3H).

Analysis calculated for $C_{10}H_9NO_4$: C, 57.97; H, 4.38 N, 6.76%.

Found: C, 57.93; H, 4.45 N, 6.72%.

PREPARATION F3

3-(4-Chlorophenoxy)butyric Acid

To a solution of 40 g (1 mol) sodium hydroxide in 400 ml water was added 128.6 g (1 mol) 4-chlorophenol and the reaction was heated at reflux for 15 minutes. To the refluxing solution was added 81.5 g (1 mol) of beta-butyrolactone dropwise over 1 hour. The reaction was cooled to 23° C., acidified with 100 ml concentrated hydrochloric acid and extracted with 2×500 ml diethyl ether. The ether layers were combined and extracted with 5×300 ml saturated aqueous sodium bicarbonate solution. The bicarbonate extracts were combined, acidified by slow dropwise addition of 160 ml concentrated hydrochloric acid and extracted with 250 ml diethyl ether. The latter ether extract was washed with brine, dried over magnesium sulfate and concentrated in vacuo to give the product as a white solid, 24 g (11%).

1H-NMR(CDCl3)delta(ppm): 10.5 (broad s, 1H), 7.12 (d, 2H), 6.73 (d, 2H), 4.67 (m, 1H), 3.0-2.27 (m, 2H), 1.33 (d, 3H).

PREPARATION F4

6-Chloro-2-methylchroman-4-one

The product of the preceding preparation (30.5 g, 142.1 mmol) was combined with 142 g methanesulfonic acid and 7.1 g phosphoruspentoxide and the slurry warmed on a steam bath for 15 minutes. The reaction was cooled to 23° C. and poured onto 500 ml ice and water. Extraction with 2×100 ml diethyl ether followed by washing of the ether with 2×150 ml 1N sodium hydroxide, 150 ml water and brine and then drying over magnesium sulfate and concentration in vacuo gave the product as a yellow solid, 22 g (79%); m.p. 99°-100° C.

1H-NMR(CDCl3)delta(ppm): 7.63 (m, 1H), 7.20 (m, 1H), 6.73 (m, 1H), 4.47 (m, 1H), 2.57 (m, 2H), 1.47 (d, 3H).

PREPARATION F4

By the two-step procedures of Preparations F1/F2 and F3/F4, the appropriately-substituted phenol and beta-butyrolactone were converted to aromatic substituted 2-methylchroman-4-ones as follows:

| Aromatic Substituent(s) | Overall Yield (%) | m.p. (°C.) | Molecular Formula | Analysis Calcd. C, H | Found C, H |
|---|---|---|---|---|---|
| None | 4.2 | oil | $C_{10}H_{10}O_2$[e] | — | — |
| 6-Cl | 8.7 | 99–100 | $C_{10}H_9ClO_2$[f] | 61.08, 4.61 | 61.26, 4.71 |
| 6-Br | 11.8 | 89–91 | $C_{10}H_9BrO_2$ | 49.82, 3.72 | 49.79, 3.59 |
| 6-SO$_2$CH$_3$ | 28.0 | 144–149 | $C_{11}H_{12}O_4S$ | 54.98, 5.03 | 55.17, 5.09 |
| 6-COC$_6$H$_5$ | 14.7 | 126–128 | $C_{17}H_{14}O_2$ | 76.67, 5.30 | 76.61. 5.31 |
| 6-Br—8-Cl | 24.0 | 131–134 | $C_{10}H_8BrClO_2$ | 43.59, 2.93 | 43.40, 2.83 |
| 6-NO$_2$—7-CH$_3$[a] | 2.2[b] | solid | — | — | — |
| 5-CH$_3$—6-NO$_2$[a] | 0.8 | 118–120 | $C_{11}H_{11}NO_4$ | 59.72, 5.01 | 59.49, 5.01 |
| 6-Cl—7-CH$_3$ | 2.0 | 53–55 | $C_{11}H_{11}ClO_2$ | 62.71, 5.26 | 62.82, 5.30 |
| 5,8-diCl | 13.3 | 97–100 | $C_{10}H_8Cl_2O_2$ | 51.97, 3.49 | 52.03, 3.52 |
| 8-Cl | 16.0 | 70–72 | $C_{10}H_9ClO_2$ | 61.08, 4.61 | 61.15, 4.74 |
| 5,6-diCl 6,7-diCl [c] | 21 | 135–140 | $C_{10}H_8Cl_2O_2$ | 51.97, 3.49 | 51.70, 3.51 |
| 5-Cl 7-Cl [d] | 14 | oil | $C_{10}H_9ClO_2$ | 61.08, 4.61 | 60.86, 4.68 |

[a]Both isomers derived from 3-methyl-4-nitrophenol and separated by chromatography on silica gel using 2:1 hexane:ether as eluant.
[b]Contaminated with 5-CH$_3$—7-NO$_2$ isomer by $^1$H—NMR. Pure 6-NO$_2$—7-CH$_3$ isomer was obtained below by Scheme G (see Example G4).
[c]As an approximately 1:1 mixture from 3,4-dichlorophenol. Pure 6,7-diCl isomer was obtained below by Scheme G (Examples G5/G6).
[d]As a mixture from 3-chlorophenol.
[e]Chemical Abstracts Registry No. 5631-75-4.
[f]Chemical Abstracts Registry Nos. 82320-21-6 and 37647-74-1.

By the same two-step method of Preparations F1/F2 and F3/F4, 3,4-dichlorophenyl mercaptan (23.9 g, 0.133 mol) was converted to 6,7-dichloro-2-methyl-2H,3H-1-thianaphthalene-4-one, recrystallized from hexane, 16.8 g; m.p. 104°–106° C.
Analysis Calculated for $C_{10}H_8OSCl_2$: C, 48.60; H, 3.26%.
Found: C, 48.44; H, 3.18%.

In like manner 4-nitrophenyl mercaptan (15 g, 0.097 mol) was converted to 6-nitro-2-methyl-2H,3H-1-thianaphthalene-4-one, 2.7 g; and 4-fluorophenyl mercaptan (20.0 g, 0.156 mol) was converted to intermediate 2-(4-fluorophenylthio)propionic acid [30.2 g; $^1$H-NMR(CDCl$_3$)delta(ppm): 1.32 (d, 3H, J=7), 2.53 (q, 2H, J=7,4), 3.52 (q, 1H, J=7), 6.80-7.60 (m, 4H)] and 44 g (0.20 mol) of intermediate prepared in this manner converted to 6-fluoro-2-methyl-2H,3H-1-thianaphthalene-4-one flash chromatographed on silica gel with 9:1 hexane:ethyl acetate as eluant to produce purified product as an oil, 34 g; m/e 196, 181, 154 (100%), 126.
Analysis Calculated for $C_{10}H_9OSF$: C, 61.20; H, 4.62; S, 16.34%.
Found: C, 59.84; H, 4.53; S, 16.58%.

SCHEME G

PREPARATION G1

3-(3-Chloro-4-fluorophenoxy)butyric Acid

To a solution of 27.2 g (0.68 mol) sodium hydroxide in 272 ml water was added 100 g (0.68 mol) 3-chloro-4-fluorophenol. The solution was warmed to reflux and 55.4 ml (0.68 mol) of beta-butyrolactone was added dropwise over a 1 hour period. The reaction was cooled to 23° C. and the pH brought to 7 with concentrated hydrochloric acid. The neutral solution was washed with 3×150 ml diethyl ether to remove unreacted phenol and then acidified to pH 2 with concentrated hydrochloric acid, extracted with 150 ml 1,2-dichloroethane, dried over magnesium sulfate and concentrated in vacuo to 4.3 g of an oil which by nuclear magnetic resonance examination was composed of 44 mol percent product and 56% 3-hydroxybutyric acid. The original diethyl ether washes were extracted with 3×150 ml saturated sodium bicarbonate. The combined bicarbonate solutions were extracted with 150 ml diethyl ether and then the pH was brought to 2 with concentrated hydrochloric acid. Extraction with diethyl ether, washing with brine and drying over magnesium sulfate and concentration in vacuo gave 16.2 g (10.2%) of title product as an oil.
$^1$H-NMR(CDCl$_3$)delta(ppm): 10.58 (broad s, 1H), 7.23-6.50 (m, 3H), 4.67 (m, 1H), 2.67 (m, 2H), 1.37 (d, 3H).

PREPARATION G2

7-Chloro-6-fluoro-2-methylchroman-4-one

To a solution of 10.0 g (43 mmol) 3-(3-chloro-4-fluorophenoxy)butyric acid in 21 ml 1,2-dichloroethane was added 8.96 g (43 mmol) phosphorus pentachloride in portions. Upon completion of the addition, the reaction was stirred 20 minutes at 23° C. and then added dropwise to a mechanically-stirred slurry of 17.2 g (129 mmol) aluminum chloride in 21 ml 1,2-dichloroethane. The reaction was cooled to 0° C. and 70 ml 1N HCl was added dropwise. Extraction with 2×100 ml diethyl ether followed by 70 ml 1N HCl, 2×50 ml 1N NaOH, 70 ml water and 70 brine, drying over magnesium sulfate and concentration in vacuo gave 7.75 g (84%) of a tan solid, m.p. 75°-76° C. An analytical sample was obtained by recrystallization of 500 mg from hexane to give 410 mg, m.p. 79°-81° C.
Analysis Calculated for $C_{10}H_8ClFO_2$: C, 55.96; H, 3.76%.
Found: C, 55.65; H, 3.74%.

PREPARATION G3

3-(3-Fluorophenoxy)butyric Acid

To a solution of 35.72 g (0.893 mol) sodium hydroxide in 357 ml water was added 100 g (0.893 mol) 3-fluorophenol. The reaction was heated to reflux and to the gently refluxing solution was added 72.8 ml (0.893 mol) beta-butyrolactone dropwise over 1.5 hours. The reaction was cooled to 23° C. and the pH brought to 2 with concentrated hydrochloric acid. The reaction was extracted with 300 ml diethyl ether and the ether layer was separated, washed with brine and then extracted with 3×200 ml saturated sodium bicarbonate. The combined bicarbonate layers were washed with 200 ml diethyl ether, acidified with 50 ml concentrated hydrochloric acid and extracted with 300 ml diethyl ether. The latter ether extract was washed with brine, dried over magnesium sulfate and concentrated in vacuo to give the product as a red oil, 31.6 g (17.9%).
$^1$H-NMR(CDCl$_3$)delta(ppm): 7.07 (m, 1H), 6.57 (m, 2H), 4.73 (q, 1H), 2.66 (t, 2H), 1.37 (d, 3H).

PREPARATION G4

7-Fluoro-2-methylchroman-4-one

To a solution of 31.6 g (159 mmol) 3-(3-fluorophenoxy)butyric acid in 75 ml 1,2-dichloroethane at 23° C. was added 33.1 g (159 mmol) phosphorus pentachloride in portions. After the addition was complete, the reaction was stirred at 23° C. for 20 minutes. This solution was added dropwise to a mechanically-stirred slurry of 63.7 g (478 mmol) aluminum chloride in 75 ml 1,2-dichloroethane. After the reaction was complete, the solution was cooled in an ice bath and 250 ml of 1N hydrochloric acid was added dropwise. The reaction was extracted with 2×300 ml diethyl ether and the combined organics were washed with 250 ml 1N hydrochloric acid, 2×200 ml 1N sodium hydroxide, 250 ml water and brine, dried over magnesium sulfate, and concentrated in vacuo to an oil which crystallized on standing, 24.8 g (87%); m.p. 42°-47° C. An analytical sample was prepared by flash chromatography of 1 g on 40 cc silica gel using diethyl ether:hexane 20:1 as eluant to give 0.5 g white solid, m.p. 46°-50° C.
$^1$H-NMR(CDCl$_3$)delta(ppm): 7.85 (m, 1H), 6.67 (m, 2H), 4.60 (m, 1H), 2.67 (m, 2H), 1.53 (d, 3H).
Analysis Calculated for C$_{10}$H$_9$FO$_2$: C, 66.66; H, 5.04%.
Found: C, 66.38; H, 5.03%.

By the two-step method of Preparations G1/G2 and G3/G4, 3-methyl-4-nitrophenol and 3-chlorophenol were reacted with beta-butyrolactone and the intermediate phenoxybutyric acid derivative cyclized to form, respectively, 2,7-dimethyl-6-nitrochroman-4-one [overall yield 13.0%; m.p. 110°-113° C.;
Analysis Calculated for C$_{11}$H$_{11}$NO$_4$: C, 59.72; H, 5.01; N, 6.33%.
Found: C, 59.71; H, 5.02; N, 6.17%.] and 7-chloro-2-methylchroamn-4-one [overall yield 14.7%; oil;
Analysis Calculated for C$_{10}$H$_9$ClO$_2$: C, 61.08; H, 4.61%.
Found: C, 60.86; H, 4.68%.]

PREPARATION G5

3-(3,4-Dichlorophenoxy)butyric Acid

A solution of 159.6 g (0.979 mol) 3,4-dichlorophenol dissolved in 392 ml (0.979 mol) 2.5N sodium hydroxide was heated at reflux for 15 minutes. To the refluxing solution 84.3 g (80 ml, 0.979 mol) beta-butyrolactone was added dropwise over a 3 hour period. The reaction was then cooled to 23° C., the pH adjusted to 2 with 93 ml concentrated hydrochloric acid and the reaction extracted with 2×500 ml diethyl ether. The ether layers were combined and washed with 4×520 ml saturated sodium bicarbonate solution. The combined bicarbonate layers were adjusted to pH 2 with 223 ml concentrated hydrochloric acid and extracted with 2×500 ml diethyl ether. The latter ether layers were combined, washed with 2×500 ml water and 500 ml brine, dried over magnesium sulfate and concentrated in vacuo to a yellow solid, 61.4 g (25%). Trituration with hexane-ether gave a white solid, m.p. 83°-86° C.
$^1$H-NMR(CDCl$_3$)delta(ppm): 10.27 (broad s, 1H), 7.23-6.37 (m, 3H), 4.67 (m, 1H), 2.63 (m, 2H), 1.33 (d, 3H).

PREPARATION G6

5,6-Dichloro-2-methylchroman-4-one

The product of the preceding Preparation (39.0 g, 0.157 mol) was dissolved in 75 ml methylene chloride and 32.7 g (0.154 mol) phosphorus pentachloride was added at 23° C. over a 20 minute period. This solution was added dropwise to a solution of 32.7 g titanium tetrachloride in 150 ml methylene chloride at −78° C. with a resultant brick red color forming. The reaction was warmed to 0° C. and 100 ml water was slowly added. Methylene chloride, 200 ml, was added and titanium dioxide was removed by filtration through diatomaceous earth. The organic layer was separated and washed with 100 ml water and 100 ml brine, dried over magnesium sulfate and concentrated in vacuo to a yellow oil, 24.4 g. Trituration with isopropyl alcohol gave a white solid which was collected by filtration and dried to give the title compound, 3.25 g (9%); m.p. 135°-140° C.
$^1$H-NMR(CDCl$_3$)delta(ppm): 7.40 (d, 1H), 6.80 (d, 1H), 4.57 (m, 1H), 2.70 (m, 2H), 1.50 (d, 3H).
Analysis Calculated for C$_{10}$H$_8$Cl$_2$O$_2$: C, 51.97; H, 3.49%.
Found: C, 51.70; H, 3.51%.

SCHEME H

PREPARATION H1

6-Chloro-7-methoxy-2-methylchroman-4-one

In a polyethylene bottle were combined 3.3 g (13 mmol) 3-(4-chloro-3-methoxyphenoxy)butyric acid and 30 ml liquid hydrogen fluoride. The reaction mixture was allowed to stand at 23° C. for 72 hours, then poured over ice and extracted with 2×100 ml diethyl ether. The ether was washed with 2×100 ml water, 100 ml saturated sodium bicarbonate and brine, dried over magnesium sulfate and concentrated in vacuo to give the product as a yellow solid, 2.7 g (93%).
$^1$H-NMR(CDCl$_3$)delta(ppm): 7.82 (s, 1H), 6.47 (s, 1H), 4.53 (m, 1H), 3.93 (s, 3H), 2.62 (m, 2H), 1.52 (d, 3H).

SCHEME I

PREPARATION I1

6,8-Dichloro-2-methylchroman-4-one

To a mechanically stirred paste of 580 ml polyphosphoric acid was added 94.6 g (0.58 mol) 2,4-dichlorophenol and 100.0 g (1.16 mol) crotonic acid. The reaction was heated at 120° C. for 3 hours, then at 140° C. for 5 hours, and then quenched by pouring onto 2 liters ice. 3 Liters of 2N sodium hydroxide was added to partially neutralize the acid, resulting in the formation of a precipitate which was collected by filtration. This was taken up in 1.5 liters chloroform, filtered, washed with 1 liter water, brine, dried over magnesium sulfate and concentrated in vacuo to 100 g of crude 3,4-dichlorophenyl crotonate as a brown oil. This was combined with 250 ml concentrated sulfuric acid and heated at 70° C. for 1 hour. The reaction was cooled to 23° C. and poured onto 1.5 liters ice with formation of a black gummy solid. This was collected by filtration and the cake triturated with 3×250 ml methylene chloride. The combined triturates were dried over magnesium sulfate and concentrated in vacuo to 10 g of oily solid. This was redissolved in 50 ml methylene chloride and added to 300 ml diethyl ether to precipitate 1 g of black solid which was removed by filtration. The filtrate was concentrated in vacuo to 7.9 g of a brown solid. This was flash chromatographed on 400 cc silica gel using 6:1 hexane:diethyl ether as eluant to give product as a white solid, 5 g (3.7%); m.p. 98°–102° C.

$^1$H-NMR(CDCl$_3$)delta(ppm): 7.63 (d, 1H), 7.40 (d, 1H), 4.60 (m, 1H), 2.65 (m, 2H), 1.55 (d, 3H).

An analytical sample was prepared by recrystallization from hexane, m.p. 105°–108° C.

Analysis Calculated for C$_{10}$H$_8$Cl$_2$O$_2$: C, 51.97; H, 3.49%.

Found: C, 52.21; H, 3.51%.

The Chemical Abstracts Registry No. for this compound is 76143-73-2.

SCHEME J

PREPARATION J1

6-Fluoro-2-methylchroman-4-one

A mixture of 100 g (0.89 mol) 4-fluorophenol, 150 g (1.74 mol) crotonic acid and 500 ml polyphosphoric acid was stirred at 135° C. for 2.5 hours. The reaction was cooled to 90° C. and poured onto 1.5 liters ice. The reaction was extracted with 3×500 ml ethyl acetate. The organic layers were combined, filtered through diatomaceous earth, washed with 2×500 ml water and then brine, dried over magnesium sulfate and concentrated in vacuo to a thick, dark brown oil. This was extracted with refluxing hexane in a Soxhlet extractor to give 103 g amber oil which was chromatographed on 2 kilograms silica gel using 3:2 methylene chloride:hexane as eluant to give, after cold hexane trituration, 33.1 g (18%) of product as light tan crystals; m.p. 70°–71° C.

$^1$H-NMR(CDCl$_3$)delta(ppm): 7.23–6.67 (m, 3H), 4.50 (m, 1H), 2.67 (m, 2H), 1.48 (d, 3H).

The Chemical Abstract Registry Numbers for this compound are 88754-96-5 and 82320-16-9.

PREPARATION J1
By the same method, the appropriately substituted phenol and crotonic acid were converted to aromatic substituted 2-methylchroman-4-ones as follows:

| Aromatic Substitutent(s) | Overall Yield (%) | m.p. (°C.) | Molecular Formula | Analysis Calcd. C, H | Analysis Found C, H |
|---|---|---|---|---|---|
| None | 2.6 | oil | [b] | — | — |
| 6-CH$_3$ | 24.1 | 51–53 | C$_{11}$H$_{12}$O$_2$[c] | 74.98, 6.86 | 74.83, 6.55 |
| 6-Cl | 3.0 | 99–100 | C$_{10}$H$_9$ClO$_2$[d] | 61.08, 4.61 | 61.26, 4.71 |
| 6-Cl—CH$_3$ | 5.3 | 95–98 | C$_{11}$H$_{11}$ClO$_2$ | 62.71, 5.26 | 62.65, 5.23 |

[a]Chemical Abstracts Registry Nos. 88754-96-5 and 82320-16-9.
[b]Chemical Abstracts Registry No. 5631-75-4.
[c]Chemical Abstracts Registry No. 51423-95-1.
[d]Chemical Abstracts Registry Nos. 82320-21-6 and 37674-74-1.

SCHEME K

PREPARATION K1

6-Chloro-3,4-dihydro-2-methyl-2H-benzo[h]chroman-4-one

A mixture of 185 ml (2.85 mol) methanesulfonic acid, 5.56 g (39 mmol) phosphorus pentoxide, 24.1 g (280 mmol) crotonic acid and 50 g (280 mmol) 4-chloro1-naphthol were stirred at 23° C. for 1 hour and then at 55° C. for 4 hours. The reaction was cooled to 23° C. and poured onto 1 liter ice and water and extracted with 3×100 ml diethyl ether. The ether layers were combined, washed with 3×100 ml 1N sodium hydroxide and 100 ml brine, dried over magnesium sulfate and concentrated in vacuo to a black solid, 16.0 g. Flash chromatography on 600 cc silica gel using 6:1 hexane:diethyl ether as eluant gave the product, 4.58 g (67%); m.p. 134°–136° C.

$^1$H-NMR(CDCl$_3$)delta(ppm): 8.33–7.27 (m, 4H), 7.80 (s, 1H), 4.70 (m, 1H), 2.70 (d, 2H), 1.63 (d, 3H).

An analytical sample was crystallized from isopropyl ether and methylene chloride; m.p. 135°–137° C.

Analysis Calculated for C$_{14}$H$_{11}$ClO$_2$: C, 68.16; H, 4.49%.

Found: C, 68.04; H, 4.43%.

PREPARATION K1
By using the appropriately substituted phenol and crotonic acid or analog, the same method was employed to prepare substituted chroman-4-ones as follows:

| Aromatic Substitutent(s) | Overall Yield (%) | m.p. (°C.) | Molecular Formula | Analysis Calcd. C, H | Analysis Found C, H |
|---|---|---|---|---|---|
| 7,8-diCl—2-CH$_3$ | 12.1 | 112–115 | C$_{10}$H$_8$Cl$_2$O$_2$ | 51.97, 3.49 | 51.84, 3.47 |
| 6-F—C$_2$ | | | | | |
| 6-F—2-(n-C$_5$) | 5.4 | oil | — | — | — |
| 6-F-2-(n-C$_3$H$_7$) | 5.3 | oil | — | — | — |
| 6-F—cis-2,3-diCH$_3$ | 7.8 | oil | — | — | — |

SCHEME L

PREPARATION L1

6-Chloro-7-methoxy-2-methylchroman-4-one

A solution of 1.0 g (6.3 mmol) 4-chloro-3-methoxyphenol and 5.4 g (6.3 mmol) crotonic acid in 15 ml methane sulfonic acid was heated at 95° C. under nitrogen for 20 hours. The reaction was cooled to 23° C., poured onto 150 ml ice and water and extracted with 100 ml ethyl acetate. The ethyl acetate extract was successively washed with 100 ml water, 2×100 ml 1N sodium hydroxide and 100 ml brine, dried over magnesium sulfate and concentrated in vacuo to a purple crystalline solid. This was purified by flash chromatography on 150 cc silica gel using chloroform as eluant to give the product as a yellow crystalline solid, 1.1 g (78%); m.p. 96°-100° C.
$^1$H-NMR(CDCl$_3$)delta(ppm): 7.65 (s, 1H), 6.32 (s, 1H), 4.45 (m, 1H), 3.80 (s, 3H), 2.48 (d, 2H), 1.42 (d, 3H) (substantially the same as the product of Preparation H1, above).
Analysis Calculated for C$_{11}$H$_{11}$ClO$_3$: C, 58.29; H, 4.89%.
Found: C, 58.29; H, 4.94%.

PREPARATION L2

6-Fluoro-2-methylchroman-4-one

A mixture of 56.1 g (0.5 mol) 4-fluorophenol, 172 g (2 mol) crotonic acid and 1120 ml methane sulfonic acid was heated at 92° C. for 20 hours. The reaction was cooled to 0° C., poured onto 2 liters ice and 2 liters water and extracted with 3×800 ml diethyl ether. The combined organic layers were washed with 3×500 ml water, 4×500 ml 1N sodium hydroxide, 2×500 ml water and 500 ml brine, dried over magnesium sulfate and concentrated in vacuo to give 48.5 g crude solid. The latter was purified by flash chromatography on 1000 cc silica gel using diethyl ether:hexane (1:10) as eluant. The title compound was obtained as a yellow solid, 37 g (41%); m.p. 65°-68° C. The Chemical Abstracts Registry Nos. for this compound are 88754-96-5 and 82320-16-9.

By the method of Preparations L1 and L2, and 3-bromophenol, 3-chlorophenol and 3-fluorophenol were converted, respectively, to 7-bromo-2-methylchroman-4-one (30% yield; oil); 7-chloro-2-methylchroman-4-one (35% yield; oil;
Analysis Calculated for C$_{10}$H$_9$ClO$_2$: C, 61.08; H, 4.61%.
Found: C, 60.86; H, 4.68%.) and 7-fluoro-2-methylchroman-4-one (35% yield; m.p. 46°-50° C.;
Analysis Calculated for C$_{10}$H$_9$FO$_2$: C, 66.66; H, 5.04%.
Found: C, 66.38; H, 5.03%.) By the same method, 2,3-dichlorophenol was converted to 7,8-dichloro-2-methylchroman-4-one (12%; m.p. 112°-115° C.).

Likewise, 3,4-difluorophenol was converted to 6,7-difluoro-2-methylchroman-4-one in 19.5% yield; m.p. 73°-76° C.; 3-bromo-4-fluorophenol was converted to a 2:3 mixture of 5-bromo-6-fluoro-2-methylchroman-4-one and 7-bromo-6-fluoro-2-methylchroman-4-one, in 9.6% and 14.4% yields, respectively; and 4-chloro-3-ethylphenol was converted to 6-chloro-7-ethyl-2-methylchroman-4-one in 39% yield; m.p. 42°-45° C.
Analysis Calculated for C$_{12}$H$_{13}$ClO$_2$: C, 64.14; H, 5.83%.
Found: C, 64.39; H, 5.96%.

MISCELLANEOUS PREPARATIONS

PREPARATION M1

7-Fluoro-6-nitro-2-methylchroman-4-one

To a solution of 4.18 g (23.2 mmol) 7-fluoro2-methylchroman-4-one in 7 ml concentrated sulfuric acid at 0° C. was added dropwise over 20 minutes a solution of 1.41 ml (30.2 mmol) nitric acid (s.g. 1.5, 90%) in 3 ml concentrated sulfuric acid. The reaction was poured onto 100 ml ice and water and extracted with 150 ml ethyl acetate. The organic layer was washed with 4×50 ml water and then brine, dried over magnesium sulfate and concentrated in vacuo to give 5.93 g of a light brown semi-solid. Trituration with cold diethyl ether gave the product as a yellow solid, 1.9 g (37%); m.p. 139°-141° C.
$^1$H-NMR(20:1 CDCl$_3$-Me$_2$SO)delta(ppm): 8.57 (d, 1H, J=9 Hz), 6.80 (d, 1H, J=12 Hz), 4.73 (m, 1H), 2.77 (m, 2H), 1.60 (d, 3H).
Analysis Calculated for C$_{10}$H$_8$FNO$_4$: C, 53.34; H, 3.58; N, 6.22%.
Found: C, 53.17; H, 3.72; N, 6.30%.

PREPARATION M2

6-Amino-7-fluoro-2-methylchroman-4-one

A solution of 1.2 g (5.33 mmol) of title product of the preceding Preparation in 25 ml ethyl acetate was hydrogenated at 23° C. at atmospheric pressure for 16 hours with 0.120 g of 10% palladium-on-carbon as catalyst. The reaction was filtered through diatomaceous earth and concentrated in vacuo. The residue was partitioned between 15 ml 1N hydrochloric acid and 30 ml diethyl ether. The layers were separated and the ether was extracted with 10 ml 1N hydrochloric acid. The combined acid layers were washed with 2×15 ml diethyl ether and then were made basic with 26 ml 1N sodium hydroxide. Extraction with 3×25 ml diethyl ether, washing these combined ether extracts with water followed by brine and drying over magnesium sulfate followed by concentration in vacuo gave the product as a yellow solid, 838 mg (81%); m.p. 135°-138° C. $^1$H-NMR(CDCl$_3$)delta(ppm): 7.13 (d, 1H, J=10 Hz), 6.48 (d, 1H, J=11 Hz), 4.40 (m, 1H), 3.33 (s, 2H), 2.50 (m, 2H), 1.35 (d, 3H).

PREPARATION M3

6-Chloro-7-fluoro-2-methylchroman-4-one

To a solution of 7 ml concentrated hydrochloric acid and 7 ml water was added 0.734 g (3.76 mmol) of title product of the preceding Preparation. The reaction was heated at 60° C. for 10 minutes and then cooled in an ice bath. To this was added dropwise over 15 minutes a solution of 0.275 g (3.98 mmol) sodium nitrite in 7 ml water. This solution was slowly added with agitation to a preformed solution of 0.482 g (4.87 mmol) cuprous chloride in 7 ml concentrated hydrochloric acid at 0° C. After gas evolution stopped, the reaction was warmed to 23° C. and then was warmed at 60° C. for 10 minutes. The resultant precipitate was collected by filtration, washed successively with water, saturated sodium bicarbonate and water, and dried in vacuo to give 0.540 g (67%) of title product; m.p. 88°-90° C. $^1$H-NMR(CDCl$_3$)delta(ppm): 7.90 (d, 1H, J=9 Hz), 6.75 (d, 1H, J=11 Hz), 4.28 (m, 1H), 2.68 (m, 2H), 1.53 (d, 3H).

Analysis Calculated for $C_{10}H_8ClFO_2$: C, 55.96; H, 3.76%.
Found: C, 55.65; H, 3.72%.

PREPARATION M4

7-Chloro-6-nitro-2-methylchroman-4-one

7-Chloro-2-methylchroman-4-one (4.56 g, 23.2 mmol) was dissolved in 7 ml concentrated sulfuric acid at 0°–5° C. and cooled in an acetone-ice bath. Nitric acid (1.41 ml, s.g. 1.5, 90%) in 3 ml concentrated sulfuric acid was added dropwise over 20 minutes. The resulting viscous mixture was poured into 150 ml ice and water and extracted with 200 ml ethyl acetate. The organic layer was separated, washed 4×50 ml water and then brine, dried over magnesium sulfate, and stripped to a tan solid, 5.8 g. The latter was chromatographed on 500 cc silica gel, initially eluting with 5 liters 1:10 diethyl ether:hexane to remove starting material and then with 5 liters of 1:5 diethyl ether:hexane to obtain title product as a white solid, 2 g (36%); m/e 241(P+), 226, 199, 183, 169, 154, 141. $^1$H-NMR indicates contamination with about 44% of the 7-chloro-8-nitro isomer.

Pure 7-chloro-6-nitro isomer was obtained by crystallization from acetonitrile, m.p. 158°–161° C.
Analysis calculated for $C_{10}H_8ClNO_4$: C, 49.70; H, 3.34; N, 5.80%.
Found: C, 49.68; H, 3.36; N, 5.63%.

PREPARATION M5

6-Nitro-2,2-dimethylchroman-4-one 2,2-Dimethylchroman-4-one (4 g, 23.2 mmol) was added portionwise over 10 minutes to 7 ml of concentrated sulfuric acid at 0°–5° C., then cooled in an acetone-ice bath as concentrated nitric acid (s.g. 1.5, 90%, 1.4 ml) in 3 ml concentrated sulfuric acid was added dropwise over 20 minutes. The resulting mixture was poured into 100 ml ice and water and extracted 2×50 ml ethyl acetate. The organic layers were combined, washed 4×50 ml water and then brine, dried over magnesium sulfate, stripped to solids (5.3 g) and chromatographed on 500 g silica gel, gradiently eluting with 20:1, 15:1, 10:1 and finally 5:1 hexane:diethyl ether to yield title product as a white solid, 2.1 g (39%); tlc Rf 0.3 (1:1 diethyl ether:hexane); m/e 221(P+), 206, 166, 120.

PREPARATION M6

6-Nitro-7-bromo-2-methylchroman-4-one

By the method of Preparation M1, 7-bromo-2-methylchroman-4-one was converted to title product in 9% yield; m.p. 125°–128° C.
$^1$H-NMR(CDCl$_3$)delta(ppm): 8.27 (s, 1H), 7.32 (s, 1H), 4.73 (m, 1H), 2.75 (m, 2H), 1.57 (d, 3H).
Analysis Calculated for $C_{10}H_8BrNO_4$: C, 41.98; H, 2.82; N, 4.90%.
Found: C, 41.80; H, 2.72; N, 4.87%.

PREPARATION M7

6-Cyano-7-fluoro-2-methylchroman-4-one

By the method of Example M3, substituting cuprous cyanide for cuprous chloride, 6-amino-7-fluoro-2-methylchroman-4-one was converted to title product in 1% yield.
$^1$H-NMR(CDCl$_3$)delta(ppm): 8.15 (d, 1H), 6.77 (d, 1H), 4.67 (m, 1H), 2.72 (m, 2H), 1.54 (d, 3H).

PREPARATION M8

7-Bromo-6-chloro-2-methylchroman-4-one

The hydrogenation method of Example M2 followed by the Sandmeyer method of Example M3 was employed to converrt the product of Preparation M6 to present product in 4% yield; m.p. 67°–70° C.
$^1$H-NMR(CDCl$_3$)delta(ppm): 7.88 (s, 1H), 7.29 (s, 1H), 4.57 (m, 1H), 2.68 (m, 2H), 1.51 (d, 2H).
Analysis Calculated for $C_{10}H_8BrClO_2$: C, 43.59; H, 2.93%.
Found: C, 43.51; H, 3.00%.

PREPARATION M9

6-Fluoro-2-methyl-2H,3H-1-thianaphthalene-4-one 1,1-Dioxide

By the method of Example 108, 6-fluoro-2-methyl2H,3H-1-thianaphthalene-4-one was converted to the corresponding 1-oxide. In turn, 1 g of the latter was further oxidized according to the method of Example 110 to produce an essentially quantitative yield of title product as an oil which crystallized on standing, m.p. 113°–114° C.; m/e 95.9, 121.9 (100%), 169.9, 186.9.

PREPARATION M10

6-Cyano-2-benzylchroman-4-one

Methyl 2-benzylchroman-4-one-6-carboxylate, the product of Preparation A33, is converted to the corresponding amide by the action of a molar excess of ammonia in aqueous methanol, recovered by simple stripping of the solvent and excess ammonia. In turn, the amide is converted to the title nitrile by the action of p-toluenesulfonyl chloride on a pyridine solution of the amide, according to the conditions of Stephens et al., J. Am. Chem. Soc., Vol. 77, pp 1701–1702 (1955). This product is well suited for the preparation of 6-cyano-c-4-hydroxy-r-2-benzylchroman-4-acetic acid by the methods of Examples above.

PREPARATION M11

4-Chloro-3-methoxyaniline

2-Chloro-5-nitroanisol (10 g, 0.053 mol), iron powder (15 g, 0.26 mol) and glacial acetic acid (20 ml, 0.355 mol) were combined in 125 ml ethanol. Concentrated HCl (2 drops) was added and the mixture refluxed 2 hours. Additional iron powder (5 g) and concentrated HCl (1 drop) were added and reflux continued for an additional 16 hours. The reaction mixture was cooled, poured into equal volumes each of ice/water and ether, filtered and the layers separated. The aqueous layer was extracted with fresh ether and the combined ether layers extracted with 1N HCl. The original aqueous and 1N HCl extract were combined, the pH adjusted to 6 with saturated Na$_2$CO$_3$ and extracted with fresh ether. The last ether extract was dried over MgSO$_4$ and stripped to yield title product, 82 g, m.p. 77°–79° C.

PREPARATION M12

4-Chloro-3-methoxyphenol

The product of the preceding Preparation (8.2 g, 0.052 mol) was dissolved in 50 ml concentrated H$_2$SO$_4$ by stirring and warming. The solution was cooled and slowly and carefully diluted, with stirring, with 50 ml H$_2$O (reverse addition is preferred). At 0°, NaNO$_2$ (3.8 g, 0.055 mol) in 10 ml H$_2$O was added dropwise. The mixture was slowly warmed to room temperature, stirred for 15 minutes, then warmed to 50° C. until gas evolution ceased. The mixture was cooled, diluted with an equal volume of water, saturated with excess NaCl and extracted with an equal volume of ether. The ether extract was dried over MgSO4, stripped to an oil and chromatographed on 250 cc silica gel with CHCl3 as eluant to yield purified title product, 1.7 g, having $^1$H-NMR consistent with its structure, used as starting material for Preparation L1, above.

PREPARATION M13

6-Chloro-7-hydroxy-2-methylchroman-4-one

The product of Preparations H1/L1 (150 mg, 0.66 mmol) was heated at 95° C. for 16 hours in a mixture of 2 ml 48% HBr and 1 ml glacial acetic acid. An additional 2 ml 48% HBr was added and heating continued for 3 days. The mixture was cooled, diluted with 5 ml H2O, and extracted with 10 ml ethyl acetate. The organic layer was separated, washed with H2O and brine, dried over MgSO4, stripped and the residue chromatographed in silica gel with 9:1 CHCl3:CH3OH as eluant to yield purified title product, 130 mg, having $^1$H-NMR consistent with its structure.

PREPARATION M14

7-Benzyloxy-6-chloro-2-methylchroman-4-one

Product prepared according to the preceding Preparation (1.0 g, 0.0047 ml), benzyl chloride (1.1 ml, 1.2 g, 0.0094 mol) and triethylamine (0.95 g, 0.0094 mol) were combined in 10 ml CH2Cl2 and refluxed 18 hours. The mixture was cooled, diluted with an equal volume CHCl3, washed in sequence with H2O, saturated NaHCO3 and H2O, dried over MgSO4, stripped and the residue chromatographed in silica gel with CHCl3 eluant, 0.61 g, having $^1$H-NMR consistent with its structure.

What is claimed is:

1. A racemic compound having the relative stereochemical formula or a chiral compound having the absolute stereochemical formula

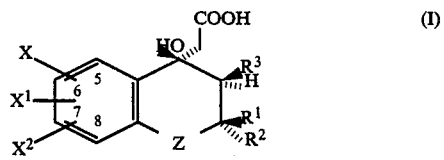

wherein

Z is —O—, —S—,

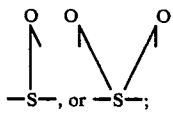

$R^1$ and $R^2$ are taken separately;

$R^1$ is $(C_1-C_4)$alkyl, trifluoromethyl or $(CH_2)_nAr$ where n is 0, 1 or 2 and Ar is phenyl or phenyl mono- or disubstituted by methoxy, fluoro, chloro or bromo, where disubstituents are the same or different; and $R^2$ is hydrogen, methyl or ethyl; or $R^1$ and $R^2$ are taken together and are $(CH_2)_4$ or $(CH_2)_5$;

$R^3$ is hydrogen or methyl; with the provisos that when either Z is other than —O—, or $R^1$ is other than methyl, ethyl or trifluoromethyl, both $R^2$ and $R^3$ are hydrogen;

X is hydrogen, a first substituent at the 6-position which is fluoro, chloro, bromo, methyl, nitro, cyano, methanesulfonyl or benzoyl, with the proviso that when Z is other than —O—, X is other than hydrogen and is a first substituent at the 6-position which is fluoro, chloro, cyano or nitro; and $X^1$ and $X^2$ are taken separately;

$X^1$ is hydrogen, a first substituent at the 7-position which is fluoro, chloro, bromo, carboxy, or methyl, or a second substituent at either the 5- or 7-position which is fluoro, chloro, bromo, $(C_1-C_3)$alkyl, $(C_1-C_3)$alkoxy or benzyloxy; and $X^2$ is hydrogen, or a first or second substituent at the 8-position which is fluoro, chloro, bromo or $(C_1-C_3)$alkyl; or $X^1$ and $X^2$ are taken together and are 7,8-benzo; or a pharmaceutically-acceptable cationic salt thereof.

2. A compound of claim 1 which is optically active.
3. A compound of claim 1 wherein Z is —O—.
4. A compound of claim 2 wherein Z is —O—.
5. A compound of claim 1 wherein $R^1$ is methyl and $R^2$ and $R^3$ are each hydrogen.
6. A compound of claim 3 wherein $R^1$ is methyl and $R^2$ and $R^3$ are each hydrogen.
7. A compound of claim 4 wherein $R^1$ is methyl and $R^2$ and $R^3$ are each hydrogen.
8. A compound of claim 1 wherein X is 6-fluoro, 6-chloro, 6-cyano or 6-nitro; $X^1$ is hydrogen, 7-fluoro, 7-chloro, 7-bromo, 7-methyl, 7-ethyl or 7-methoxy; and $X^2$ is hydrogen.
9. A compound of claim 8 wherein Z is —O—.
10. A compound of claim 9 wherein $R^1$ is methyl and $R^2$ and $R^3$ are each hydrogen.
11. A compound of claim 10 which is racemic.
12. A compound of claim 11 wherein X is 6-chloro, or 6-fluoro, $X^1$ is 7-bromo, 7-chloro, 7-fluoro or 7-methyl, and $X^2$ is hydrogen.
13. The compound of claim 12 wherein X is fluoro and $X^1$ is chloro.
14. The compound of claim 12 wherein X is fluoro and $X^1$ is bromo.
15. The compound of claim 12 wherein X and $X^1$ are each chloro.
16. The compound of claim 12 wherein X is chloro and $X^1$ is bromo.
17. The compound of claim 12 wherein X is chloro and $X^1$ is methyl.
18. A compound of claim 10 which is chiral.
19. The compound of claim 18 wherein X is 6-fluoro and $X^1$ is 7-chloro.
20. The compound of claim 18 wherein $X^1$ is 6-chloro and $X^2$ is 7-chloro.
21. A compound of claim 1 wherein Z is —O—, $R^1$ is other than methyl, $R^2$ and $R^3$ are each hydrogen, X is 6-fluoro or 6-chloro, $X^1$ is 7-fluoro, 7-chloro or hydrogen and $X^2$ is hydrogen.
22. The racemic compound of claim 21 wherein $R^1$ is ethyl, X is 6-fluoro and $X^1$ is hydrogen.
23. The racemic compound of claim 21 wherein $R^1$ is 2-phenylethyl, X is 6-fluoro and $X^1$ is hydrogen.
24. The racemic compound of claim 21 wherein $R^1$ is trifluoromethyl, X is 6-chloro and $X^1$ is 7-chloro.
25. A compound of claim 1 wherein Z is —S—,

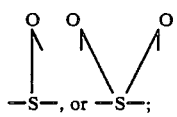

R¹ is methyl, R² and R³ are each hydrogen, X is 6-fluoro, 6-chloro or 6-nitro, X¹ is hydrogen or 7-chloro and X² is hydrogen.

26. A racemic compound of claim 25 wherein Z is —S—.

27. The compound of claim 26 wherein X is 6-fluoro and X¹ is hydrogen.

28. The compound of claim 26 wherein X is 6-chloro and X¹ is 7-chloro.

29. The compound of claim 26 wherein X is 6-nitro and X¹ is hydrogen.

30. A pharmaceutical composition of the control of chronic diabetic complications in mammals which comprises a compound of claim 1 in a pharmaceutically-acceptable carrier.

31. A method of controlling chronic diabetic complications which comprises administering to a mammal suffering from chronic diabetes a chronic diabetic complication controlling amount of a compound of claim 1.

32. A method of controlling chronic diabetic complications which comprises administering to a mammal suffering from chronic diabetes a chronic diabetic complication controlling amount of a compound of claim 3.

33. A method of controlling chronic diabetic complications which comprises administering to a mammal suffering from chronic diabetes a chronic diabetic complication controlling amount of a compound of claim 4.

34. A method of controlling chronic diabetic complications which comprises administering to a mammal suffering from chronic diabetes a chronic diabetic complication controlling amount of a compound of claim 10.

35. A method of controlling chronic diabetic complications which comprises administering to a mammal suffering from chronic diabetes a chronic diabetic complication controlling amount of a compound of claim 21.

36. A method of controlling chronic diabetic complications which comprises administering to a mammal suffering from chronic diabetes a chronic diabetic complication controlling amount of a compound of claim 25.

37. A racemic compound having the relative stereochemical formula or a chiral compound having the absolute stereochemical formula

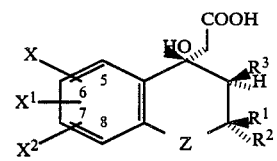

wherein

Z is —O—, —S—,

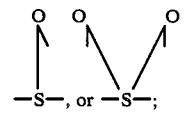

R is (C₁-C₄)alkyl, allyl or phenyl;

R¹ and R² are taken separately;
  R¹ is (C₁-C₄)alkyl, trifluoromethyl or (CH₂)ₙAr where n is 0, 1 or 2 and Ar is phenyl or phenyl mono- or disubstituted by methoxy, fluoro, chloro or bromo, where disubstituents are the same or different; and
  R² is hydrogen, methyl or ethyl; or
R¹ and R² are taken together and are (CH₂)₄ or (CH₂)₅;
R³ is hydrogen or methyl; with the provisos that when either Z is other than —O—, or R¹ is other than methyl, ethyl or trifluoromethyl, both R² and R³ are hydrogen;
X is hydrogen, a first substituent at the 6-position which is fluoro, chloro, bromo, methyl, nitro, cyano, methanesulfonyl or benzoyl, with the proviso that when Z is other than —O—, X is other than hydrogen and is a first substituent at the 6-position which is fluoro, chloro, cyano or nitro; and
X¹ and X² are taken separately;
  X¹ is hydrogen, a first substituent at the 7-position which is fluoro, chloro, bromo or methyl, or a second substituent at either the 5-or 7-position which is fluoro, chloro, bromo, (C₁-C₃)alkyl, (C₁-C₃) alkoxy or benzyloxy; and
  X² is hydrogen, or a first or second substituent at the 8-position which is fluoro, chloro, bromo or (C₁-C₃)alkyl; or
X¹ and X² are taken together and are 7,8-benzo; or a pharmaceutically-acceptable cationic salt thereof.

38. A compound of claim 37 wherein R is ethyl.

* * * * *